(12) United States Patent
Thompson, III et al.

(10) Patent No.: US 7,388,007 B2
(45) Date of Patent: Jun. 17, 2008

(54) GAMMA-LACTAMS AS BETA-SECRETASE INHIBITORS

(75) Inventors: Lorin A. Thompson, III, Higganum, CT (US); Kenneth M. Boy, Durham, CT (US); Jianliang Shi, Hamden, CT (US); John E. Macor, Gilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 526 days.

(21) Appl. No.: 11/206,441

(22) Filed: Aug. 18, 2005

(65) Prior Publication Data

US 2006/0046984 A1    Mar. 2, 2006

Related U.S. Application Data

(60) Provisional application No. 60/604,624, filed on Aug. 26, 2004, provisional application No. 60/660,433, filed on Mar. 10, 2005.

(51) Int. Cl.
    A61K 31/4025    (2006.01)
    A61K 31/5377    (2006.01)
    C07D 207/04     (2006.01)
    C07D 413/12     (2006.01)

(52) U.S. Cl. .................. 514/237.2; 544/106; 544/111; 544/141; 546/184; 546/192; 546/208; 548/517; 548/518; 514/231.2; 514/235.5; 514/408; 514/422

(58) Field of Classification Search ................ 544/106, 544/111, 141; 546/184, 192, 208; 548/517, 548/518; 514/231.2, 237.2, 408, 422
See application file for complete search history.

(56) References Cited

U.S. PATENT DOCUMENTS

| | | | |
|---|---|---|---|
| 4,705,846 A | 11/1987 | Thaisrivongs | |
| 5,120,718 A | 6/1992 | Goldman et al. | |
| 5,164,388 A | 11/1992 | De et al. | |
| 5,258,362 A * | 11/1993 | Rosenberg | 514/19 |
| 5,719,296 A | 2/1998 | Acton, III et al. | |

FOREIGN PATENT DOCUMENTS

| | | |
|---|---|---|
| WO | WO 87/05909 | 10/1987 |
| WO | WO 90/04917 | 5/1990 |
| WO | WO 96/16950 | 6/1996 |
| WO | WO 97/16425 | 5/1997 |
| WO | WO 01/07407 | 2/2001 |
| WO | WO 2004/013098 | 2/2004 |
| WO | WO 2004/043916 | 5/2004 |

OTHER PUBLICATIONS

Hussain, I. et al., "Identification of a Novel Aspartic Protease (Asp 2) as β-Secretase", *Mol. Cell. Neurosci*, (1999) 14: 419-427.

Lin, X. et al., "Human aspartic protease memapsin 2 cleaves the β-secretase site of β-amyloid precursor protein", Proceedings of the National Academy of Sciences of the USA, (2000) 97: 1456-1460.
Luo, Y., et al., "Mice deficient in BACE1, the Alzheimer's β-secretase, have normal phenotype and abolished β-amyloid generation", *Nature Neuroscience* (2001) 4: 231-232.
Martin, J. L. et al., "Molecular Recognition of Macrocyclic Peptidomimetic Inhibitors by HIV-1 Protease", *Biochemistry* (1999) 38: 7978-7988.
Roberds, S.L. et al.,"BACE knockout mice are healthy despite lacking the primary β-secretase activity in brain: implications for Alzheimer's disease therapeutics", *Human Molecular Genetics* (2001) 10: 1317-1324.
Seiffert, D.; et al., "Presenilin-1 and -2 are molecular targets for γ-secretase inhibitors", *J. Biol. Chem*. (2000) 275, 34086-34091.
Selkoe, D. J., "Alzheimer's Disease: Genes, Proteins, and Therapy", *Physiol. Rev*. (2001) 81, 741-766.
Selkoe, D. J., "Biochemical Analyses of Alzheimer's Brain Lesions lead to the Identification of αβ and its Precursor", *Ann. Rev. Cell Biol.* (1994) 10: 374-403.
Sinha, S., et al., "Purification and cloning of amyloid precursor protein β-secretase from human brain", *Nature* (London) (1999) 402: 537-540.
Thaisrivongs, S. et al., "Conformationally Constrained Renin Inhibitory Peptides: γ-Lactam-Bridged Dipeptide Isostere as Conformational Restrictions", *J. Med. Chem*. (1988) 31: 1369-1376.
Thaisrivongs, et al., "Renin inhibitory peptides: a study of structural modifications in the peptide backbone", *J. Hypertension* (1989), 7 Suppl. 2: S21-S23.
Thal, D. R., et al., "Two types of Sporadic Cerebral Amyloid Angiopathy", *J. Neuropath. and Exper. Neurology* (2002) 61: 282-293.
Vassar, R., et al., "β-Secretase cleavage of Alzheimer's amyloid precursor protein by the transmembrane aspartic protease BACE", *Science* (1999) 286: 735-741.
Walsh, D. M., et al., "Naturally secreted oligomers of amyloid β protein potently inhibit hippocampal long-term potentiation in vivo", *Nature* (2002) 416, 535-539.
Wolfe, M. S., "Secretase Targets for Alzheimer's Disease: Identification and Therapeutic Potential", *J. Med. Chem*. (2001) 44, 2039-2060.
Yan, R. et al., "Membrane-anchored aspartyl protease with Alzheimer's disease β-secretase activity", *Nature* (1999) 402: 533-537.

* cited by examiner

*Primary Examiner*—Golam M Shameem
(74) *Attorney, Agent, or Firm*—Aldo A. Algieri

(57) ABSTRACT

There is provided a series of novel substituted gamma-lactams of Formula (I)

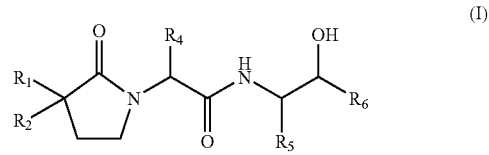

or a stereoisomer; or a pharmaceutically acceptable salt thereof, wherein $R_1$, $R_2$, $R_4$, $R_5$ and $R_6$ as defined herein, their pharmaceutical compositions and methods of use. These novel compounds inhibit the processing of amyloid precursor protein (APP) by β-secretase and, more specifically, inhibit the production of Aβ-peptide. The present disclosure is directed to compounds useful in the treatment of neurological disorders related to β-amyloid production, such as Alzheimer's disease and other conditions affected by anti-amyloid activity.

8 Claims, No Drawings

GAMMA-LACTAMS AS BETA-SECRETASE INHIBITORS

CROSS-REFERENCE TO RELATED APPLICATIONS

This is a non-provisional application which claims the benefit of U.S. Provisional Applications U.S. Ser. No. 60/604,624 filed Aug. 26, 2004 and U.S. Ser. No. 60/660,433 filed Mar. 10, 2005.

FIELD OF THE DISCLOSURE

This patent application provides novel substituted gamma-lactam compounds having drug and bio-affecting properties, their pharmaceutical compositions and method of use. In particular, the disclosure is concerned with a series of novel gamma-lactams which are inhibitors of the β-amyloid peptide (β-AP) production, thereby acting to prevent the accumulation of amyloid protein deposits in the brain and, therefore, are useful in the treatment of neurological disorders related to β-amyloid production. More particularly, the present disclosure relates to the treatment of Alzheimer's Disease (AD) and similar diseases.

BACKGROUND

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J. *Ann. Rev. Cell Biol.*, 1994, 10: 373-403).

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as A=. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP) (Selkoe, D. *Physiol. Rev.* 2001, 81, 741-766; Wolfe, M. *J. Med. Chem.* 2001, 44, 2039-2060). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D.; Bradley, J. et al., *J. Biol. Chem.* 2000, 275, 34086-34091).

In addition to AD, excess production and/or reduced clearance of Aβ causes cerebral amyloid angiopathy (CAA) (reviewed in Thal, D., Gherbremedhin, E. et al., *J. Neuropath. Exp. Neuro.* 2002, 61, 282-293). In these patients, vascular amyloid deposits cause degeneration of vessel walls and aneurysms that may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

A logical approach to reducing Aβ levels is to interfere with the action of the secretases that are directly involved in the cleavage of APP to Aβ. The β-secretase enzyme (BACE) is responsible for cleaving APP and forms the amino-terminus of Aβ, initiating the amyloidogenic pathway. The BACE enzyme is a transmembrane aspartyl protease and was described in the literature by several independent groups [see Hussain, I. et al., (1999) *Mol. Cell. Neurosci.*, 14: 419-427; Lin, X. et al., (2000) *Proceedings of the National Academy of Sciences of the United States of America*, 97: 1456-1460; Sinha, S., et al, (1999) *Nature* (London), 402: 537-540; Vassar, R., et al., (1999) *Science* (Washington, D.C.), 286: 735-741; Walsh, D. M. et al, (2002); Wolfe, M. S. (2001); Yan, R. et al., (1999) *Nature* (London), 402: 533-537].

Removal of BACE activity in mice by gene targeting completely abolishes Aβ production [see Luo, Y., et al., (2001) *Nature Neuroscience*, 4: 231-232; Roberds, S. L. et al., (2001) *Human Molecular Genetics*, 10: 1317-1324].

BACE −/− mice also show no detectable negative phenotypes, suggesting that disruption of BACE-mediated cleavage of APP does not produce additional undesired effects. This demonstrates that a drug substance capable of inhibiting β-secretase activity should lower or halt the synthesis of Aβ and should provide a safe treatment for Alzheimer's disease.

Published article Martin, J. L. et al., (1999), *Biochemistry*, 38: 7978-7988 discloses macrocyclic inhibitors of the HIV 1 protease.

PCT Publication WO 96/16950, published Jun. 6, 1996, discloses macrocyclic inhibitors of the HIV 1 protease.

PCT Publication WO 01/07407, published Feb. 1, 2001, discloses lactam inhibitors of the hepatitis C virus NS3 protease.

PCT Publication WO 97/16425, published May 9, 1997, and related U.S. Pat. No. 5,719,296 disclose pseudolactam inhibitors of peptide binding to MHC class II receptors.

U.S. Pat. No. 5,120,718 to Goldman et al., granted Jun. 9, 1992, discloses candida acid protease inhibiting compounds.

U.S. Pat. No. 5,164,388 to De et al., granted Nov. 17, 1992, discloses heterocyclic renin inhibitors.

PCT Publication WO 90/04917, published May 17, 1990, and related U.S. Pat. No. 5,164,388 discloses heterocyclic peptide renin inhibitors.

PCT Publication WO 87/05909, published Oct. 8, 1987, and related U.S. Pat. No. 4,705,846 disclose renin inhibitors having a lactam pseudo dipeptide insert.

PCT Publication WO2004/013098, published Feb. 12, 2004, discloses lactam derivatives as beta-secretase inhibitors.

PCT Publication WO 2004/043916, published May 27, 2004, disclose phenylcarboxamides as beta-secretase inhibitors.

Published article Thaisrivongs et al., *J. Hypertension* (1989), Suppl. (2), S21-S23 discusses related renin inhibitors.

Published article Thaisrivongs, S. et al., *J. Med. Chem.* (1988), 31(7): 1369-76 discusses related renin inhibitors.

At present there remains an urgent need to develop pharmaceutical agents capable for effective treatment in halting, slowing, preventing, and/or reversing the progression of Alzheimer's disease. Compounds that are effective inhibitors of beta-secretase, that inhibit beta-secretase mediated cleavage of APP, that are effective inhibitors of Aβ protein production by beta-secretase, and/or are effective in reducing soluble Aβ protein, amyloid beta deposits or amyloid beta plaques, are needed for effective treatment in halting, slowing, preventing, and/or reversing neurological disorders related to Aβ protein production, such as Alzheimer's disease.

SUMMARY OF THE DISCLOSURE

A series of gamma-lactam derivatives having the Formula (I)

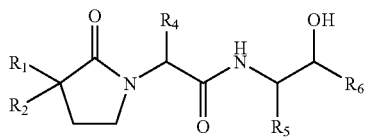

(I)

or a stereoisomer; or a pharmaceutically acceptable salt thereof, wherein $R_1$, $R_2$, $R_4$, $R_5$ and $R_6$ as defined below are effective inhibitors of the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds or a pharmaceutical composition containing a therapeutically effective amount of at least one of these compounds to patients suffering from, or susceptible to, these conditions involves reducing β-AP available for accumulation and deposition in brains of these patients.

DETAILED DESCRIPTION

The present application comprises compounds of Formula I, their pharmaceutical formulations, and their use in inhibiting β-AP production in patients suffering from or susceptible to AD or other disorders resulting from β-AP accumulation in brain tissue. The compounds of Formula I which include stereoisomers and pharmaceutically acceptable salts thereof have the following formula and meanings:

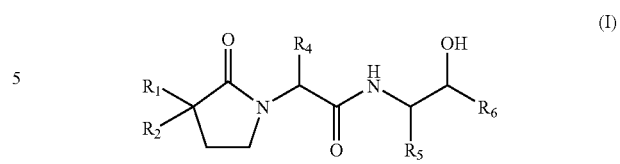

(I)

wherein $R_1$ is hydrogen, $C_{1-6}$alkyl or $NHR_3$;

$R_2$ is $C_{1-6}$alkyl, $C_{3-6}$alkenyl, $C_{3-6}$cycloalkyl or $C_{3-6}$cycloalkyl($C_{1-4}$alkyl) in which each group is optionally substituted with a group selected from halogen, $CF_3$, $CF_2H$, OH, $OCF_3$ and $C_{1-4}$alkoxy;

$R_3$ is —C(=O)$R_{10}$, —C(=O)O$R_{10}$, —C(=O)NH$R_{10}$, —S(O)$_n R_{10}$ or $C_{1-6}$alkyl optionally substituted with a group selected from $C_{3-6}$cycloalkyl, halogen, $CF_3$, $OCF_3$, OH, $C_{1-4}$alkoxy and CN;

$R_4$ is $C_{1-6}$alkyl, $C_{3-6}$cycloalkyl, $C_{3-6}$cycloalkyl($C_{1-4}$alkyl), phenyl or phenyl($C_{1-4}$alkyl) in which each group is optionally substituted with the group selected from halogen, $C_{1-4}$alkyl, OH, $C_{1-4}$alkoxy, $CF_3$, $CF_2H$, $OCF_3$ and CN;

$R_5$ is $C_{1-6}$alkyl, phenyl or phenyl($C_{1-4}$alkyl) in which each group is optionally substituted with one or two groups selected from halogen, $C_{1-4}$alkyl, OH, $CF_3$, $OCF_3$ and CN;

$R_6$ is

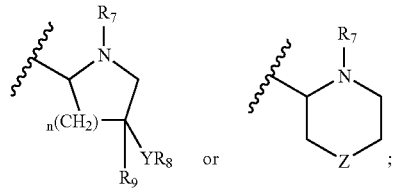

$R_7$ is hydrogen or $C_{1-4}$alkyl;

n is 1 or 2;

Y is O, $NR_7$ or $S(O)_n$;

Z is $CH_2$, O or S;

$R_8$ and $R_9$ each are independently hydrogen, $C_{1-4}$alkyl, $C_{3-6}$alkenyl, $C_{3-6}$alkynyl, phenyl or pyridyl in which said phenyl and pyridyl are optionally substituted with $C_{1-4}$alkyl, fluoro$C_{1-4}$alkyl, $C_{1-4}$alkoxy, halogen or CN; or $YR_8$ and $R_9$ are joined together with the carbon to which they are attached to form a 5- or 6-membered ring wherein Y is oxygen, and $R_8$ and $R_9$ are —$CH_2(CH_2)_n$—O—; and $R_{10}$ is $C_{1-4}$alkyl optionally substituted with the group selected from halogen, OH, $CF_3$, $NH_2$ and $C_{1-4}$alkoxy.

The present application also provides a method for the treatment or alleviation of disorders associated with β-amyloid peptide, especially Alzheimer's Disease, cerebral amyloid angiopathy and Down's Syndrome, which comprises administering together with a conventional adjuvant, carrier or diluent a therapeutically effective amount of a compound of Formula (I) or a pharmaceutically acceptable salt thereof.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Colin Dingwall, *Journal of Clinical Investigation*, November 2001, 108 (9): 1243-1246; as well as PCT international patent application WO 01/92235, published Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The term "substituted," as used herein and in the claims, means that any one or more hydrogens on the designated atom is replaced with a selection from the indicated group, provided that the designated atom's normal valency is not exceeded, and that the substitution results in a stable compound.

As used herein and in the claims, "alkyl" or "alkylene" is intended to include both branched and straight-chain saturated aliphatic hydrocarbon groups having the specified number of carbon atoms; for example, "$C_{1-6}$ alkyl" and "$C_{1-10}$ alkyl" denotes alkyl having 1 to 6 or 1 to 10 carbon atoms. Examples of alkyl include, but are not limited to, methyl, ethyl, n-propyl, i-propyl, n-butyl, i-butyl, sec-butyl, t-butyl, pentyl, hexyl, octyl and decyl. Preferred "alkyl" group, unless otherwise specified, is "$C_{1-4}$ alkyl". Additionally, unless otherwise specified, "propyl" denotes n-propyl or i-propyl; "butyl" denotes n-butyl, i-butyl, sec-butyl, or t-butyl.

As used herein and in the claims, "alkenyl" or "alkenylene" is intended to include hydrocarbon chains of either a straight or branched configuration and one or more unsaturated carbon-carbon bonds which may occur in any stable point along the chain, for example, "$C_{2-6}$ alkenyl" include but are not limited to ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein and in the claims, "alkynyl" or "alkynylene" is intended to include hydrocarbon chains of either a straight or branched configuration and one or more carbon-carbon triple bonds which may occur in any stable point along the chain, for example, "$C_{2-6}$ alkynyl" include but not limited to ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

As used herein and in the claims, "halogen" refers to fluoro, chloro, bromo, and iodo. Unless otherwise specified, preferred halogens are fluoro and chloro. "Counterion" is used to represent a small, negatively charged species such as chloride, bromide, hydroxide, acetate, sulfate, and the like.

"Cycloalkyl" is intended to include saturated ring groups, having the specified number of carbon atoms. For example, "$C_{3-6}$ cycloalkyl" denotes such as cyclopropyl, cyclobutyl, cyclopentyl and cyclohexyl.

The compounds described herein may have asymmetric centers. An example of a preferred stereochemical configuration is the isomer:

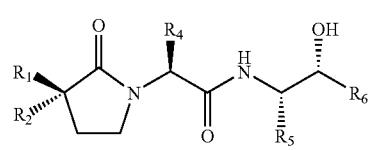

(Ia)

or pharmaceutically acceptable salt thereof, but is not intended to be limited to this example. It is understood, that whether a chiral center in an isomer is "R" or "S" depends on the chemical nature of the substituents of the chiral center. All configurations of compounds of the invention are considered part of the invention. Additionally, the carbon atom to which $R_1$ and $R_2$ is attached may describe a chiral carbon. Compounds of the present disclosure containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

In the method of the present application, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

The compounds of the present application can be prepared in a number of ways well known to one skilled in the art of organic synthesis. The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In general, the present compounds represented by Formula I (General Reaction Scheme A) can be prepared by coupling, under standard conditions known to one skilled in the art, a substituted γ-lactam 2 and a substituted tetrahydroisoquinoline hydroxyethyl amine. Methods for the synthesis of γ-lactams 2 are known in the art and are disclosed in a number of references including but not limited to those given below. The synthesis of substituted tetrahydroisoquinoline hydroxyethyl amines is novel and is disclosed in detail in the discussion given below.

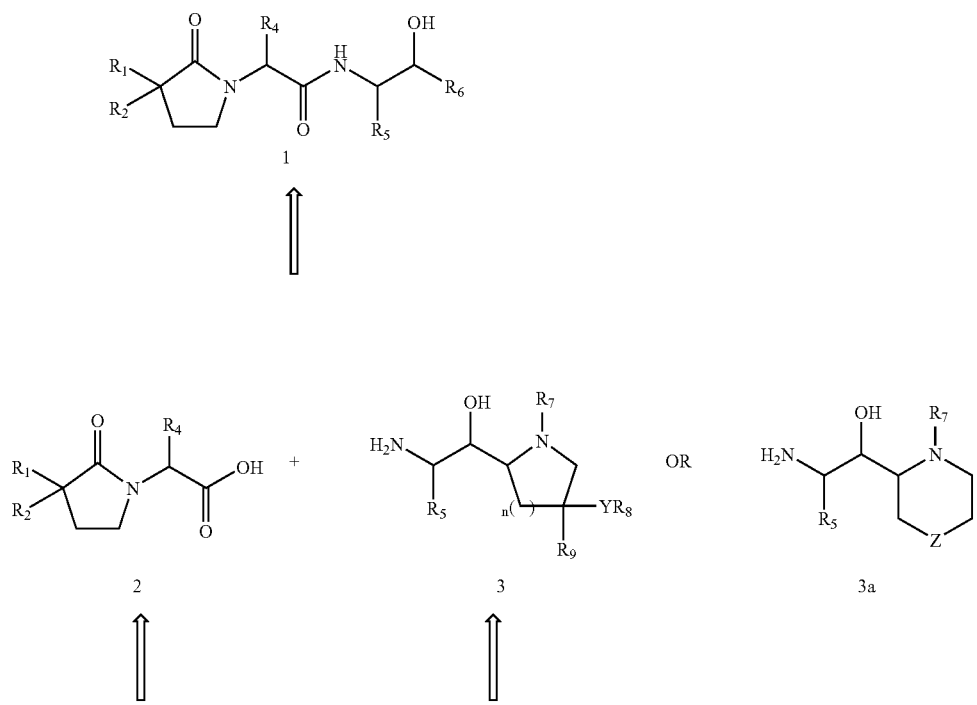

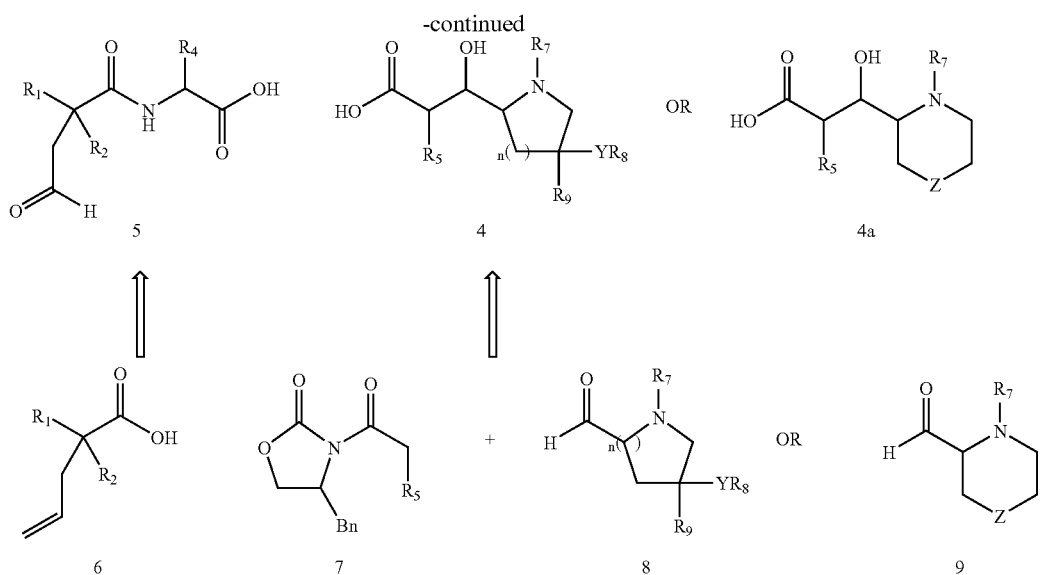

A preferred subset of lactams of formula 2 are represented by formula 2a and are known as

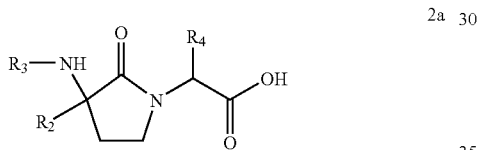

disubstituted γ-lactams. Disubstituted γ-lactams 2 can be prepared by cyclization of an aldehyde-containing dipeptide precursor 5 followed by deprotection of the amino group and functionalization with a suitable reaction partner, such as a carboxylic acid or an activated derivative thereof, a sulfonyl halide, isocyanate, or chloroformate. Alternatively, the amino group can be alkylated under standard conditons known to one skilled in the art, for example, using an aldehyde and a reducing agent such as sodium borohydride or derivatives thereof. The dipeptide precursor 5 is prepared by coupling a natural or unnatural amino acid ester to a quaternary α-allyl amino acid 6, followed by oxidation of the allyl group to the requisite aldehyde and cyclization. Substituted cyclic hydroxyethyl amines are prepared using an aldol reaction of a cyclic aldehyde 8 with a functionalized enolate, followed by Curtius rearrangement of the resulting acid to the amine 3. Further details of the preparation of compounds are provided below.

Synthesis of a substituted quaternary α-allyl amino acid 6 is carried out according to one of several literature methods. Scheme 1 shows the method of Seebach, et. al., (Seebach, D.; Hoffmann, M. *European Journal of Organic Chemistry* 1998, 1337-1351, Hoffmann, M.; Blank, S.; Seebach, D.; Kusters, E.; Schmid, E. *Chirality* 1998, 10, 217-222, Hoffmann, M.; Seebach, D. *Chimia* 1997, 51, 90-92, Blank, S.; Seebach, D. *Angew. Chem.* 1993, 105, 1780-1781 (See also Angew. Chem., Int. Ed. Engl., 1993, 1732(1712), 1765-1786), where (R)- or (S)-tert-butyl 2-tert-butyl-4-methoxy-2,5-dihydro-1, 3-imidazole-1-carboxylate 10 is alkylated sequentially with allyl iodide and a $R_1$-group electrophile (which can be suitably protected by one skilled in the art if necessary) to provide a protected amino acid equivalent with high diastereoselectivity.

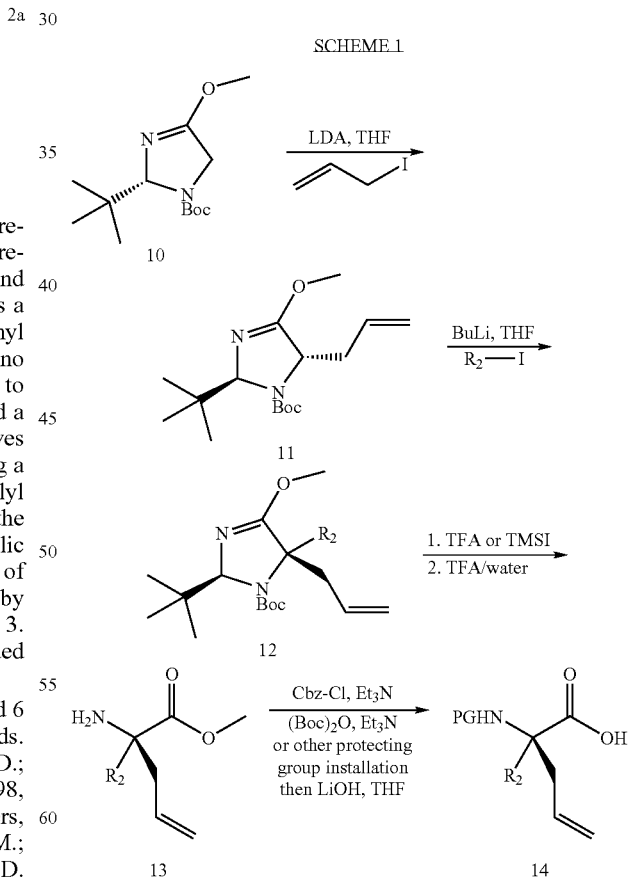

The scalemic amino acid is then generated by deprotection of the Boc group and acidic deprotection of the trimethylacetyl acetal. The resulting amino acid methyl ester 13 can then be protected under standard conditions with protecting groups well known to those skilled in the art, such as t-butyloxycarbonyl (Boc) or benzyloxycarbonyl (Cbz), and saponified to the free carboxylic acid 14.

Alternatively, quaternary amino acids can be synthesized from the corresponding amino acid (Scheme 2). Using isoleucine as an example, formation of the benzylidene imine followed by cyclization with benzyloxycarbonyl chloride provides a protected amino acid precursor 17 (Seebach, D.; Fadel, A. *Helv. Chim. Acta.* 1985, 68, 1243 and Altmann, E.; Nebel, K.; Muffer, M. *Helv. Chim, Acta* 1991, 74, 800; De, B.; Dellaria, J. F.; Baker, W. R.; Zydowsky, T. M.; Rosenberg, S. H. et al., EP 365992, 1990). Alkylation with allyl bromide or iodide provides the alkylated lactone 18 which can be deprotected under basic conditions to provide the protected amino acid derivative 19 which can be directly coupled as is shown in Scheme 5.

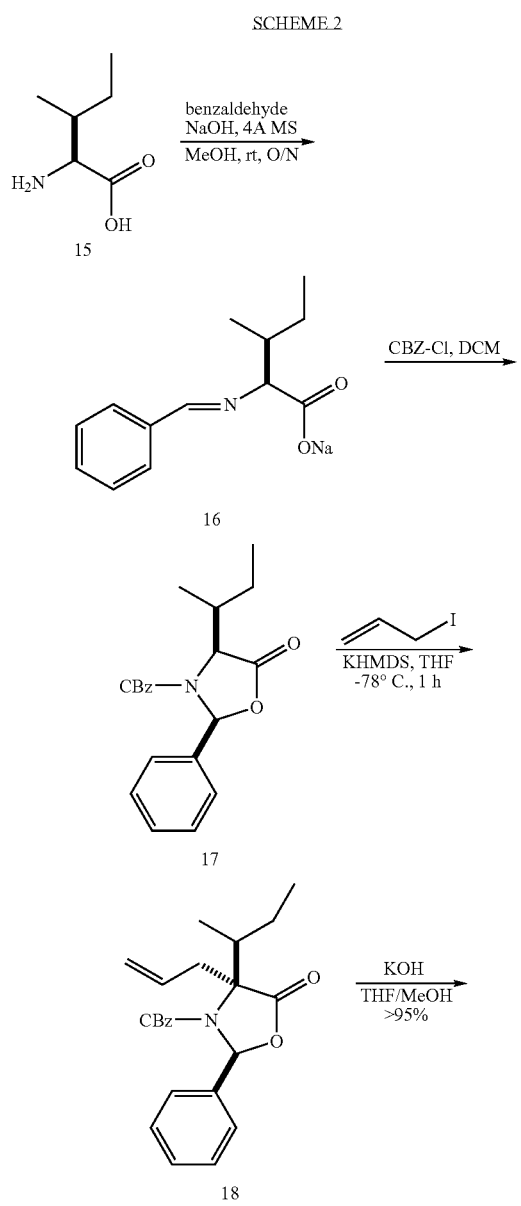

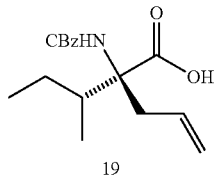

An additional method for the preparation of quaternary amino acids is shown in Scheme 3. Treatment of an amino acid 20 with allyl bromide in the present of $Cs_2CO_3$ provides the amino acid allylic ester 21. Ester enolate Caisen rearrangement of 21 results in 22 (Kazmaier, U. and Maier, S. *Tetrahedron* 1996, 52, 941).

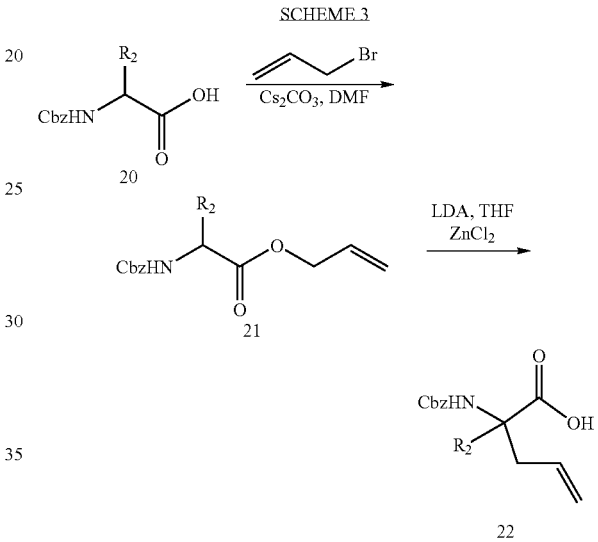

Amino acids used as the starting materials in the chemistry reported herein can be natural or unnatural. Many are available as items of commerce in suitably protected form, or unprotected where protecting groups can be installed under standard conditions to one skilled in the art. Additional methods for the preparation of unnatural amino include the Strecker synthesis or amidomalonate synthesis. In addition, the Myers pseudoephedrine glycinamide alkylation method (Myers, A. G.; Gleason, J. L.; Yoon, T.; Kung, D. W. *J. Am. Chem. Soc.* 1997, 119, 656-673), Schollkopf stereoselective alkylation (Schollkoft, U.; Hartwig, W.; Groth, U. *Angew. Chem. Int. Ed. Engl.* 1979, 18, 863), and Evans electrophilic azidation (Evans, D. A.; Britton, T. C.; Ellman, J. A.; Dorow, R. L. *J. Am. Chem. Soc.* 1990, 112, 4011) may be used to prepare natural or unnatural amino acids in enantionmerically pure form.

A specific example of the production of substituted homophenylalanine derivatives related to compound 30 can be prepared using the chemistry shown in Scheme 4. Commercial Boc-aspartic acid benzyl ester can be reduced through the intermediate succinimide ester to produce the alcohol 25. Iodination followed by formation of the alkyl zinc iodide and Negishi-type coupling under palladium catalysis produces substituted, protected homophenylalanines 27 which can be deprotected in the standard manner using trifluoroacetic acid or HCl to produce indermediates 28, useful in the formation of substituted lactams of type 33.

SCHEME 4

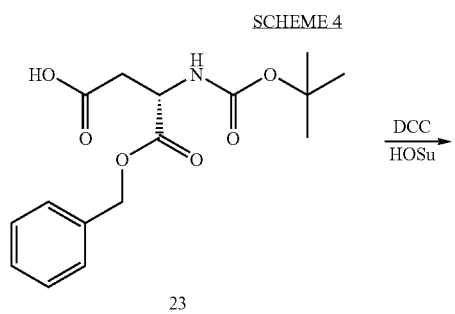

23

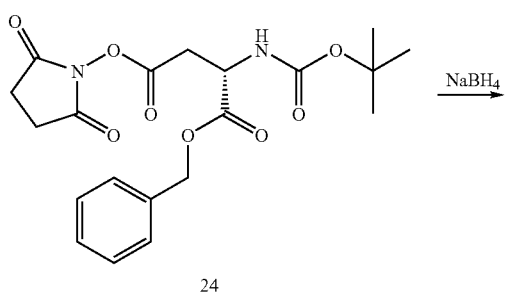

24

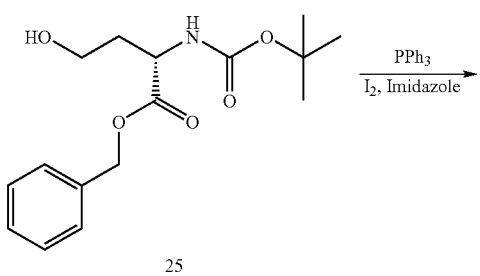

25

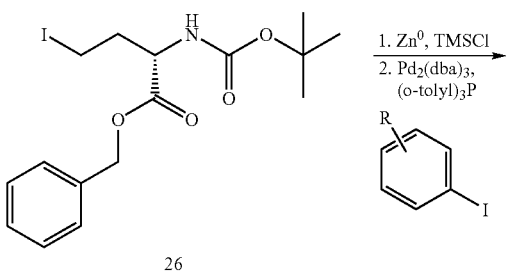

26

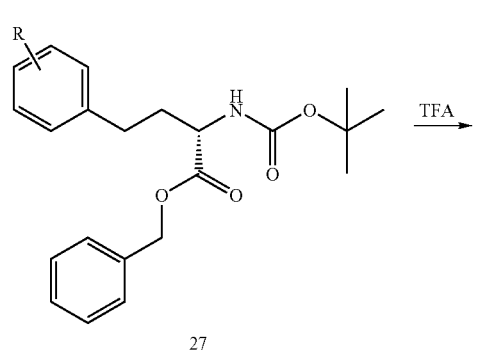

27

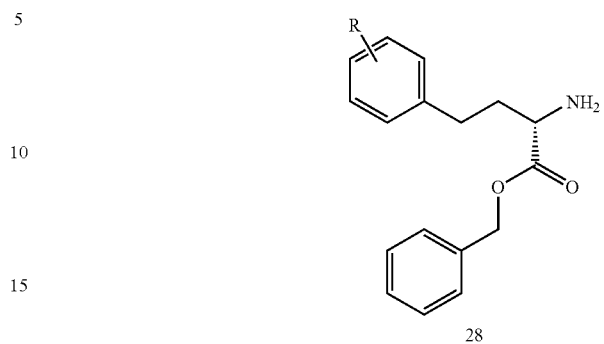

28

A quaternary amino acid 29 may then be coupled under standard conditions to a natural or unnatural amino acid ester using standard coupling reagents like HATU (O-(7-azabenzotriazol-1-yl)-1,1,3,3,-tetramethyluronium hexafluorophosphate) or PyBOP (benzotriazole-1-yl-oxy-tris-pyrrolidino-phosphonium hexafluorophosphate) in the presence of a tertiary amine base such as triethylamine, N,N-diisopropylethylamine, or N-methylmorpholine (Scheme 5). Oxidation of the allyl group using oxonolysis or osmium tetroxide/sodium periodate gives the aldehyde which is cyclized to the γ-lactam 33 using trietthylsilane and trifluoroacetic acid (Holladay, M. W.; Nadzan, A. M. *J. Org. Chem.* 1991, 56, 3900-3905; Duan, J. PCT International Publication WO 0059285, 2000.

SCHEME 5

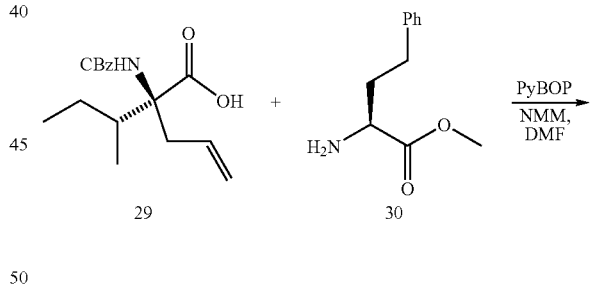

29   30

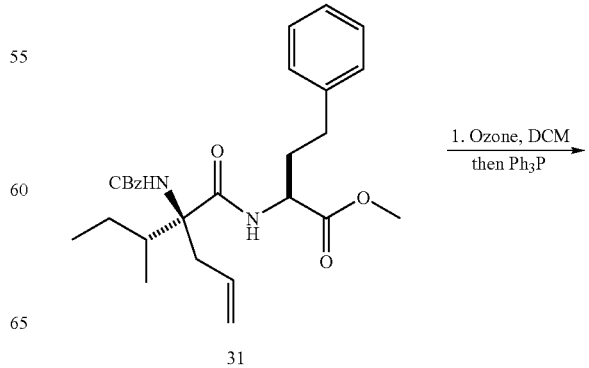

31

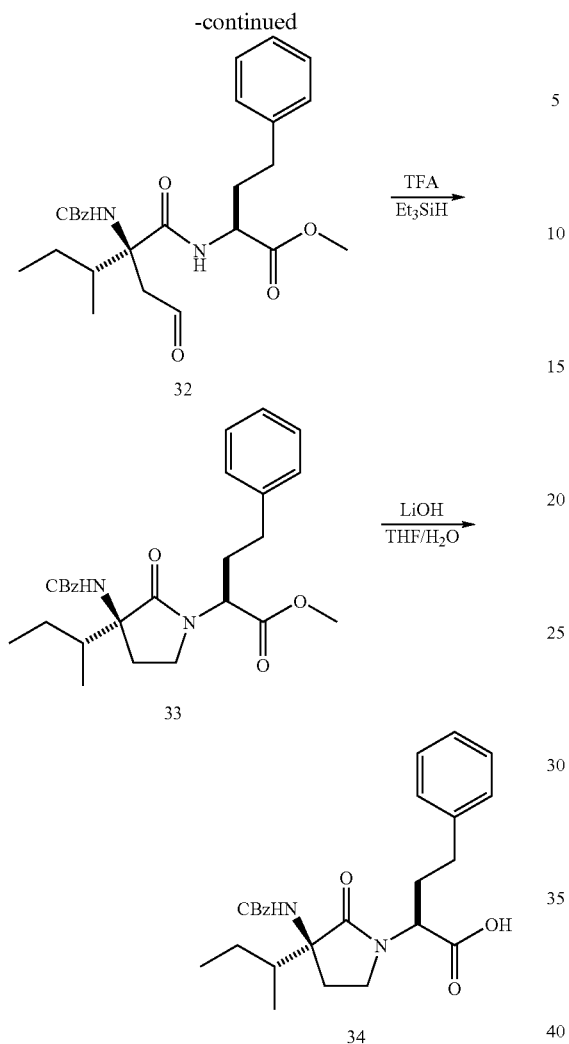

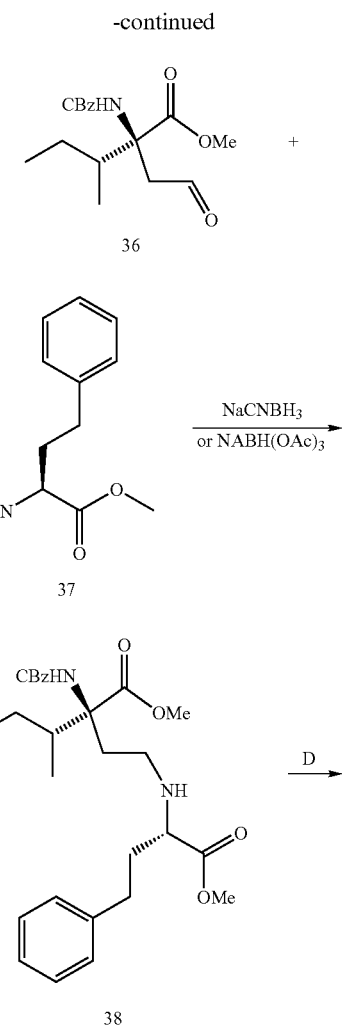

Cleavage of the amino acid ester using saponification conditions such as lithium or sodium hydroxide in aqueous solution provides the protected lactam 34 for coupling to the diaminopropane fragment.

Lactams may also be synthesized in the manner demonstrated in Scheme 6, where the quaternary amino acid is directly oxidized to the aldehyde, and a second amino acid ester is introduced by reductive alkylation using a reducing agent such as sodium borohydrode, sodium triacetoxyborohydride, or sodium cyanoborohydride to produce an amine 38. The product can then be cyclized directly to form the desired γ-lactam (see, for instance, Scheidt, K. A.; Roush, W. R.; McKerrow, J. H.; Selzer, P. M.; Hansell, E.; Rosenthal, P. J. *Bioorganic & Medicinal Chemistry* 1998, 6, 2477-2494.

SCHEME 6

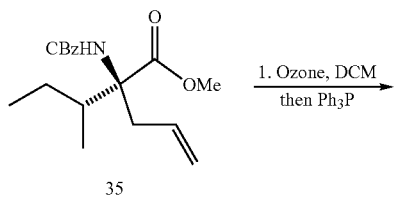

The lactam amine protecting group may now be removed by catalytic hydrogenation or other suitable methods (Scheme 7), and the primary amine center may be further functionalized by reacting with agents such as carboxylic acids or their activated variants such as acid chlorides or acid anhydrides to make amides such as 42. A number of other derivatives 42 can be prepared, including but not limited to the reaction with sulfonic acids or sulfonyl halides to prepare sulfonamides, chloroformates to provide carbamates, or carbamoyl chlorides or isocyanates to provide ureas. Saponification of the methyl ester of these derivatives provides the carboxylic acid 43 ready to couple to the cyclic diaminopropane fragment in protected or unprotected form.

SCHEME 7

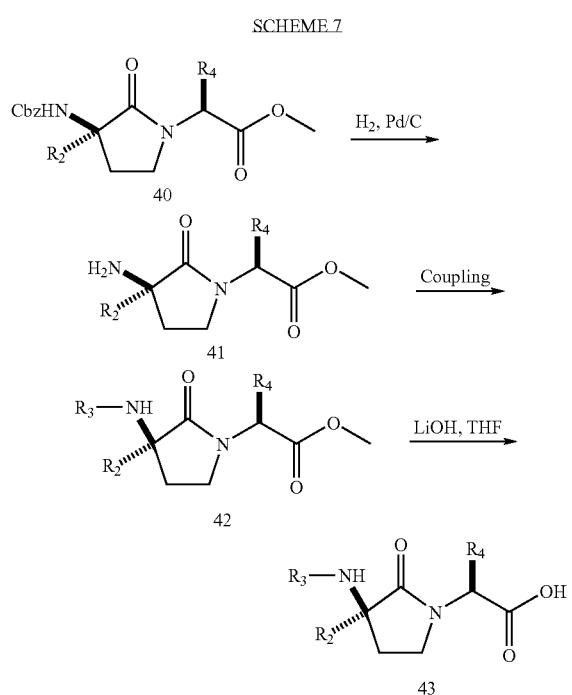

Another preferred subset of lactams of formula 2 are represented by formula 49 (Scheme 8) and are known as monosubstituted γ-lactams. A variety of alpha-allyl carboxylic acids 46 are available utilizing known asymmetric alkylation methodology (for a review, see: Jones, S. *J. Chem. Soc. Perkins I* (2002), 1-21.). Evan's asymmetric alkylation methodology employing N-acycloxazolidinones has proven particularly useful to prepare these alpha-allyl acids [(a) Munoz, L. et. al. *J. Org. Chem.* (2001), 66, 4206. (b) Evans, D. A. et. al. *J. Org. Chem.* (1999), 64, 6411.], and the products so obtained can be reacted in a similar manner as the quaternary amino acids as outlined in Scheme 5 to form the appropriate lactams 49.

SCHEME 8

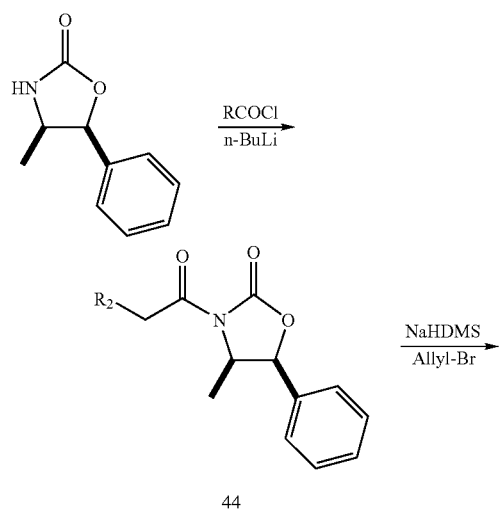

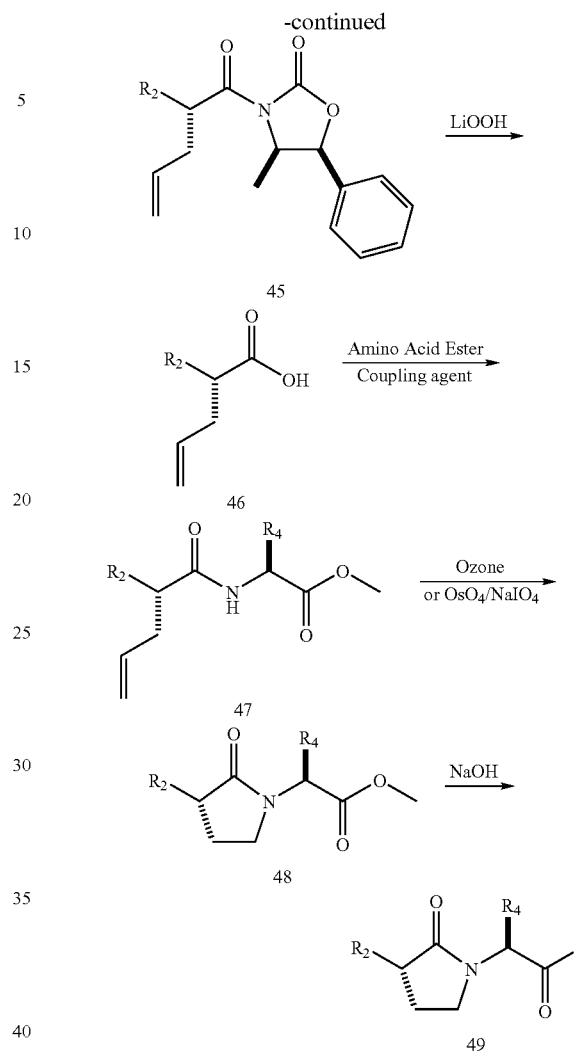

Scheme 11 discloses methods for preparing substituted cyclic hydroxyethyl amines of type 68 that are used as a coupling partner for lactam acids 49 or 43. The method relies on the diastereoselective aldol reaction of a suitable enolate equivalent with a substituted cyclic aldehyde. There are a number of methods for the diastereoselective aldol reaction, including those developed by Masamune, (See, for instance, Masamune, S.; Ali, S. A.; Snitman, D. L.; Garvey, D. S. Aldol condensation with increased stereoselectivity through use of an enantioselective chiral enolate. *Angewandte Chemie* 1980, 92, 573-575, and Masamune, S.; Choy, W.; Kerdesky Francis, A. J.; Imperiali, B. Stereoselective aldol condensation. Use of chiral boron enolates. *Journal of the American Chemical Society* 1981, 103, 1566-1568.) and Heathcock (See Heathcock, C. H. Acyclic stereoselection via the aldol condensation. *ACS Symposium Series* 1982, 185, 55-72, Pirrung, M. C.; Heathcock, C. H. Acyclic stereoselection. A new class of reagents for the highly stereoselective preparation of threo-2-alkyl-3-hydroxycarboxylic acids by the aldol condensation. *Journal of Organic Chemistry* 1980, 45, 1727-1728.). The most commonly used method, and the one described herein, is the method of Evans, reported in a large number of articles including Gage, J. R.; Evans, D. A. Diastereoselective aldol condensation using a chiral oxazolidinone auxiliary. *Organic Syntheses* 1990, 68, 83-91.

Cyclic aldehydes can be prepared by a number of methods known to one skilled in the art depending on the cyclic structure employed. A preferred class of cyclic aldehydes can be derived from derivitization of an appropriate commercially-available diastereomer of 4-hydroxy pro line. The hydroxy proline acids may be protected using standard conditions know to those skilled in the art. In general, nitrogen atom can be blocked by such protecting groups as Boc or benzyl, the alcohol protected as allyl, benzyl, or other appropriate group, and the carboxylic acid may then be reduced under standard conditions to the alcohol (Scheme 9). Ways to effect this transformation include sodium borohydride reduction of the carboxyanhydride, lithium aluminum hydride, or formation of the ester followed by borohydride reduction. The alcohol is then oxidized using a mild oxidizing agent such as the Swem protocol or the Dess-Mertin reagent, or other similar reagents to the desired protected pyrrolidinol aldehyde.

SCHEME 9

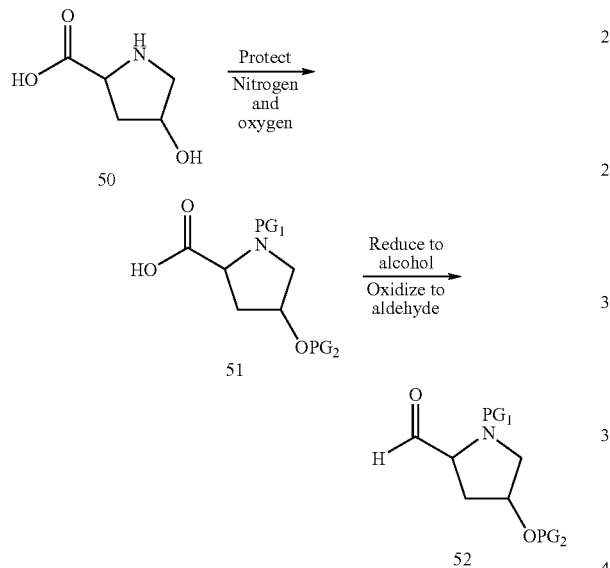

Using similar chemistry, additional substituted aldehydes can be constructed, including the aldehydes derived from pipecolic acid, morpholine 3-carboxylic acid, or thiomorpholine carboxylic acid, all items of commerce, according to Scheme 10. Typically the nitrogen protecting group is a Boc group.

SCHEME 10

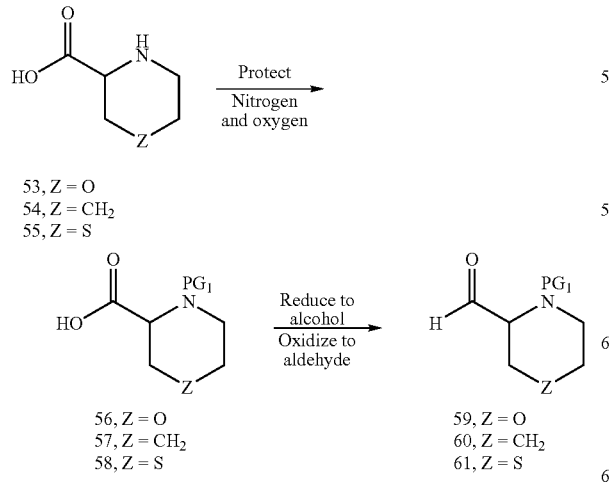

The protected cyclic aldehyde is then reacted with an enolate according to the method of Evans as referenced below (Scheme 11). Thus, (S)-4-benzyl-2-oxazolidinone is acylated as it's lithium salt with a carboxylic acid chloride or with the carboxylate activated as it's pivaloyl mixed carboxyanhydride (see Ho, G.-J.; Mathre, D. J. Lithium-Initiated Imide Formation. A Simple Method for N-Acylation of 2-Oxazolidinones and Bornane-2,10-Sultam. *Journal of Organic Chemistry* 1995, 60, 2271-2273). to provide the substituted N-Acyl oxazolidinone 63. This reagent is deprotonated using dibutylboron triflate and a tertiary amine base such as diisopropylethylamine to form the boron enolate, which reacts in a diastereoselective manner to produce the β-hydroxyimide 65. Saponification of the Chiral auxiliary under standard conditions (LiOH, $H_2O_2$) followed by Curtius rearrangement initiated by formation of the acyl azide using diphenylphosphorylazide (DPPA) provides the carbamate-protected aminoalcohol 66. Alternatively, the acid can be converted to the acyl azide using an acid activating agent such as the mixed carbonic anhydride formed by isobutyl chloroformate in the presence of an amine base such as N-methyl morpholine followed by treatment with sodium azide. The rearrangement is then cleanly effected by heating the acyl azide in a solvent such as toluene. Removal of the alcohol protecting group provides the free alcohol, which may be carried forward itself, or serve as a synthon for other functionality.

SCHEME 11

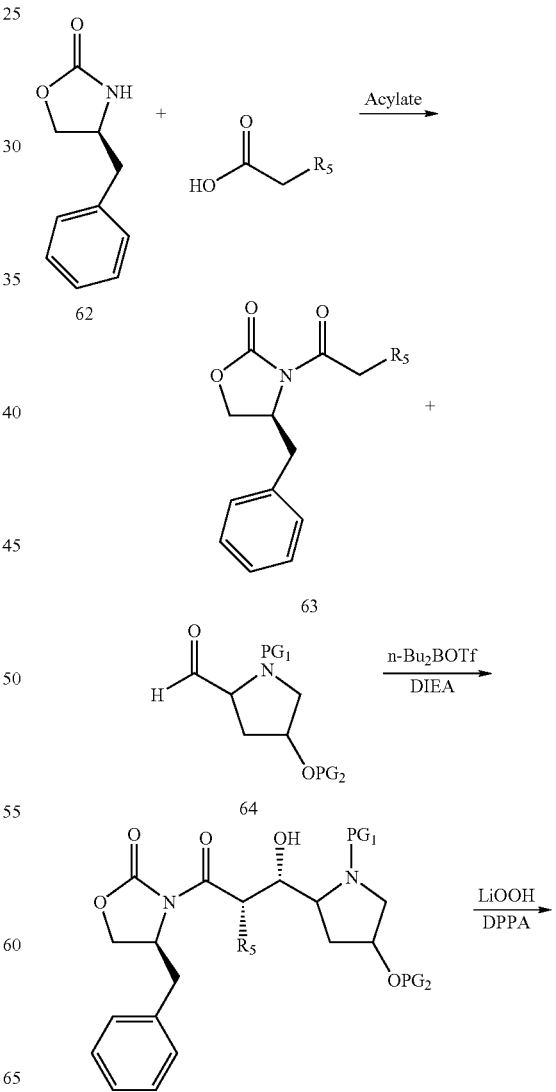

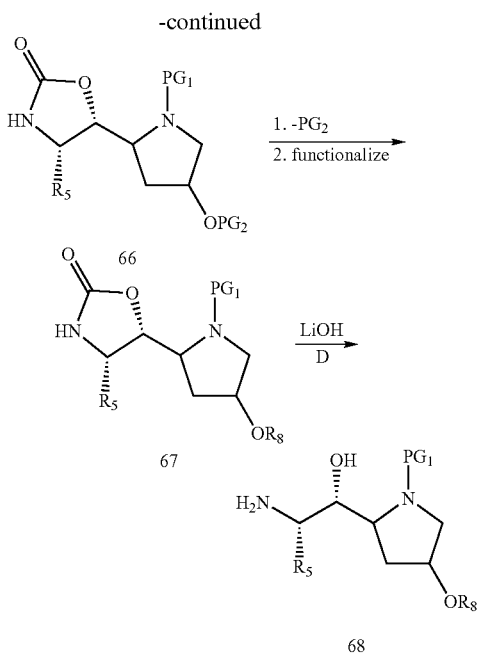

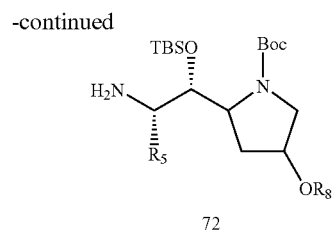

In a preferred embodiment of the chemistry, the intermediate 69 is prepared where $PG_1$=Boc and $PG_2$=Allyl. This intermediate can be further blocked on the remaining alcohol using TBS triflate/lutidine, and rearrangement using DPPA in the presence of benzyl alcohol provides the tetraprotected intermediate 70. The pyrrolidine alcohol is unmasked using Wilkinson's catalyst to prepare the vinyl ether followed by oxidative cleavage with $KMnO_4$, and the resulting alcohol can be functionalized as above, including chemistry such as Mitsunobu reactions to install aryl ethers, alkylations, and oxidation to the ketone followed by reactions such as anion additions and Wittig olefinations.

Coupling of a lactam acid 73 with a protected or unprotected amino alcohol 74 using methods previously described for making amide bonds, such as HATU and DIEA in DMF, provides a protected or unprotected product, which can be deprotected if necessary to provide the compounds of formula Ia an embodiment of the present invention (Scheme 13). Preferably, if a protecting group X is used, it is a Boc group, which is removed by treatment with trifluoroacetic acid in dichloromethane. Also preferred is cleavage of a p-methoxybenzyl or benzhydryl group using hydrogenation in the usual manner.

For example, Mitsonobu inversion with desired phenols and the like provide O-aryl derivatives, O-alkylation provides ether analogs, oxidation to the ketone and Wittig or anion addition chemistry provides alkenes and arenes after reduction, substituted alkanes, and other transformations known to those skilled in the art. Cleavage of the carbamate by saponification with aqueous lithium hydroxide provides the functionalized pyrrolidine-containing diaminopropane 68 ready to couple to a substituted lactam 43 or 49.

SCHEME 12

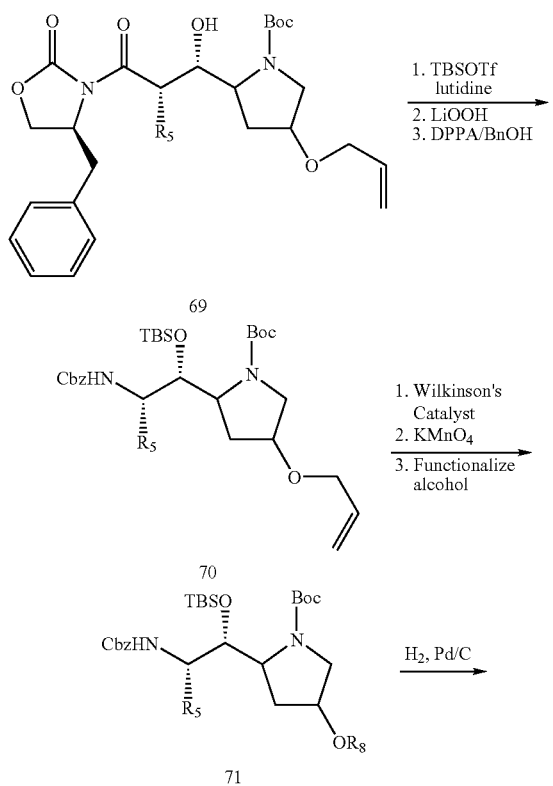

SCHEME 13

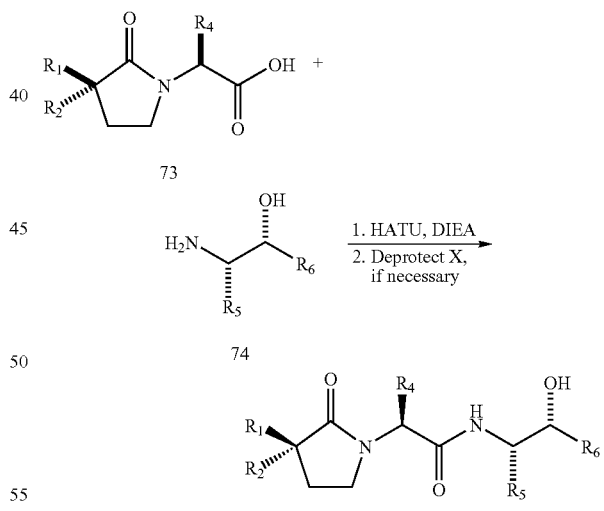

An alternate route to another embodiment of compounds of formula Id is described in Scheme 14. Compound 72 wherein $R_8$=H can be coupled in the usual fashion to lactam acid 73, where upon alcohol functionalization can be effected under the action of a strong base, for example sodium bis(trimethylsilyl)amide, to afford various ethers. The chemistry sequence illustrated for complex substrates using the product 72a and 73 with a range of suitable electrophiles provides a protected or unprotected product, which is deprotected if necessary to provide the compounds of formula Id.

SCHEME 14

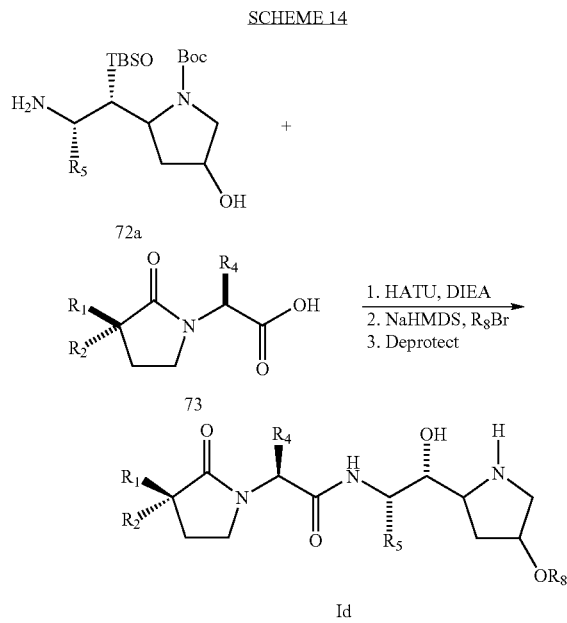

In a preferred embodiment of the invention, the compounds of Formula (Ia) or a stereoisomer thereof have the formula

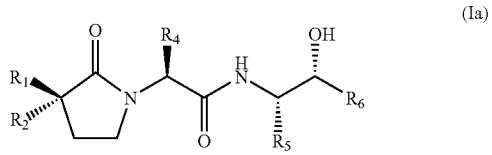

wherein $R_1$ is hydrogen or $NHR_3$; $R_2$ is $C_{1-6}$alkyl or $C_{3-6}$cycloalkyl($C_{1-4}$alkyl) in which each group is optionally substituted with a group selected from halogen, $CF_3$, OH, and $C_{1-4}$alkoxy; $R_3$ is —C(=O)$R_{10}$; $R_4$ is $C_{1-6}$alkyl or phenyl($C_{1-4}$alkyl) in which each group is optionally substituted with the group selected from halogen, $C_{1-4}$alkyl, $C_{1-4}$alkoxy, and $CF_3$; $R_5$ is $C_{1-6}$alkyl, or phenyl($C_{1-4}$alkyl) in which each group is optionally substituted with one or two halogen; $R_6$ is

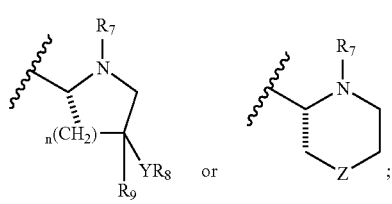

$R_7$ is hydrogen; n is 1; Y is O, NH or $SO_2$; Z is $CH_2$ or O; $R_8$ and $R_9$ each are independently hydrogen, $C_{1-4}$alkyl, $C_{3-6}$alkenyl, phenyl or pyridyl in which said phenyl and pyridyl are optionally substituted with $C_{1-4}$alkyl, fluoro$C_{1-4}$alkyl, $C_{1-4}$alkoxy, halogen or CN; and $R_{10}$ is $C_{1-4}$alkyl optionally substituted with the group selected from OH, $CF_3$, and $C_{1-4}$alkoxy; or a nontoxic pharmaceutically acceptable salt thereof.

In another preferred embodiment of the invention, the compounds of Formula (Ib) have the formula

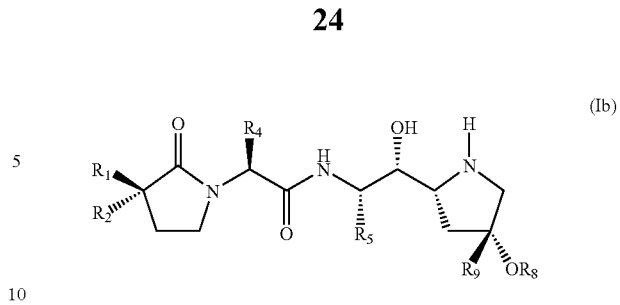

wherein $R_1$ is hydrogen or $NHR_3$; $R_2$ is $C_{1-6}$alkyl or $C_{3-6}$cycloalkyl($C_{1-4}$alkyl) in which each group is optionally substituted with a group selected from $CF_3$, OH, and $C_{1-4}$alkoxy; $R_3$ is —C(=O)$R_{10}$; $R_4$ is $C_{1-6}$alkyl or phenyl($C_{1-4}$alkyl) in which each group is optionally substituted with the group selected from halogen, $C_{1-4}$alkyl, $C_{1-4}$alkoxy, and $CF_3$; $R_5$ is benzyl or 3,5-difluorobenzyl; $R_8$ and $R_9$ each are independently hydrogen, $C_{1-4}$alkyl, $C_{3-6}$alkenyl, phenyl or pyridyl in which said phenyl and pyridyl are optionally substituted with $C_{1-4}$alkyl, fluoro$C_{1-4}$alkyl, $C_{1-4}$alkoxy, halogen or CN; and $R_{10}$ is $C_{1-4}$alkyl optionally substituted with the group selected from OH, $CF_3$, and $C_{1-4}$alkoxy; or a nontoxic pharmaceutically acceptable salt thereof.

In yet another preferred embodiment of the invention, the compounds of Formula (1c) have the formula

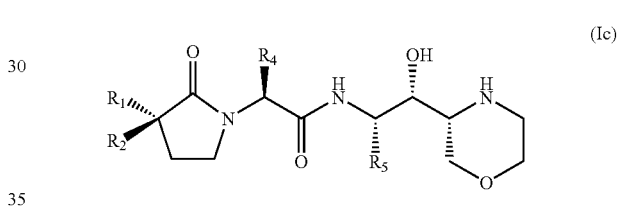

wherein $R_1$ is $C_{1-6}$alkyl or $C_{3-6}$cycloalkyl($C_{1-4}$alkyl) in which each group is optionally substituted with a group selected from $CF_3$, OH, and $C_{1-4}$alkoxy; $R_2$ is hydrogen or $NHR_3$; $R_3$ is —C(=O)$R_{10}$; $R_4$ is $C_{1-6}$alkyl or phenyl($C_{1-4}$alkyl) in which each group is optionally substituted with the group selected from halogen, $C_{1-4}$alkyl, $C_{1-4}$alkoxy, and $CF_3$; $R_5$ is benzyl or 3,5-difluorobenzyl; $R_{10}$ is $C_{1-4}$alkyl optionally substituted with the group selected from OH, $CF_3$, and $C_{1-4}$alkoxy; or a nontoxic pharmaceutically acceptable salt thereof.

Preferred compounds include:
(S)-2-((R)-3-acetamido-3-isobutyl-2-oxopyrrolidin-1-yl)-N-((1R,2S)-3-(3,5-difluorophenyl)-1-hydroxy-1-((2R,4R)-4-propoxypyrrolidin-2-yl)propan-2-yl)-4-phenylbutanamide;
(S)-2-((R)-3-acetamido-3-secbutyl-2-oxopyrrolidin-1-yl)-N-((1R,2S)-3-(3,5-difluorophenyl)-1-hydroxy-1-((2R,4R)-4-propoxypyrrolidin-2-yl)propan-2-yl)-4-phenylbutanamide;
(S)-((1R,2S)-3-(3,5-difluorophenyl)-1-hydroxy-1-((2R,4R)-4-propoxypyrrolidin-2-yl)propan-2-yl) 2-((S)-3-butyl-2-oxopyrrolidin-1-yl)-4-phenylbutanoate;
(S)-((1R,2S)-3-(3,5-difluorophenyl)-1-hydroxy-1-((2R,4R)-4-propoxypyrrolidin-2-yl)propan-2-yl) 2-((S)-3-butyl-2-oxopyrrolidin-1-yl)propanoate;
(S)-((1R,2S)-3-(3,5-difluorophenyl)-1-hydroxy-1-((2R,4R)-4-propoxypyrrolidin-2-yl)propan-2-yl) 2-((R)-3-isopropyl-2-oxopyrrolidin-1-yl)-4-phenylbutanoate;
(S)-((1R,2S)-3-(3,5-difluorophenyl)-1-hydroxy-1-((2R,4R)-4-propoxypyrrolidin-2-yl)propan-2-yl) 2-((S)-3-isobutyl-2-oxopyrrolidin-1-yl)-4-phenylbutanoate;

(S)-((1R,2S)-3-(3,5-difluorophenyl)-1-hydroxy-1-((2R,4R)-4-propoxypyrrolidin-2-yl)propan-2-yl) 2-((S)-3-isobutyl-2-oxopyrrolidin-1-yl)propanoate;

(S)-2-((S)-3-acetamido-3-((R)-sec-butyl)-2-oxopyrrolidin-1-yl)-N-((1R,2S)-3-(3,5-difluorophenyl)-1-hydroxy-1-((R)-piperidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-phenoxypyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-(pyridin-2-yloxy)pyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-phenoxypyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-2-yloxy)pyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-3-yloxy)pyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-hydroxypyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-hydroxypyrrolidin-2-yl)propan-2-yl)-4-phenylbutanamide;

(S)-2-((S)-3-acetamido-3-((R)-sec-butyl)-2-oxopyrrolidin-1-yl)-N-((1S,2S)-3-(3,5-difluorophenyl)-1-hydroxy-1-((R)-morpholin-3-yl)propan-2-yl)-4-phenylbutanamide;

(S)-N-((1R,2S)-1-((2R,4R)-4-(3,5-dimethoxybenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide;

(S)-N-((1R,2S)-1-((2R,4R)-4-(3-cyanobenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide;

(S)-N-((1R,2S)-1-((2R,4R)-4-(3-(trifluoromethyl)benzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide;

(S)-N-((1R,2S)-1-((2R,4R)-4-(4-fluorobenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-2-ylmethoxy)pyrrolidin-2-yl)propan-2-yl)-4-phenylbutanamide; and (S)-2-((S)-3-acetamido-3-((R)-sec-butyl)-2-oxopyrrolidin-1-yl)-N-((1R,2S)-1-hydroxy-3-phenyl-1-((2R,4R)-4-(propylsulfonyl)pyrrolidin-2-yl)propan-2-yl)-4-phenylbutanamide.

In another aspect, this application provides a method for the treatment or prevention of disorders responsive to the inhibition of β-Amyloid peptide in a mammal in need thereof, which comprises administering to said mammal a therapeutically effective amount of a compound of Formula (I) or a non-toxic pharmaceutically acceptable salt thereof. Preferably, the compounds of Formula (I) are useful for treating Alzheimer's Disease, cerebral Amyloid angioplasty and Down's Syndrome.

In still another aspect, the application provides pharmaceutical compositions comprising at least one compound of Formula (I) in combination with a pharmaceutically acceptable adjuvant, carrier or diluent.

DESCRIPTION OF THE SPECIFIC EMBODIMENTS

The compounds of this application and their preparation can be understood further by the following working examples. These examples are meant to be illustrative of the present application, and are not to be taken as limiting thereof.

Chemical abbreviations used in the specification and Examples are defined as follows:

"Ac" for acetate,
"APCI" for atmospheric pressure chemical ionization,
"Boc" or "BOC" for t-butyloxycarbonyl,
"BOP" for benzotriazol-1-yloxytris-(dimethylamino)-phosphonium hexafluorophosphate,
"Cbz" for benzyloxycarbonyl,
"CDI" for 1,1'-carbonyldiimidazole,
"CD$_3$OD" for deuteromethanol,
"CDCl$_3$" for deuterochloroform,
"DCC" for 1,3-dicyclohexylcarbodiimide,
"DCM" for dichloromethane
"DEAD" for diethyl azodicarboxylate,
"DIEA", "Hunig's base", or "DIPEA" for N,N-diisopropylethylamine,
"DMF" for N,N-dimethylformamide,
"DMAP" for 4-dimethylaminopyridine,
"DMPU" for 1,3-dimethyl-3,4,5,6-tetrahydro-2 (1H)-pyrimidone,
"DMSO" for dimethylsulfoxide,
"DPPA" for diphenylphosphorylazide
"EDC" or "EDCI" for 1-(3-dimethylaminopropyl)-3-ethylcarbodiimide hydrochloride,
"Et" for ethyl,
"EtOAC" for ethyl acetate,
"HOAc" for acetic acid,
"HOBt" for 1-hydroxybenzotriazole hydrate,
"HATU" for O-(7-azabenzotriazol-1-yl)-N,N, N',N'-tetramethyluronium hexafluorophosphate,
"HMPA" for hexamethylphosphoramide,
"LDA" for lithium diisopropylamide,
"LiHMDS" for lithium bis(trimethylsilyl)amide,
"NaHMDS" for sodium bis(trimethylsilyl)amide,
"NMM" for 4-methylmorpholine,
"PyBOP" for benzotriazole-1-yl-oxy-tris-pyrrolidino-phosphonium hexafluorophosphate,
"TMSCH$_2$N$_2$" for (trimethylsilyl)diazomethane,
"TMSN$_3$" for Azidotrimethylsilane,
"TBTU" for O-(1H-benzotriazol-1-yl)-N,N,N',N'-tetramethyluronium tetrafluoroborate,
"TEA" for triethylamine,
"TFA" for trifluoroacetic acid, and
"THF" for tetrahydrofuran.

Abbreviations used in the Examples are defined as follows:
"° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt"

for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

"HPLC" is an abbreviation used herein for high pressure liquid chromatography. Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). If necessary, organic layers can be dried over sodium sulfate unless otherwise indicated. However, unless otherwise indicated, the following conditions are generally applicable. "LC-MS" refers to high pressure liquid chromatography carried out according to the definition for HPLC with a mass spectrometry detector.

Melting points were determined on a Mel-Temp II apparatus and are uncorrected. IR spectra were obtained on a single-beam Nicolet Nexus FT-IR spectrometer using 16 accumulations at a resolution of 4.00 cm-1 on samples prepared in a pressed disc of KBr or as a film on KBr plates. Proton NMR spectra (300 MHz, referenced to tetramethylsilane) were obtained on a Varian INOUA 300, Bruker Avance 300, Avance 400, or Avance 500 spectrometer. Data were referred to the lock solvent. Electrospray Ionization (ESI) experiments were performed on a Micromass II Platform single-quadrupole mass spectrometer, or on a Finnigan SSQ7000 mass spectrometer. HPLC analyses were obtained using a Rainin Dynamax C18 column with UV detection at 223 nm using a standard solvent gradient program as follows:

HPLC solvent conditions: When described as performed under "standard conditions", Samples were dissolved in methanol (1 mg/mL) and run using the following gradient program with a solvent flow rate of 1.0 mL/min.

| Time (min) | Acetonitrile (0.05% TFA) | H$_2$O (0.05% TFA) |
| --- | --- | --- |
| Initial | 10 | 90 |
| 20.0 | 90 | 10 |
| 20-30 | 90 | 10 |

Preparatory HPLC: When described as performed under "standard conditions", Samples (approx. 20 mg) were dissolved in methanol (10 mg/mL) and purified on a 25 mm×50 mm Vydac C18 colum with a 5 minute gradient elution from 10% to 100% buffer B in buffer A (buffer A: water containing 0.1% trifluoroacetic acid, buffer B: 10% water, 90% acetonitrile containing 0.1% trifluoroacetic acid) at 10 mL/minute.

Analytical HPLC: When described as "Method A", a sample dissolved in a suitable carrier solvent (methanol, acetonitrile, or the like) was analyzed on an Xterra 3.0×50 mm s7 column with a run time of 3 min and a gradient of 0-100% B over 2 min at a flowrate of 5 mL/min. Absorbance was monitored at 220 μM. Solvent A=0% MeOH/90% water/0. 1% TFA and Solvent B=10% water/90% MeOH/0.1% TFA.

Analytical HPLC: When described as "Method B", a sample dissolved in a suitable carrier solvent (methanol, acetonitrile, or the like) was analyzed on an Xterra 3.0×50 mm s7 column with a run time of 4 min and a gradient of 0-100% B over 3 min at a flowrate of 5 mL/min. Absorbance was monitored at 220 μM. Solvent A=0% MeOH/90% water/0. 1% TFA and Solvent B=10% water/90% MeOH/0.1% TFA.

Analytical HPLC: When described as "Method C", a sample dissolved in a suitable carrier solvent (methanol, acetonitrile, or the like) was analyzed on an Xterra 4.6×50 mm S5 column with a run time of 4 min and a gradient of 0-100% B over 2 min at a flowrate of 5 mL/min. Absorbance was monitored at 220 μM. Solvent A=0% MeOH/90% water/0.1% TFA and Solvent B=10% water/90% MeOH/0.1% TFA.

Analytical HPLC: When described as "Method D", a sample dissolved in a suitable carrier solvent (methanol, acetonitrile, or the like) was analyzed on an Phenomenex-LUNA 4.6×50 mm S 10 column with a run time of 3 min and a gradient of 0-100% B over 2 min at a flowrate of 5 mL/min. Absorbance was monitored at 220 μM. Solvent A=10% MeOH/90% water/0.1% TFA and Solvent B=10% water/90% MeOH/0.1% TFA.

The examples provided are intended to assist in a further understanding of the present disclosure. Particular materials employed, species and conditions are intended to further illustrate the specific embodiments of the invention and not limit the reasonable scope thereof.

SYNTHESIS OF INTERMEDIATES

Preparation A (S)-2-((S)-3-acetamido-3-((S)-sec-butyl)-2-oxopyrrolidin-1-yl)-4-phenylbutanoic acid

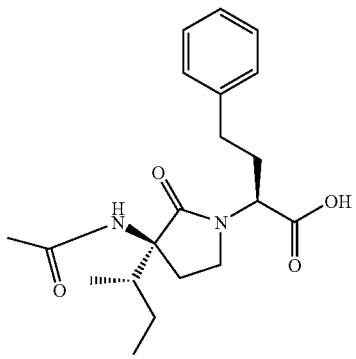

Step A (1): L-Isoleucine (10.0 g, 76.24 mmol), benzaldehyde (8.57 g, 76.24 mmol) and 4 Å molecular sieve (20 g) were added to a solution of NaOH (3.05 g, 76.24 mmol) in anhydrous MeOH (100 mL). The mixture was stirred at room temperature for overnight. After removal of molecular sieve by filtration with Celite, the filtrate was evaporated under reduced pressure to give a solid, which was further dried under vacuum for 8 h to give Schiff base 18.0 g (98%) as an off-white solid. $^1$H-NMR (DMSO-d$_6$) δ 8.12 (s, 1H), 7.65 (m, 2H), 7.36 (m, 3H), 2.45 (m, 1H), 1.38 (m, 1H), 0.91 (m, 1H), 0.76 (m, 6H).

Step A (2): 250 mL of CH$_2$Cl$_2$ was added to the Schiff base from step A(1) (12.0 g, 49.74 mmol). The solution was cooled to −20° C. After which 10.7 mL (74.61 mmol, 1.5 eq) benzyl chloroformate was added. Stirred at −20° C. for 96 h, warmed to room temperature, and diluted with CH$_2$Cl$_2$. The reaction mixture was washed 2× each with water, aqueous NaHCO$_3$, aqueous sodium bisulfite and water again. The organic layer was dried over MgSO$_4$, filtered, and the filtrate was concentrated and the residue was purified by chromatography on silica gel to give oxazolidinone 11 g (63%) as oil. APCI (M+H)$^+$=354.3. $^1$H-NMR(CDCl$_3$) δ 7.54-7.26 (m, 10H), 6.76 (s, 1H), 5.23 (s, 2H), 4.36-4.34 (dd, J=5.8 Hz, 1H), 1.80 (m, 1H), 1.60-1.20 (m, 2H), 0.86-0.80 (m, 6H).

Step A (3): 570 mg (1.613 mmol) of oxazolidinone from step A (2) in 10 mL anhydrous of THF was cooled to −78° C. Then added 0.22 mL (2.42 mmol, 1.5 eq) of allyl iodide followed by 4.8 mL of 0.5N (2.4 mmol, 1.5 eq) potassium bis(trimethylsilyl)amide. TLC at 60 min showed the reaction was complete, so it was quenched with aqueous NH$_4$Cl and warmed to room temperature. Then the solution was diluted with water and extracted with ethyl acetate. The combined ethyl acetate extracts were washed with dilute aqueous NH$_4$Cl, dried over MgSO$_4$, filtered, and the filtrate was concentrated. The residue was purified by silica gel chromatography to give disubstituted oxazolidinone 567 mg (89%). ESI (M+H)$^+$=394.4. $^1$H-NMR(CDCl$_3$) δ 7.42-7.26 (m, 10H), 6.34 (s, 1H), 5.68-5.57 (m, 1H), 5.16-5.12 (dd, J=9 Hz, 2H), 5.06 (s, 2H), 2.72-2.66 (m, 2H), 1.70-1.30 (m, 2H), 1.12-0.88 (m, 6H).

Step A (4): 567 mg (1.44 mmol) of disubstituted oxazolidinone from step A (3) was dissolved in 40 mL of THF-MeOH (3:1). 10 mL 2N NaOH was added and the mixture was refluxed for 2 h. The THF and MeOH was evaporated, diluted ethyl acetate and acidified with HCl. Extracted 2× with ethyl acetate, dried the organic layer with MgSO$_4$, filtered and the filtrate was evaporated. The residue was pumped on high vacuum to give crude acid 695 mg. ESI (M−H)$^−$=304.3.

Step A (5): 695 mg of acid (2.27 mmol) from step A (4), 15 mL of CH$_2$Cl$_2$, 488 mg HOBt (3.19 mmol, 1.4 eq) and 655 mg EDC (3.42 mmol, 1.5 eq) were mixed and stirred for 5 min. 660 mg (3.42 mmol, 1.5 eq) of homo-Phe methyl ester and 0.80 mL of DIEA (5.68 mmol, 2.5 eq) were then added and the mixture was stirred for 4 h. The reaction solution was diluted with ethyl acetate and washed with 5% citric acid and 5% NaHCO$_3$, dried over MgSO$_4$, filtered, and the filtrate was evaporated. The residue was purified by silica gel chromatography to provide Amide 0.53 g (76.7% for steps A(4) and A(5). ESI (M+H)$^+$=481.5. $^1$H-NMR(CDCl$_3$) δ 7.36-7.14 (m, 10H), 5.80-5.65 (m, 2H), 5.20-5.00 (m, 2H), 5.08 (s, 2H), 4.65-4.55 (m, 1H), 3.70 (s, 3H), 2.90-1.90 (m, 7H), 1.63-1.00 (m, 2H), 1.00-0.91 (m, 6H).

Step A (6): Ozone was bubbled through a solution of alkene from step A (5) in 10 mL of CH$_2$Cl$_2$ (0.78 g, 1.62 mmol) at −78° C. until a blue color persisted. Residual ozone was removed with a stream of oxygen. Triphenyl phosphine (0.60 g, 2.29 mmol) was added, and the reaction mixture was allowed to warm to rt. After 1 h, the solution was concentrated under reduced pressure. The residue was purified by chromatography on silica gel to provide aldehyde 0.47 g (61%). ESI (M+H)$^+$=483.4, (M+Na)$^+$=505.4.

Step A (7): 5 mL of TFA/Et$_3$SiH (1:1) was added to the solution of aldehyde from step A (6) (0.47 g, 0.97 mmol) in 10 mL of CH$_2$Cl$_2$ at 0° C. The mixture was stirred at 0° C. for 3 h. The reaction solution was concentrated under reduced pressure. The residue was purified by chromatography on silica gel to provide lactam 0.23 g (50%). ESI (M+H)$^+$=467.38. $^1$H-NMR(CDCl$_3$) δ 7.34-7.16 (m, 10H), 5.45 (br, 1H), 5.05 (s, 2H), 4.87-4.82 (dd, J=4 Hz, 1H)), 3.65-3.35 (m, 2H), 3.67 (s, 3H), 2.90-1.45 (m, 8H), 1.20-1.00 (m, 1H), 0.98-0.90 (m, 6H).

Step A (8): A solution of lactam from step A (7) (225 mg, 0.48 mmol) in methanol (15 mL) was hydrogenated over 10% palladium on carbon (40 mg) for overnight. The solution was filtered through Celite and concentrated under reduced pressure to afford the desired amine. ESI (M+H)$^+$=333.4. $^1$H-NMR(CDCl$_3$) δ 7.29-7.16 (m, 5H), 4.78-4.60 (m, 3H), 3.68 (s, 3H), 3.44-3.37 (m, 2H), 2.68-1.85 (m, 8H), 1.20-1.00 (m, 1H), 0.96-0.91 (m, 6H).

Step A (9): A mixture of acetic acid (54 μL, 0.91 mmol), HATU (348 mg, 0.92 mmol), and DIEA (257 μL, 0.91 mmol) in 5 mL of DMF was stirred at room temperature for 5 min. Amine (152 mg, 0.46 mmol) from step A (8) in 1 mL of DMF was added and the solution was continued to stir for overnight. The reaction solution was diluted with ethyl acetate and washed 3× with water, 1× brine, dried the organic layer with MgSO$_4$, filtered and the filtrate was evaporated. The residue was purified by chromatography on silica gel to provide lactam 160 mg (94%). ESI (M+H)$^+$=375.2. $^1$H-NMR(CDCl$_3$) δ 7.33-7.17 (m, 5H), 6.07 (br, 1H), 4.66-4.61 (m, 1H), 3.73 (s, 3H), 3.60-3.20 (m, 2H), 2.70-1.60 (m, 8H), 1.20-1.00 (m, 1H), 0.98-0.86 (m, 6H).

Step A (10): Compound (0.20 g, 0.53 mmol) from step A (9) was dissolved in 5 mL of THF/H$_2$O (4:1). LiOH (120 mg, 2.9 mmol) was added and the mixture was stirred for overnight. It was then diluted with ethyl acetate, acidified with 1N HCl. The aqueous layer was extracted with 3× ethyl acetate. The combined organic layer was dried over MgSO$_4$, filtered and evaporated under reduced pressure to give the title compound acid 98 mg (85%). ESI (M−H)$^−$=359.2.

Preparation B (S)-2-((R)-3-acetamido-3-isobutyl-2-oxopyrrolidin-1-yl)-4-phenylbutanoic acid

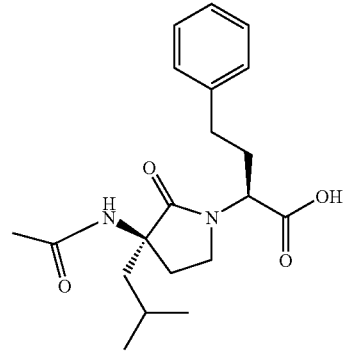

In a manner similar to the synthesis of the compound of Preparation A, but using L-Leucine the title compound of Preparation B was prepared.

Preparation C (1S,2S)-1-((2R,4R)-1-(4-methoxybenzyl)-4-(allyloxy)pyrrolidin-2-yl)-2-amino-3-(3,5-difluorophenyl)propan-1-ol

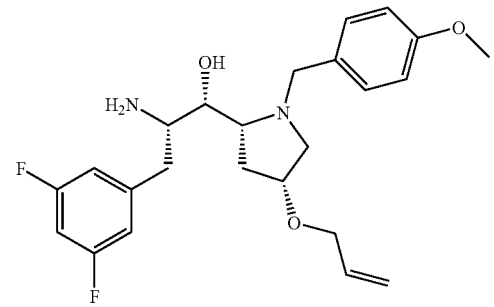

Step C (1): Preparation of (2R,4R)-1-(tert-butoxycarbonyl)-4-hydroxypyrrolidine-2-carboxylic acid. To a suspension of (2R,4R)-4-hydroxypyrrolidine-2-carboxylic acid (purchased from Aldrich)(10.0 g, 76.3 mmol) in 2:1 THF:H$_2$O (125 ml) was added a 2.5 molar aqueous sodium hydroxide solution (42.0 ml). To this mixture was added a solution of Di-tert-butyldicarbonate (22.6 g, 103.6 mmol) in 2:1 THF:H$_2$O (125 ml). The resulting reaction mixture was stirred at rt for 18 h. The mixture was then concentrated in vacuo to remove the THF. To the remaining aqueous mixture was added a 10% aqueous potassium hydrogen sulfate solution (150 ml). The resulting mixture was extracted with ethyl acetate. The organic phase was washed with H$_2$O, sat. aqueous NaCl, dried (MgSO$_4$), and concentrated in vacuo. The resulting slightly yellow oil was crystallized from hot ethyl acetate to give 11.8 g (67%) of (2R,4R)-1-(tert-butoxycarbonyl)-4-hydroxypyrrolidine-2-carboxylic acid as a white solid: $^1$H NMR (CD$_3$OD, 300 MHz) δ 1.44 (9H, m), 1.99-2.09 (1H, m), 2.35-2.49 (1H, m), 3.32-3.35 (1H, m), 3.60 (1H, dd, J=6, 12 Hz), 4.25 (1H, dd, J=6, 12 Hz), 4.31-4.36 (1H, m).

Step C (2): Preparation of (2R,4R)-4-(allyloxy)-1-(tert-butoxycarbonyl)pyrrolidine-2-carboxylic acid. To a suspension of NaH (60% in oil) (5.84 g, 146 mmol) in DMF (125 ml) cooled to 0° C. was added a solution of (2R,4R)-1-(tert-butoxycarbonyl)-4-hydroxypyrrolidine-2-carboxylic acid (Step C (1), 13.5 g, 58.4 mmol) in THF (100 ml) dropwise. When the addition was complete, the mixture was allowed to come to rt and stir until gas evolution ceased (30-45 min.). To the reaction mixture was then added allyl bromide (5.05 ml, 58.4 mmol) dropwise. The resulting mixture was stirred at rt for 2 h. The reaction was quenched by the slow addition of 1N HCl (150 ml). pH 4 buffer was added and the mixture was extracted with ethyl acetate. The organic phase was washed with sat. aqueous NaCl, dried (MgSO$_4$), and concentrated in vacuo. Flash chromatography (silica gel, 0-20% methanol/chloroform) gave 13.06 g (83%) of (2R,4R)-4-(allyloxy)-1-(tert-butoxycarbonyl)pyrrolidine-2-carboxylic acid as a clear, colorless oil: $^1$H NMR (CD$_3$OD, 300 MHz) δ 1.44 (9H, m), 2.18-2.44 (2H, m), 3.42 (1H, dd, J=3, 12 Hz), 3.59 (1H, dd, J=6, 12 Hz), 3.95-3.96 (2H, m), 4.10-4.14 (1H, m), 4.26-4.34 (1H, m), 5.12 (1H, d, J=12 Hz), 5.26 (1H, d, J=18 Hz), 5.80-5.92 (1H, m). HPLC retention time: 1.21 min (method A). MS (ESI) (M+H)$^+$ 272.17.

Step (C) 3: Preparation of (2R,4R)-tert-butyl 4-(allyloxy)-2-(hydroxymethyl)pyrrolidine-1-carboxylate. A solution of (2R,4R)-4-(allyloxy)-1-(tert-butoxycarbonyl)pyrrolidine-2-carboxylic acid (Step C (2), 13.06 g, 48.2 mmol) in THF (250 ml) was cooled to 0° C. Hunig's base (12.6 ml, 72.3 mmol) and ethyl chloroformate (5.51 ml, 57.8 mmol) were added and the mixture was stirred at 0° C. for 15 min. The mixture was then allowed to come to rt and stir for 2 h. during which white ppt. formed. NaBH$_4$ (1.68 g, 44.28 mmol) was then added and the mixture was again cooled to 0° C. To the resulting mixture was added MeOH (179 ml) very slowly. The MeOH addition results in gas evolution and an exotherm. When the addition was complete, the mixture was allowed to come to rt and stir for 2 h. The reaction was then concentrated in vacuo and the residue was partitioned between 1N HCl and ethyl acetate. The organic phase was washed with sat. aqueous NaCl, dried (MgSO$_4$), and concentrated in vacuo. Flash chromatography (silica gel, 0-10% methanol/chloroform) gave 9.58 g (77%) of (2R,4R)-tert-butyl 4-(allyloxy)-2-(hydroxymethyl)pyrrolidine-1-carboxylate as a clear, colorless oil: $^1$H NMR (CD$_3$OD, 300 MHz) δ 1.43 (9H, s), 1.82 (1H, brd s), 2.18 (1H, m), 3.40-3.54 (2H, m), 3.66-3.69 (2H, m), 3.93-4.00 (5H, m), 5.16 (1H, dd, J=3, 9 Hz), 5.24 (1H, dd, J=3, 15 Hz), 5.78-5.91 (1H, m). HPLC retention time: 1.28 min (method A). MS (ESI) (M+H)$^+$ 258.19.

Step C (4): Preparation of (2R,4R)-tert-butyl 4-(allyloxy)-2-formylpyrrolidine-1-carboxylate. To a solution of (2R,4R)-tert-butyl 4-(allyloxy)-2-(hydroxymethyl)pyrrolidine-1-carboxylate (Step C (3), 9.58 g, 37.28 mmol) in CH$_2$Cl$_2$ (500 ml) was added Dess Martin periodinane (acetic acid 1,1-diacetoxy-3-oxo-1λ$^5$-ioda-2-oxa-indan-1-yl ester) (32.0 g, 74.55 mmol). The resulting mixture was stirred at rt for 2 h. and then concentrated in vacuo. Flash chromatography (silica gel, 0-50% ethyl acetate/hexane) gave 7.39 g (78%) of (2R,4R)-tert-butyl 4-(allyloxy)-2-formylpyrrolidine-1-carboxylate as a slightly yellow oil: $^1$H NMR (CD$_3$OD, 300 MHz) δ 1.44 (9H, m), 2.01-2.35 (2H, m), 3.40-3.48 (1H, m), 3.55-3.70 (1H, m), 3.84-3.92 (2H, m), 4.04-4.20 (2H, m), 5.12-5.24 (2H, m), 5.74-5.87 (1H, m), 9.51-9.57 (1H, m). HPLC retention time: 1.39 min (method A). MS (ESI) (M+H+ CH$_3$OH)$^+$ 288.21.

Step C (5): Preparation of (2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine-1-carboxylate. To a solution of (S)-4-benzyl-3-(3-(3,5-difluorophenyl)propanoyl)oxazolidin-2-one (Preparation M, 1.47 g, 4.27 mmol) in CH$_2$Cl$_2$ (15 ml) at −78° C. was added Bu$_2$BOTf (di-n-butylboron triflate) (5.12 ml, 5.12 mmol, 1M in CH$_2$Cl$_2$) and Hunig's base (1.12 ml, 6.41 mmol). The resulting mixture was brought to 0° C. and stirred for 30 min. The mixture was again cooled to −78° C. and a solution of (2R,4R)-tert-butyl 4-(allyloxy)-2-formylpyrrolidine-1-carboxylate (Step C (4), 1.09 g, 4.27 mmol) in CH$_2$Cl$_2$ (10 ml) was added dropwise. When the addition was complete, the mixture was stirred at −78° C. for 5 min., then was allowed to warm to rt. After stirring at rt for 4 h. the mixture was concentrated in vacuo. Flash chromatography (silica gel, 0-75% ethyl acetate/hexane) gave 1.22 g (48%) of (2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy) pyrrolidine-1-carboxylate as a slightly yellow oil:

$^1$H NMR (CDCl$_3$, 300 MHz) δ 1.49 (9H, s), 2.03-2.22 (2H, m), 2.31 (1H, d, J=12 Hz), 2.98 (1H, dd, J=3, 15 Hz), 3.07 (1H, t, J=12 Hz), 3.42-3.57 (3H, m), 3.97-4.11 (8H, m), 4.57 (2H, brd s), 5.17-5.30 (2H, m), 5.81-5.94 (1H, m), 6.61 (1H, t, J=9 Hz), 6.90 (2H, brd s), 7.00 (2H, brd s), 7.26 (3H, m). HPLC retention time: 2.04 min (method A). MS (ESI) (M+H)$^+$ 601.37.

Step C (6): Preparation of (2S,3S)-2-(3,5-difluorobenzyl)-3-((2R,4R)-4-(allyloxy)-1-(tert-butoxycarbonyl)pyrrolidin-2-yl)-3-hydroxypropanoic acid. To a solution of (2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine-1-carboxylate (Step C (5), 1.02 g, 1.7 mmol) in THF (31 ml) was added a solution of LiOH (82 mg, 3.4 mmol) in H$_2$O (7.7 ml), then 30% H$_2$O$_2$ (2.58 ml). This reaction mixture was stirred at rt for 2 h. The mixture was then cooled to 0° C. and a solution of Na$_2$SO$_3$ in H$_2$O was added slowly to quench. The resulting mixture was allowed to come to rt and stir for 10 min. 1N HCl was added and the mixture was extracted with diethyl ether. The organic phase was washed with sat. aqueous NaCl, dried (MgSO$_4$), and concentrated in vacuo. Flash chromatography (silica gel, 50% MTBE/diethyl ether) gave 408 mg (54%) of (2S,3S)-2-(3,5-difluorobenzyl)-3-((2R,4R)-4-(allyloxy)-1-(tert-butoxycarbonyl)pyrrolidin-2-yl)-3-hydroxypropanoic acid as a clear, colorless oil: $^1$H NMR (CDCl$_3$, 300 MHz) δ 1.42 (9H, s), 1.46-1.51 (1H, m), 2.01-2.18 (2H, m), 2.56 (1H, t, J=9 Hz), 2.91 (1H, dd, J=9, 15 Hz), 3.20-3.30 (1H, m), 3.45-3.51 (2H, m), 3.96-4.24 (6H, m), 5.21-5.31 (2H, m), 5.81-5.94 (1H, m), 6.60 (1H, t, J=6 Hz), 6.74 (2H, t, J=6 Hz). HPLC retention time: 1.63 min (method A). MS (ESI) (M+H)$^+$ 442.25.

Step C (7): Preparation of (2R,4R)-tert-butyl 2-((4S,5S)-4-(3,5-difluorobenzyl)-2-oxooxazolidin-5-yl)-4-(allyloxy) pyrrolidine-1-carboxylate. To a solution of (2S,3S)-2-(3,5-difluorobenzyl)-3-((2R,4R)-4-(allyloxy)-1-(tert-butoxycarbonyl)pyrrolidin-2-yl)-3-hydroxypropanoic acid (Step C (6), 400 mg, 0.907 mmol) in toluene (22 ml) was added diphenylphosphoryl azide (353 µl, 1.63 mmol) and triethyl amine (253 µl, 1.81 mmol). This reaction mixture was brought to 65° C. and stirred for 18 h. The mixture was then concentrated in vacuo. The residue was taken up in ethyl acetate. This solution was washed with sat. aqueous sodium bicarbonate, H₂O, sat. aqueous NaCl, dried (MgSO₄), and concentrated in vacuo. Flash chromatography (silica gel, 0-60% ethyl acetate/hexane) gave 278 mg (70%) of (2R,4R)-tert-butyl 2-((4S,5S)-4-(3,5-difluorobenzyl)-2-oxooxazolidin-5-yl)-4-(allyloxy)pyrrolidine-1-carboxylate as a yellow oil: ¹H NMR (CDCl₃, 300 MHz) δ 1.46 (9H, s), 2.03-2.14 (1H, m), 2.43-2.53 (2H, m), 3.35 (1H, d, J=12 Hz), 3.70 (2H, brd s), 3.90-3.96 (2H, m), 4.06-4.11 (2H, m), 4.25 (1H, dt, J=3, 9 Hz), 4.78 (1H, s), 4.88 (1H, t, J=6 Hz), 5.18 (1H, dd, J=3, 9 Hz), 5.28 (1H, dd, J=3, 18 Hz), 5.83-5.96 (1H, m), 6.68-6.76 (3H, m). HPLC retention time: 1.68 min (method A). MS (ESI) (M+H)⁺ 439.27.

Step C (8): Prparation of (4S,5R)-4-(3,5-difluorobenzyl)-5-((2R,4R)-4-(allyloxy)pyrrolidin-2-yl)oxazolidin-2-one. A solution of (2R,4R)-tert-butyl 2-((4S,5S)-4-(3,5-difluorobenzyl)-2-oxooxazolidin-5-yl)-4-(allyloxy)pyrrolidine-1-carboxylate (Step C (7), 278 mg, 0.635 mmol) in CH₂Cl₂ (2 ml) was treated with TFA (1 ml). This reaction mixture was stirred at rt for 1 h. The mixture was then concentrated in vacuo. CH₂Cl₂ was added to the residue and the mixture was again concentrated in vacuo. The residue was partitioned between ethyl acetate and sat. aqueous sodium bicarbonate. The organic phase was washed with sat. aqueous NaCl, dried (MgSO₄), and concentrated in vacuo to give 185 mg (86%) of (4S,5R)-4-(3,5-difluorobenzyl)-5-((2R,4R)-4-(allyloxy)pyrrolidin-2-yl)oxazolidin-2-one as an opaque yellow oil: ¹H NMR (CDCl₃, 300 MHz) δ 2.05-2.23 (2H, m), 2.34 (1H, brd s), 2.61 (1H, t, J=12 Hz), 3.00-3.11 (2H, m), 3.16 (1H, dd, J=3, 12 Hz), 3.48-3.55 (1H, m), 3.90-4.13 (4H, m), 4.60 (1H, dd, J=9, 12 Hz), 4.92 (1H, s), 5.17 (1H, dd, J=3, 9 Hz), 5.26 (1H, dd, J=3.15 Hz), 5.82-5.95 (1H, m), 6.68-6.74 (3H, m). HPLC retention time: 0.84 min (method A). MS (ESI) (M+H)⁺ 339.20.

Step C (9): Preparation of (4S,5S)-4-(3,5-difluorobenzyl)-5-((2R,4R)-1-(4-methoxybenzyl)-4-(allyloxy)pyrrolidin-2-yl)oxazolidin-2-one. To a solution of (4S,5R)-4-(3,5-difluorobenzyl)-5-((2R,4R)-4-(allyloxy)pyrrolidin-2-yl)oxazolidin-2-one (Step C (8), 180 mg, 0.533 mmol) in CH₂Cl₂ (25 ml) was added 4-methoxybenzaldehyde (130 μl, 1.07 mmol) and AcOH (3 drops). This mixture was stirred at rt for 20 h. NaBH(OAc)₃ (339 mg, 1.60 mmol) was added and the reaction mixture was stirred at rt for an additional 24 h. CH₂Cl₂ was added and the mixture was washed with H₂O, dried (MgSO₄), and concentrated in vacuo. Flash chromatography (silica gel, 25-100% ethyl acetate/hexane) gave 172 mg (70%) of (4S,5S)-4-(3,5-difluorobenzyl)-5-((2R,4R)-1-(4-methoxybenzyl)-4-(allyloxy)pyrrolidin-2-yl)oxazolidin-2-one as a clear, colorless oil: ¹H NMR (CDCl₃, 300 MHz) δ 2.09-2.27 (2H, m), 2.52 (1H, t, J=12 Hz), 2.75 (1H, dd, J=6, 12 Hz), 2.91-3.02 (2H, m), 3.22 (1H, dt, J=3, 6 Hz), 3.48 (1H, d, J=15 Hz), 3.74 (3H, s), 3.82-3.99 (4H, m), 4.13 (1H, tt, J=3, 6 Hz), 4.72 (1H, t, J=6 Hz), 5.10 (1H, dd, J=3, 12 Hz), 5.22 (1H, dd, J=3, 18 Hz), 5.69 (1H, s), 5.78-5.91 (1H, m), 6.57-6.69 (3H, m), 6.82 (2H, d, J=9 Hz), 7.20 (2H, d, J=9 Hz). HPLC retention time: 1.10 min (method A). MS (ESI) (M+H)⁺ 459.27. Step C (10): Preparation of (1S,2S)-1-((2R,4R)-1-(4-methoxybenzyl)-4-(allyloxy)pyrrolidin-2-yl)-2-amino-3-(3,5-difluorophenyl)propan-1-ol. To a solution of of (4S,5S)-4-(3,5-difluorobenzyl)-5-((2R,4R)-1-(4-methoxybenzyl)-4-(allyloxy)pyrrolidin-2-yl)oxazolidin-2-one (Step C (9), 172 mg, 0.376 mmol) in EtOH (15 ml) was added a solution of LiOH (180 mg, 7.52 mmol) in H₂O (3.75 ml). This reaction mixture was brought to 100° C. and stirred for 4 h. The mixture was then concentrated in vacuo. 1N HCl was added to the residue. The resulting mix was washed with Et₂O. The aqueous phase was basified to pH 12 with ION NaOH. This mixture was extracted with ethyl acetate. The organic phase was washed with sat. aqueous NaCl, dried (MgSO₄), and concentrated in vacuo. Flash chromatography (silica gel, diethyl ether) gave 118 mg (73%) of (1S,2S)-1-((2R,4R)-1-(4-methoxybenzyl)-4-(allyloxy)pyrrolidin-2-yl)-2-amino-3-(3,5-difluorophenyl)propan-1-ol as a clear, colorless oil: ¹H NMR (CDCl₃, 300 MHz) δ 2.00-2.07 (2H, m), 2.31 (1H, dd, J=6, 12 Hz), 2.48 (1H, dd, J=9, 12 Hz), 2.85 (1H, m), 2.96-3.07 (2H, m), 3.24 (2H, d, J=12 Hz), 3.42 (1H, m), 3.77 (3H, s), 3.88 (2H, m), 3.92-3.97 (2H, m), 5.12 (1H, dd, J=3, 12 Hz), 5.22 (1H, dd, J=3, 18 Hz), 5.78-5.91 (1H, m), 6.64 (1H, tt, J=3, 9 Hz), 6.78 (2H, m), 6.82 (2H, d, J=9 Hz), 7.18 (2H, d, J=9 Hz). HPLC retention time: 1.04 min (method A). MS (ESI) (M+H)⁺ 433.30.

Preparation D (S)-2-((R)-3-isopropyl-2-oxopyrrolidin-1-yl)-4-phenylbutanoic acid

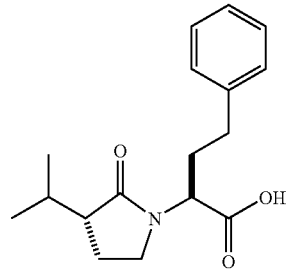

Step D (1): (4R,5S)-4-methyl-3-(3-methylbutanoyl)-5-phenyloxazolidin-2-one. To a solution of (4R,5S)-(+)-4-Methyl-5-phenyl-2-oxazolidinone (4.00 g, 22.6 mmol) in THF (225 mL) at −78° C. was added nBuLi (23.4 mL, 1.16 M in Hexane, 27.1 mmol) dropwise. After 10 minutes, isovaleryl chloride (3.31 mL, 27.1 mmol) was added. After 30 minutes the solution was allowed to warm to rt, at which time the reaction was quenched with saturated ammonium chloride solution. After 10 minutes, 1 M NaOH was added, and the mixture extracted 3 times with ethyl acetate. The combined organic layers were dried with MgSO₄, filtered, and concentrated in vacuo. Silica gel chromatography (0% to 20% EtOAc/Hexane gradient) afforded pure product (2.29 g, 39%). ¹H NMR (500 MHz, CDCl₃) δ ppm 0.89 (d, J=6.41 Hz, 3 H) 1.00 (d, J=6.41 Hz, 6 H) 2.14-2.27 (m, 1 H) 2.77 (dd, J=15.87, 7.02 Hz, 1 H) 2.86-2.95 (m, 1 H) 4.72-4.81 (m, 1 H) 5.64 (d, J=7.32 Hz, 1 H) 7.29 (d, J=7.63 Hz, 2 H) 7.33-7.44 (m, 3 H).

Step D (2): (4R,5S)-3-((R)-2-isopropylpent-4-enoyl)-4-methyl-5-phenyloxazolidin-2-one. To a solution of the compound of step D (1) (2.29 g, 8.77 mmol) in THF (17.4 mL) at −78° C. was added 1 M NaHMDS (10.52 mL, 10.52 mmol) dropwise. After 10 minutes, allyl bromide (2.28 mL, 26.3 mmol) was added in one shot. The reaction was continued at −78° C. until TLC showed complete reaction (~6 hours). The reaction was quenched with saturated ammonium chloride solution and allowed to come to room temperature. The mixture extracted 3 times with ethyl acetate. The combined organic layers were dried with MgSO₄, filtered, and concentrated in vacuo. Silica gel chromatography (0% to 10% EtOAc/Hexane gradient) afforded pure product (1.08 g, 41%). ¹H NMR (500 MHz, CDCl₃) δ ppm 0.85 (d, J=6.71 Hz, 3 H) 0.98 (d, J=6.71 Hz, 6 H) 1.94-2.04 (m, 1 H) 2.32-2.48 (m, 2 H) 3.81-3.91 (m, 1 H) 4.75-4.83 (m, 1 H) 4.95 (d, J=9.16 Hz, 1 H) 5.02 (dd, J=17.09, 1.53 Hz, 1 H) 5.61 (d, J=7.32 Hz, 1 H) 5.72-5.84 (m, 1 H) 7.30 (d, J=7.32 Hz, 2 H) 7.33-7.44 (m, 3 H).

Step D (3): (R)-2-isopropylpent-4-enoic acid. To a solution of the compound of step D (2) (1.08 g, 3.59 mmol) in THF (14.4 mL) was added water (3.59 mL), and the mixture cooled to 0° C. A solution of LiOH (172.5 mg, 7.20 mmol) and 30% $H_2O_2$ (3.26 mL) in water (11.2 mL) was added, and the combined mixture stirred for 10 minutes at 0° C. The ice bath was removed, and the reaction was allowed to continue for 1 h at rt. A solution of sodium sulfite (3.63 g) was added, and the reaction stirred for 10 min. Saturated sodium carbonate solution was added, and the reaction was extracted with methylene chloride. The aqueous layer was acidified to pH 1 with 6 N HCl, and extracted 3 times with diethyl ether. The combined ether layers were washed with brine, and dried over $MgSO_4$. The extract was filtered, and concentrated in vacuo to afford the desired product.

Step D (4): (5)-ethyl 2-((R)-2-isopropylpent-4-enamido)-4-phenylbutanoate. To a solution of the compound of step D (3) (130 mg, 915 μmol) and homophenylalanine ethyl ester hydrochloride (267.6 mg, 1.098 mmol) in DMF (10.2 mL) was added HATU (522 mg, 1.10 mmol) and N-Methyl morpholine (420 μL, 3.20 mmol). The reaction was stirred at rt until LC showed conversion to product. DMF was removed in vacuo, the residue suspended in water, and the product extracted 3 times to ethyl acetate. The combined organic extracts were dried over $MgSO_4$, filtered, and concentrated in vacuo. The crude product was suspended in a minimal amount of methylene chloride and filtered through glass wool. The solution was loaded onto a silica gel column, and pure product was obtained following elution with a ethyl acetate/hexane gradient (199.5 mg, 66%). $^1$H NMR (500 MHz, $CDCl_3$) δ ppm 0.92-1.01 (m, 6 H) 1.27 (t, J=7.0 Hz, 3 H) 1.83-1.93 (m, 2 H) 1.95-2.05 (m, 1 H) 2.13-2.23 (m, 1 H) 2.24-2.37 (m, 2 H) 2.56-2.71 (m, 2 H) 4.17 (q, J=7.02 Hz, 2 H) 4.63-4.71 (m, 1 H) 4.99 (d, J=10.07 Hz, 1 H) 5.06 (dd, J=17.09, 1.83 Hz, 1 H) 5.71-5.83 (m, 1 H) 5.92-5.98 (m, 1 H) 7.12-7.22 (m, 3 H) 7.24-7.30 (m, 2 H). HPLC retention time: 1.69 min (method A). MS (ESI) (M+H)$^+$ 332.

Step D (5): (S)-ethyl 2-((R)-3-isopropyl-2-oxopyrrolidin-1-yl)-4-phenylbutanoate. To a solution of the compound of step D (4) (199.5 mg, 603 μmol) in MeOH (12.0 mL) containing sodium acetate (36.0 mg, 444 μmol) at −78° C. was bubbled $O_3$. TLC within 3 minutes showed complete conversion to the ozonide. Nitrogen was bubbled through the solution to remove excess $O_3$. Triphenyl phosphine (474 mg, 1.81 mmol) was then added, and the mixture allowed to come to rt. To complete conversion of the ozonide intermediate, the solution was gently warmed at 50° C. until decomposition of the ozonide was complete. Solvents were removed in vacuo. The crude material was suspended in chloroform, filtered through glass wool onto a silica gel column, and purified via a ethyl acetate/hexane gradient. The aldehyde/hemiaminal so obtained was dissolved in methylene chloride (7.5 mL) and cooled to 0° C. Triethyl silane (2.25 mL) and TFA (2.25 mL) were simultaneously added, and the reaction stirred at 0° C. for 3 h. Solvents and reagents were removed in vacuo. Silica gel chromatography (ethyl acetate/hexane gradient) provided pure lactam ester.

$^1$H NMR (500 MHz, $CDCl_3$) δ ppm 0.88 (d, J=6.71 Hz, 3 H) 0.98 (d, J=7.02 Hz, 3 H) 1.24 (t, J=7.2 Hz, 3 H) 1.82-2.06 (m, 3 H) 2.19-2.35 (m, 2 H) 2.49-2.69 (m, 2 H) 3.21-3.28 (m, 1 H) 3.37-3.44 (m, 1 H) 4.11-4.19 (m, 2 H) 4.81 (dd, J=10.83, 4.73 Hz, 1 H) 7.14-7.22 (m, 3 H) 7.24-7.30 (m, 2 H). HPLC retention time: 1.65 min (method A). MS (ESI) (M+H)$^+$ 318.

Step D (6): (S)-2-((R)-3-isopropyl-2-oxopyrrolidin-1-yl)-4-phenylbutanoic acid. To a solution of the compound of step D (5) (160 mg, 500 μmol) in THF (6 mL) was added 2M LiOH (6 mL, 12 mmol). The mixture was stirred rapidly for 1 h. The mixture was made acidic with HCl, and the resulting mixture extracted 3 times with ethyl acetate. The combined organic extracts were washed with brine, dried over $MgSO_4$, filtered, and concentrated in vacuo. The title compound of Preparation D (lactam acid) was obtained (~quantitative yield).

$^1$H NMR (500 MHz, $CD_3OD$) δ ppm 0.88 (d, J=6.71 Hz, 3 H) 1.00 (d, J=7.02 Hz, 3 H) 1.82-2.03 (m, 2 H) 2.03-2.20 (m, 2 H) 2.22-2.32 (m, 1 H) 2.40-2.48 (m, 1 H) 2.61 (t, J=7.48 Hz, 2 H) 3.26-3.36 (m, 1 H) 3.38-3.46 (m, 1 H) 4.62 (dd, J=10.99, 4.27 Hz, 1 H) 7.13-7.21 (m, 3 H) 7.23-7.29 (m, 2 H). HPLC retention time: 1.50 min (method C). MS (ESI) (M+H)$^+$ 290.

Preparation E (S)-ethyl 2-((S)-3-isobutyl-2-oxopyrrolidin-1-yl)-4-phenylbutanoate

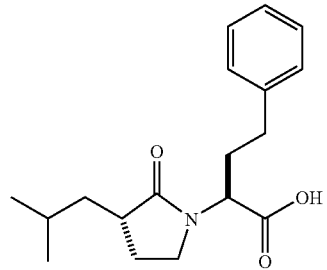

Step E (1): (4R,5S)-4-methyl-3-(4-methylpentanoyl)-5-phenyloxazolidin-2-one. To a solution of (4R,5S)-(+)-4-Methyl-5-phenyl-2-oxazolidinone (4.00 g, 22.6 mmol) in THF (225 mL) at −78° C. was added nBuLi (23.4 mL, 1.16 M in Hexane, 27.1 mmol) dropwise. After 10 minutes, 4-methylpentanoyl chloride (3.65 mL, 27.1 mmol) was added. After 30 minutes the solution was allowed to warm to rt, at which time the reaction was quenched with saturated ammonium chloride solution. After 10 minutes, 1 M NaOH was added, and the mixture extracted 3 times with ethyl acetate. The combined organic layers were dried with $MgSO_4$, filtered, and concentrated in vacuo. Silica gel chromatography (0% to 20% EtOAc/Hexane gradient) afforded pure product (2.37 g, 38%). $^1$H NMR (500 MHz, $CDCl_3$) δ ppm 0.89 (d, J=6.41 Hz, 3 H) 0.93 (d, J=6.41 Hz, 6 H) 1.49-1.68 (m, 3 H) 2.86-3.02 (m, 2 H) 4.72-4.79 (m, 1H) 5.65 (d, J=7.32 Hz, 1 H) 7.30 (d, J=7.32 Hz, 2 H) 7.34-7.44 (m, 3 H).

Step E (2): (4R,5S)-3-((S)-2-isobutylpent-4-enoyl)-4-methyl-5-phenyloxazolidin-2-one. To a solution of the compound of step E (1) (2.37 g, 8.62 mmol) in THF (17.1 mL) at −78° C. was added 1 M NaHMDS (10.34 mL, 10.34 mmol) dropwise. After 10 minutes, allyl bromide (2.24 mL, 25.9 mmol) was added in one shot. The reaction was continued at −78° C. until TLC showed complete reaction (~6 hours). The reaction was quenched with saturated ammonium chloride solution and allowed to come to room temperature. The mixture extracted 3 times with ethyl acetate. The combined organic layers were dried with $MgSO_4$, filtered, and concentrated in vacuo. Silica gel chromatography (0% to 10% EtOAc/Hexane gradient) afforded pure product (1.78 g, 66%). $^1$H NMR (500 MHz, CDCl$_3$) δ ppm 0.85 (d, J=6.41 Hz, 3 H) 0.89-0.93 (m, 6 H) 1.28-1.35 (m, 1 H) 1.52-1.62 (m, 1 H) 1.67-1.75 (m, 1 H) 2.25-2.32 (m, 1 H) 2.35-2.43 (m, 1 H) 4.00-4.08 (m, 1 H) 4.74-4.81 (m, 1 H) 4.97-5.06 (m, 2 H) 5.63 (d, J=7.32 Hz, 1 H) 5.75-5.86 (m, 1 H) 7.30 (d, J=7.32 Hz, 2 H) 7.34-7.44 (m, 3 H).

Step E (3): (S)-2-isobutylpent-4-enoic acid. To a solution of the compound of step E (2) (1.78 g, 5.65 mmol) in THF (22.7 mL) was added water (5.65 mL), and the mixture cooled to 0° C. A solution of LiOH (271.5 mg, 11.3 mmol) and 30% H$_2$O$_2$ (5.13 mL) in water (17.7 mL) was added, and the combined mixture stirred for 10 minutes at 0° C. The ice bath was removed, and the reaction was allowed to continue for 1 h at rt. A solution of sodium sulfite (5.71 g) was added, and the reaction stirred for 10 min. Saturated sodium carbonate solution was added, and the reaction was extracted with methylene chloride. The aqueous layer was acidified to pH 1 with 6 N HCl, and extracted 3 times with diethyl ether. The combined ether layers were washed with brine, and dried over MgSO$_4$. The extract was filtered, and concentrated in vacuo to afforded the desired product.

Step E (4): (S)-ethyl 2-((S)-2-isobutylpent-4-enamido)-4-phenylbutanoate. To a solution of the compound of step E (3) (200 mg, 1.28 mmol) and homophenylalanine ethyl ester hydrochloride (374.9 mg, 1.54 mmol) in DMF (14.3 mL) was added HATU (732 mg, 1.54 mmol) and N-Methyl morpholine (589 μL, 5.36 mmol). The reaction was stirred at rt until LC showed conversion to product. DMF was removed in vacuo, the residue suspended in water, and the product extracted 3 times to ethyl acetate. The combined organic extracts were dried over MgSO$_4$, filtered, and concentrated in vacuo. The crude product was suspended in a minimal amount of methylene chloride and filtered through glass wool. The solution was loaded onto a silica gel column, and pure product was obtained following elution with a ethyl acetate/hexane gradient (369.1 mg, 84%). $^1$H NMR (500 MHz, CDCl$_3$) δ ppm 0.90 (t, J=6.56 Hz, 6 H) 1.27 (t, J=7.0 Hz, 3 H) 1.54-1.65 (m, 2 H) 1.94-2.03 (m, 1 H) 2.12-2.37 (m, 4 H) 2.55-2.70 (m, 2 H) 4.18 (q, J=7.22 Hz, 2 H) 4.64-4.70 (m, 1 H) 4.99-5.09 (m, 2 H) 5.71-5.81 (m, 1 H) 5.97 (d, J=7.63 Hz, 1 H) 7.13-7.21 (m, 3 H) 7.27 (t, J=7.48 Hz, 2 H). HPLC retention time: 1.74 min (method A). MS (ESI) (M+H)$^+$ 346.

Step E (5): (S)-ethyl 2-((S)-3-isobutyl-2-oxopyrrolidin-1-yl)-4-phenylbutanoate. To a solution of the compound of step E (4) (369.1 mg, 1.07 mmol) in MeOH (21.3 mL) containing sodium acetate (64.0 mg, 790 μmol) at −78° C. was bubbled O$_3$. TLC within 3 minutes showed complete conversion to the ozonide. Nitrogen was bubbled through the solution to remove excess O$_3$. Triphenyl phosphine (842 mg, 3.21 mmol) was then added, and the mixture allowed to come to rt. To complete conversion of the ozonide intermediate, the solution was gently warmed at 50° C. until decomposition of the ozonide was complete. Solvents were removed in vacuo. The crude material was suspended in chloroform, filtered through glass wool onto a silica gel column, and purified via a 0% to 40% ethyl acetate/hexane gradient. The aldehyde/hemiaminal so obtained was dissolved in methylene chloride (15.0 mL) and cooled to 0° C. Triethyl silane (4.5 mL) and TFA (4.5 mL) were simultaneously added, and the reaction stirred at 0° C. for 3 h. Solvents and reagents were removed in vacuo. Silica gel chromatography (0% to 20% ethyl acetate/hexane gradient) provided pure lactam ester (321.1 mg, 95% yield). $^1$H NMR (500 MHz, CDCl$_3$) δ ppm 0.87-0.98 (m, 6 H) 1.20-1.32 (m, 4 H) 1.64-1.80 (m, 3 H) 1.95-2.06 (m, 1 H) 2.09-2.20 (m, 1 H) 2.22-2.34 (m, 1 H) 2.39-2.50 (m, 1 H) 2.52-2.70 (m, 2 H) 3.16-3.26 (m, 1 H) 3.40-3.49 (m, 1 H) 4.08-4.21 (m, 2 H) 4.79 (dd, J=10.68, 4.58 Hz, 1 H) 7.14-7.23 (m, 3 H) 7.23-7.32 (m, 2 H). HPLC retention time: 1.78 min (method C). MS (ESI) (M+H)$^+$ 332.

Step E (6): (S)-ethyl 2-((S)-3-isobutyl-2-oxopyrrolidin-1-yl)-4-phenylbutanoate. To a solution of the compound of step E (5) (310 mg, 940 μmol) in THF (9 mL) was added 2M LiOH (9 mL, 18 mmol). The mixture was stirred rapidly for 1 h. The mixture was made acidic with HCl, and the resulting mixture extracted 3 times with ethyl acetate. The combined organic extracts were washed with brine, dried over MgSO$_4$, filtered, and concentrated in vacuo. The Pure lactam acid title compound of Preparation E was obtained as a white solid (278 mg, 98% yield). $^1$H NMR (500 MHz, CD$_3$OD) δ ppm 0.90-0.99 (m, 6 H) 1.21-1.30 (m, 1 H) 1.59-1.75 (m, 3 H) 2.03-2.13 (m, 1 H) 2.13-2.22 (m, 1 H) 2.23-2.33 (m, 1 H) 2.42-2.51 (m, 1 H) 2.57-2.65 (m, 2 H) 3.31-3.36 (m, 1 H) 3.40-3.48 (m, 1 H) 4.56-4.63 (m, 1 H) 7.13-7.21 (m, 3 H) 7.22-7.30 (m, 2 H) HPLC retention time: 1.62 min (method C). MS (ESI) (M+H)$^+$ 303.

Preparation F (S)-2-((S)-3-isobutyl-2-oxopyrrolidin-1-yl)propanoic acid

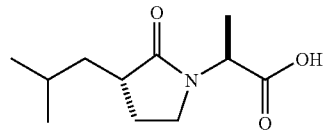

Step F (1): (S)-methyl 2-((S)-2-isobutylpent-4-enamido) propanoate. To a solution of the compound of step E (3) (200 mg, 1.28 mmol) and alanine methyl ester hydrochloride (215.0 mg, 1.54 mmol) in DMF (14.3 mL) was added HATU (732 mg, 1.54 mmol) and N-Methyl morpholine (589 μL, 5.36 mmol). The reaction was stirred at rt until LC showed conversion to product. DMF was removed in vacuo, the residue suspended in water, and the product extracted 3 times to ethyl acetate. The combined organic extracts were dried over MgSO$_4$, filtered, and concentrated in vacuo. The crude product was suspended in a minimal amount of methylene chloride and filtered through glass wool. The solution was loaded onto a silica gel column, and pure product was obtained following elution with a ethyl acetate/hexane gradient (271.6 mg, 88%). $^1$H NMR (500 MHz, CDCl$_3$) δ ppm 0.83-0.94 (m, 6 H) 1.18-1.30 (m, 1 H) 1.38 (d, J=7.3 Hz, 3 H) 1.51-1.64 (m, 2 H) 2.10-2.27 (m, 2 H) 2.27-2.38 (m, 1 H) 3.74 (s, 3 H) 4.54-4.66 (m, 1 H) 4.96-5.10 (m, 2 H) 5.68-5.83 (m, 1 H) 5.97 (d, J=6.41 Hz, 1 H). HPLC retention time: 1.41 min (method A). MS (ESI) (M+H)$^+$ 242.

Step F (2): (S)-methyl 2-((S)-3-isobutyl-2-oxopyrrolidin-1-yl)propanoate. To a solution of the compound of step F(1) (271.6 mg, 1.13 mmol) in MeOH (22.4 mL) containing sodium acetate (67.4 mg, 832 μmol) at −78° C. was bubbled O$_3$. TLC within 3 minutes showed complete conversion to the ozonide. Nitrogen was bubbled through the solution to remove excess O$_3$. Triphenyl phosphine (888 mg, 3.39 mmol) was then added, and the mixture allowed to come to rt. To complete conversion of the ozonide intermediate, the solution was gently warmed at 50° C. until decomposition of the ozonide was complete. Solvents were removed in vacuo. The crude material was suspended in chloroform, filtered through glass wool onto a silica gel column, and purified via a 0% to 60% ethyl acetate/hexane gradient. The aldehyde/hemiaminal so obtained was dissolved in methylene chloride (15.0 mL) and cooled to 0° C. Triethyl silane (4.5 mL) and TFA (4.5 mL) were simultaneously added, and the reaction stirred at 0° C. for 3 h. Solvents and reagents were removed in vacuo. Silica gel chromatography (0% to 50% ethyl acetate/hexane gradient) provided pure lactam ester (217.1 mg, 85% yield). $^1$H NMR (400 MHz, CDCl$_3$) δ ppm 0.89 (d, J=6.11 Hz, 3 H) 0.93 (d, J=6.36 Hz, 3 H) 1.22-1.31 (m, 1 H) 1.39 (d, J=7.58 Hz, 3 H) 1.64-1.79 (m, 3 H) 2.14-2.25 (m, 1 H) 2.39-2.51 (m, 1 H) 3.24-3.34 (m, 1 H) 3.36-3.45 (m, 1 H) 3.69 (s, 3 H) 4.87 (q, J=7.58 Hz, 1 H). HPLC retention time: 1.24 min (method C). MS (ESI) (M+H)$^+$ 228.

Step F (3): (S)-2-((S)-3-isobutyl-2-oxopyrrolidin-1-yl)propanoic acid. To a solution of the compound of step F(2) (211 mg, 929 µmol) in THF (9 mL) was added 2 M LiOH (9 mL, 18 mmol). The mixture was stirred rapidly for 1 h. The mixture was made acidic with HCl, and the resulting mixture extracted 3 times with ethyl acetate. The combined organic extracts were washed with brine, dried over MgSO$_4$, filtered, and concentrated in vacuo. Pure lactam acid was obtained as a white solid (185 mg, 93% yield). $^1$H NMR (500 MHz, CD$_3$OD) δ ppm 0.87-1.01 (m, 6 H) 1.20-1.33 (m, 1 H) 1.41 (d, J=7.6 Hz, 3 H) 1.58-1.79 (m, 3 H) 2.18-2.30 (m, 1 H) 2.44-2.57 (m, 1 H) 3.36-3.51 (m, 2 H) 4.69 (q, J=7.32 Hz, 1 H). HPLC retention time: 1.11 min (method C). MS (ESI) (M+H)$^+$ 213.

Preparation G (S)-2-((S)-3-butyl-2-oxopyrrolidin-1-yl)-4-phenylbutanoic acid

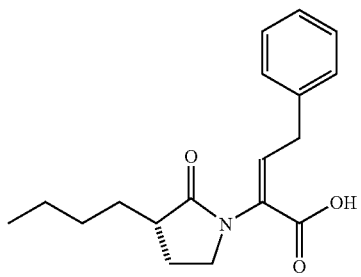

Step G (1): (4R,5S)-3-hexanoyl-4-methyl-5-phenyloxazolidin-2-one. To a solution of (4R,5S)-(+)-4-Methyl-5-phenyl-2-oxazolidinone (Aldrich Chemicals, 1.77 g, 10 mmol) in THF (100 mL) at −78° C. was added nBuLi (6.6 mL, 1.6 M in Hexane, 10.6 mmol) dropwise. After 10 minutes, hexanoyl chloride (1.68 mL, 12 mmol) was added. After 30 minutes the solution was allowed to warm to rt, at which time the reaction was quenched with saturated ammonium chloride solution. After 10 minutes, 1 M NaOH was added, and the mixture extracted 3 times with ethyl acetate. The combined organic layers were dried with MgSO$_4$, filtered, and concentrated in vacuo. Silica gel chromatography (0% to 20% EtOAc/Hexane gradient) afforded pure product (1.98 g, 72%). $^1$H NMR (500 MHz, CDCl$_3$) δ ppm 0.96-0.81 (m, 6 H) 1.40-1.26 (m, 4 H) 1.74-1.59 (m, 2 H) 3.04-2.81 (m, 2 H) 4.75 (dt, J=13.8, 6.7 Hz, 1 H) 5.64 (d, J=7.32 Hz, 1 H) 7.44-7.23 (m, 5 H).

Step G (2): (4R,5S)-3-((S)-2-allylhexanoyl)-4-methyl-5-phenyloxazolidin-2-one. To a solution of the compound of step G (1) (208 mg, 756 µmol) in THF (1.5 mL) at −78° C. was added 1 M NaHMDS (832 µL, 832 µmol) dropwise. After 10 minutes, allyl bromide (196 µL, 2.27 mmol) was added in one shot. The reaction was continued at −78° C. until TLC showed complete reaction (~6 hours). The reaction was quenched with saturated ammonium chloride solution and allowed to come to room temperature. The mixture extracted 3 times with ethyl acetate. The combined organic layers were dried with MgSO$_4$, filtered, and concentrated in vacuo. Silica gel chromatography (0% to 10% EtOAc/Hexane gradient) afforded pure product (137 mg, 58%). $^1$H NMR (500 MHz, CDCl$_3$) δ ppm 0.93-0.81 (m, 6 H) 1.35-1.21 (m, 4 H) 1.53-1.44 (m, 1 H) 1.75-1.66 (m, 1 H) 2.34-2.22 (m, 1 H) 2.47-2.36 (m, 1 H) 3.98-3.86 (m, 1 H) 4.82-4.74 (m, 1 H) 5.08-4.94 (m, 2 H) 5.63 (d, J=7.32 Hz, 1 H) 5.87-5.75 (m, 1 H) 7.46-7.24 (m, 5 H). HPLC retention time: 1.92 min (method A). MS (ESI) (M+H)$^+$ 316.

Step G (3): (S)-2-allylhexanoic acid. To a solution of the compound of step G (2) (1.22 g, 3.86 mmol) in THF (15.6 mL) was added water (3.86 mL), and the mixture cooled to 0° C. A solution of LiOH (185.7 mg, 7.75 mmol) and 30% H$_2$O$_2$ (3.51 mL) in water (12.1 mL) was added, and the combined mixture stirred for 10 minutes at 0° C. The ice bath was removed, and the reaction was allowed to continue for 1 h at rt. A solution of sodium sulfite (440 mg) was added, and the reaction stirred for 10 min. Saturated sodium carbonate solution was added, and the reaction was extracted with methylene chloride. The aqueous layer was acidified to pH 1 with 6 N HCl, and extracted 3 times with diethyl ether. The combined ether layers were washed with brine, and dried over MgSO$_4$. The extract was filtered, and concentrated in vacuo to afforded the desired product (63% yield). $^1$H NMR (500 MHz, CDCl$_3$) δ ppm 0.88 (t, J=7.0 Hz, 3 H) 1.22-1.41 (m, 4 H) 1.43-1.57 (m, 1 H) 1.57-1.73 (m, 1 H) 2.18-2.31 (m, 1 H) 2.32-2.53 (m, 2 H) 4.97-5.14 (m, 2 H) 5.65-5.87 (m, 1 H) 9.85 (s, 1 H).

Step G (4): (S)-ethyl 2-((S)-2-allylhexanamido)-4-phenylbutanoate. To a solution of the compound of step G (3) (421 mg, 2.69 mmol) and homophenylalanine ethyl ester hydrochloride (789 mg, 3.24 mmol) in DMF (30.1 mL) was added HATU (1.54 g, 3.24 mmol) and N-Methyl morpholine (1.24 mL, 9.42 mmol). The reaction was stirred at rt until LC showed conversion to product (<30 min). DMF was removed in vacuo, the residue suspended in water, and the product extracted 3 times to ethyl acetate. The combined organic extracts were dried over MgSO$_4$, filtered, and concentrated in vacuo. The crude product was suspended in a minimal amount of methylene chloride and filtered through glass wool. The solution was loaded onto a silica gel column, and pure product was obtained following elution with a ethyl acetate/hexane gradient (836 mg, 90%).

$^1$H NMR (500 MHz, CDCl$_3$) δ ppm 0.88 (t, J=7.02 Hz, 3 H) 1.19-1.38 (m, 7 H) 1.40-1.50 (m, 1H) 1.57-1.69 (m, 1 H) 1.92-2.06 (m, 1 H) 2.08-2.26 (m, 3 H) 2.28-2.41 (m, 1 H) 2.52-2.75 (m, 2 H) 4.18 (q, J=7.32 Hz, 2 H) 4.61-4.74 (m, 1 H) 4.95-5.11 (m, 2 H) 5.69-5.84 (m, 1 H) 5.96 (d, J=7.63 Hz, 1 H) 7.10-7.34 (m, 5 H). HPLC retention time: 1.76 min (method A). MS (ESI) (M+H)$^+$ 346.

Step G (5): (S)-ethyl 2-((S)-3-butyl-2-oxopyrrolidin-1-yl)-4-phenylbutanoate. To a solution of the compound of step G (4) (400 mg, 1.16 mmol) in MeOH (23.1 mL) containing sodium acetate (69.3 mg, 856 µmol) at −78° C. was bubbled O$_3$. TLC within 3 minutes showed complete conversion to the ozonide. Nitrogen was bubbled through the solution to remove excess O$_3$. Triphenyl phosphine (913 mg, 3.48 mmol) was then added, and the mixture allowed to come to rt. To complete conversion of the ozonide intermediate, the solution was gently warmed at 50° C. until decomposition of the ozonide was complete. Solvents were removed in vacuo. The crude material was suspended in chloroform, filtered through glass wool onto a silica gel column, and purified via a ethyl acetate/hexane gradient. The aldehyde/hemiaminal so obtained was dissolved in methylene chloride (17.5 mL) and cooled to 0° C. Triethyl silane (5.2 mL) and TFA (5.2 mL) were simultaneously added, and the reaction stirred at 0° C. for 3 h. Solvents and reagents were removed in vacuo. Silica gel chromatography (ethyl acetate/hexane gradient) provided pure lactam ester (345 mg, 90% yield). $^1$H NMR (500 MHz, CDCl$_3$) δ ppm 0.90 (t, J=7.0 Hz, 3 H) 1.24 (t, J=7.17 Hz, 3 H) 1.28-1.47 (m, 5 H) 1.66-1.79 (m, 1 H) 1.79-1.91 (m, 1 H) 1.93-2.06 (m, 1 H) 2.06-2.18 (m, 1 H) 2.22-2.34 (m, 1 H) 2.37-2.51 (m, 1 H) 2.51-2.71 (m, 2 H) 3.16-3.27 (m, 1 H) 3.38-3.50 (m, 1 H) 4.07-4.21 (m, 2 H) 4.79 (dd, J=10.83, 4.73 Hz, 1 H) 7.11-7.34 (m, 5 H). HPLC retention time: 1.78 min (method A). MS (ESI) (M+H)$^+$ 332.

Step G (6): (S)-2-((S)-3-butyl-2-oxopyrrolidin-1-yl)-4-phenylbutanoic acid. To a solution of the compound of step G (5) (100 mg, 302 μmol) in THF (3 mL) was added 2M LiOH (3 mL, 6 mmol). The mixture was stirred rapidly for 1 h. The mixture was made acidic with HCl, and the resulting mixture extracted 3 times with ethyl acetate. The combined organic extracts were washed with brine, dried over MgSO$_4$, filtered, and concentrated in vacuo. The pure compound of Preparation G was obtained as a white powder (84 mg, 92% yield). $^1$H NMR (500 MHz, CDCl$_3$) δ ppm 0.91 (t, J=6.7 Hz, 3 H) 1.28-1.41 (m, 5 H) 1.66-1.78 (m, 1 H) 1.79-1.92 (m, 1 H) 2.00-2.21 (m, 2 H) 2.27-2.38 (m, 1 H) 2.38-2.49 (m, 1 H) 2.54-2.73 (m, 2 H) 3.20-3.32 (m, 1 H) 3.35-3.47 (m, 1 H) 4.68 (dd, J=10.38, 4.88 Hz, 1 H) 7.12-7.34 (m, 5 H). HPLC retention time: 1.63 min (method A). MS (ESI) (M+H)$^+$ 304.

Preparation H (S)-2-((S)-3-butyl-2-oxopyrrolidin-1-yl)propanoic acid

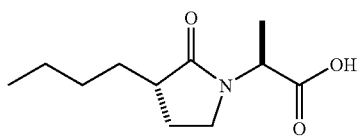

Step H (1): (S)-methyl 2-((S)-2-allylhexanamido) propanoate. To a solution of the compound of step G (3) (1.00 g, 6.41 mmol) and alanine methyl ester hydrochloride (1.07 g, 7.69 mmol) in DMF (71.5 mL) was added HATU (3.66 g, 7.70 mmol) and N-Methyl morpholine (2.95 mL, 22.4 mmol). The reaction was stirred at rt until LC showed conversion to product (<45 min). DMF was removed in vacuo, the residue suspended in water, and the product extracted 3 times to ethyl acetate. The combined organic extracts were dried over MgSO$_4$, filtered, and concentrated in vacuo. The crude product was suspended in a minimal amount of methylene chloride and filtered through glass wool. The solution was loaded onto a silica gel column, and pure product was obtained following elution with a 0-30% ethyl acetate/hexane gradient (1.23 g, 80%).

$^1$H NMR (500 MHz, CDCl$_3$) δ ppm 0.87 (t, J=7.02 Hz, 3 H) 1.19-1.34 (m, 4 H) 1.39 (d, J=7.32 Hz, 3 H) 1.41-1.50 (m, 1 H) 1.57-1.66 (m, 1 H) 2.06-2.23 (m, 2 H) 2.29-2.40 (m, 1 H) 3.74 (s, 3 H) 4.55-4.66 (m, 1 H) 4.95-5.09 (m, 2 H) 5.68-5.82 (m, 1 H) 5.97 (d, J=6.71 Hz, 1 H). HPLC retention time: 1.35 min (method C). MS (ESI) (M+H)$^+$ 242.

Step H (2): (S)-methyl 2-((S)-3-butyl-2-oxopyrrolidin-1-yl)propanoate. To a solution of the compound of Step H (1) (1.23 g, 5.12 mmol) in MeOH (102 mL) containing sodium acetate (306 mg, 3.78 mmol) at −78° C. was bubbled O$_3$. TLC within 3 minutes showed complete conversion to the ozonide. Nitrogen was bubbled through the solution to remove excess O$_3$. Triphenyl phosphine (4.03 g, 15.3 mmol) was then added, and the mixture allowed to come to rt. To complete conversion of the ozonide intermediate, the solution was gently warmed at 50° C. until decomposition of the ozonide was complete. Solvents were removed in vacuo. The crude material was suspended in chloroform, filtered through glass wool onto a silica gel column, and purified via a 0% to 60% ethyl acetate/hexane gradient. The aldehyde/hemiaminal so obtained (1.26 g) was dissolved in methylene chloride (78 mL) and cooled to 0° C. Triethyl silane (23.4 mL) and TFA (23.4 mL) were simultaneously added, and the reaction stirred at 0° C. for 3 h. Solvents and reagents were removed in vacuo. Silica gel chromatography (ethyl acetate/hexane gradient) provided the lactam ester.

$^1$H NMR (500 MHz, CDCl$_3$) δ ppm 0.89 (t, J=7.02 Hz, 3 H) 1.26-1.47 (m, 5 H) 1.43 (d, J=7.63 Hz, 3 H) 1.75-1.86 (m, 2 H) 2.17-2.27 (m, 1 H) 2.54-2.62 (m, 1 H) 3.38 (dd, J=15.72, 8.70 Hz, 1 H) 3.46-3.53 (m, 1 H) 3.72 (s, 3 H) 4.87 (q, J=7.32 Hz, 1 H). HPLC retention time: 1.28 min (method C). MS (ESI) (M+H)$^+$ 228.

Step H (3): (S)-2-((S)-3-butyl-2-oxopyrrolidin-1-yl)propanoic acid. The general procedure of step G (6) was applied to transform the compound of step H (2) into the title compound of Preparation H.

HPLC retention time: 1.32 min (method C). MS (ESI) (M+H)$^+$ 214.

Preparation I (1S,2S)-2-amino-1-((R)-1-benzhydrylpiperidin-2-yl)-3-(3,5-difluorophenyl)propan-1-ol

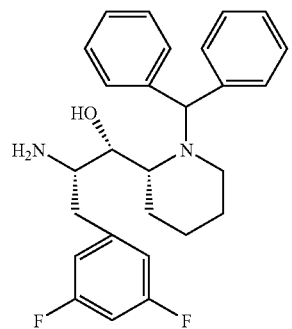

Step I (1): Preparation of tert-butyl 2-(hydroxymethyl)piperidine-1-carboxylate. To a solution of piperidin-2-ylmethanol (6.3 g, 54.8 mmol) in 1,4-dioxane (100 mL) were added 1N aqueous sodium hydroxide solution (100 mL) and di-tert-butyldicarbonate (15.5 g, 71.2 mmol). The resulting reaction mixture was stirred at rt overnight. Ethyl acetate (500 mL) was added and the mixture was washed with 1 N aqueous HCl (150 mL) twice, H$_2$O, and dried (Na$_2$SO$_4$), and concentrated in vacuo. 9.0 g of product was obtained as the title compound (76% yield): $^1$H NMR (CDCl$_3$, 500 MHz) δ 1.42-1.46 (11H, m), 1.56-1.67 (4H, m), 2.86 (1H, m), 3.60 (1H, dd, J=5, 10 Hz), 3.81 (1H, m), 3.93 (1H, m), 4.29 (1H, m).

Step I (2): Preparation of tert-butyl 2-formylpiperidine-1-carboxylate. To a solution of tert-butyl 2-(hydroxymethyl)piperidine-1-carboxylate (Step I (1), 1.80 g, 8.4 mmol) in dichloromethane was added Dess-Martin reagent (15 wt % in dichloromethane, 4.6 g, 27.3 mmol). The mixture was stirred at rt for 1.5 h. The mixture was then concentrated in vacuo and purified by silica gel Flash Chromatography to give 1.4 g of the title compound (78% yield): $^1$H NMR (CDCl$_3$, 500 MHz) δ 1.23-1.33 (1H, m), 1.38-1.46 (9H, m), 1.54-1.69 (4H, m), 2.92 (1H, m), 3.88-4.08 (1H, m), 4.47-4.61 (1H, m), 9.58 (1H, s).

Step I (3): Preparation of tert-butyl 2-((1S,2S)-2-(3,5-difluorobenzyl)-3-((S)-4-benzyl-2-oxooxazolidin-3-yl)-1-hydroxy-3-oxopropyl)piperidine-1-carboxylate. To a solution of (S)-4-benzyl-3-(3-(3,5-difluorophenyl)propanoyl)oxazolidin-2-one (Preparation M, 2.2 g, 6.57 mmol) in CH$_2$Cl$_2$ (100 mL) at −78° C. was added Bu$_2$BOTf (di-n-butylboron triflate) (7.9 ml, 7.9 mmol, 1M in CH$_2$Cl$_2$) and triethyl amine (1.4 mL, 10 mmol). The resulting mixture was brought up to 0° C. and stirred for 20 min. The mixture was cooled back to −78° C. and a solution of tert-butyl 2-formylpiperidine-1-carboxylate (Step I (2), 1.4 g, 6.57 mmol) in CH$_2$Cl$_2$ (100 mL) was added. When the addition was complete, the mixture was allowed to warm to and stirred at rt overnight. MeOH was added and the mixture was concentrated in vacuo. The crude mixture was purified by silica gel Flash chromatography to give 2.0 g of the title compound: $^1$H NMR (CDCl$_3$, 500 MHz) δ 1.42-1.66 (14H, m), 1.86-2.26 (1H, m), 2.62-3.40 (6H, m), 3.84-4.69 (7H, m), 6.58-6.65 (1H, m), 6.81-6.85 (2H, m), 6.90-6.96 (2H, m), 7.22-7.27 (3H, m). MS (ESI) (M+Na)$^+$ 581.12.

Step I (4): Preparation of (2S,3S)-2-(3,5-difluorobenzyl)-3-(1-(tert-butoxycarbonyl)piperidin-2-yl)-3-hydroxypropanoic acid. To a solution of tert-butyl 2-((1S,2S)-2-(3,5-difluorobenzyl)-3-((s)-4-benzyl-2-oxooxazolidin-3-yl)-1-hydroxy-3-oxopropyl)piperidine-1-carboxylate (Step 1 (3), 1.6 g, 2.87 mmol) in THF (100 mL) was added a solution of LiOH (137 mg, 5.73 mmol) in H$_2$O (25 mL), then 30% H$_2$O$_2$ (4.9 g) was added at 0° C. This reaction mixture was warmed up to rt and stirred at rt overnight. THF was removed and ethyl acetate (500 mL) was added. The mixture was washed with 1N HCl, and H$_2$O, dried (Na$_2$SO$_4$), and concentrated in vacuo to give the crude product which was ready for next step without purification. MS (ESI) (M+H)$^+$ 400.18.

Step I (5): Preparation of (R)-tert-butyl 2-((4S,5S)-4-(3,5-difluorobenzyl)-2-oxooxazolidin-5-yl)piperidine-1-carboxylate. To a solution of (2S,3S)-2-(3,5-difluorobenzyl)-3-(1-(tert-butoxycarbonyl)piperidin-2-yl)-3-hydroxypropanoic acid (Step I (4), 1.3 g, 3.26 mmol) in toluene (80 mL) was added diphenylphosphoryl azide (1.6 g, 5.86 mmol) and triethyl amine (823 mg, 8.15 mmoL). This reaction mixture was stirred at 55° C. overnight and 100° C. for 6 h. Toluene was removed and ethyl acetate (500 mL) was added. The mixture was washed with H$_2$O, dried over Na$_2$SO$_4$ and concentrated. The crude mixture was purified by silica gel Flash Chromatography to give 580 mg of the title compound: $^1$H NMR (CDCl$_3$, 500 MHz) δ 1.27-1.35 (2H, m), 1.42-1.44 (9H, m), 1.50-1.98 (3H, m), 2.48-2.63 (1H, m), 2.78-3.24 (3H, m), 3.84 (1H, m), 4.10 (1H, m), 4.48-5.29 (2H, m), 6.62-6.69 (2H, m), 6.70-6.74 (1H, m). MS (ESI) (M−H)$^−$ 395.07.

Step I (6): Preparation of (4S,5R)-4-(3,5-difluorobenzyl)-5-((R)-piperidin-2-yl)oxazolidin-2-one. A solution of (R)-tert-butyl 2-((4S,5S)-4-(3,5-difluorobenzyl)-2-oxooxazolidin-5-yl)piperidine-1-carboxylate (Step I (5), 200 mg) in CH$_2$Cl$_2$ (4 mL) was treated with TFA (2 mL). This reaction mixture was stirred at rt for 1 h. The mixture was then concentrated in vacuo with addition of toluene. 1N HCl solution (50 mL) was added and the mixture was extracted with diethyl ether, neutralized with 50% aqueous NaOH to pH=12. The mixture was extracted with ethyl acetate (50 mL) twice.

The combined organic layers were dried (Na$_2$SO$_4$), and concentrated in vacuo to give 132 mg of the title compound: $^1$H NMR (CDCl$_3$, 500 MHz) δ 1.13-1.38 (3H, m), 1.62 (1H, m), 1.90 (1H, m), 2.01 (1H, m), 2.52-2.64 (2H, m), 2.84 (1H, m), 3.03 (1H, m), 3.25 (1H, m), 3.92 (1H, m), 4.26 (1H, dd, J=5, 10 Hz), 5.31 (1H, s), 6.62-6.78 (3H, m). MS (ESI) (M+H)$^+$ 297.13.

Step I (7): Preparation of (4S,5S)-4-(3,5-difluorobenzyl)-5-((R)-1-benzhydrylpiperidin-2-yl)oxazolidin-2-one. To a solution of (4S,5R)-4-(3,5-difluorobenzyl)-5-((R)-piperidin-2-yl)oxazolidin-2-one (Step I (6), 70 mg, 0.24 mmol) in acetonitrile (1.8 mL) were added potassium carbonate (50 mg, 0.36 mmol) and bromodiphenylmethane (90 mg, 0.36 mmol). The reaction mixture was then heated to 100° C. for 30 min using microwave heating. The solvent was removed and the crude mixture was purified by silica gel Flash Chromatography to give 60 mg of the title compound (50% yield): $^1$H NMR (CDCl$_3$, 500 MHz) δ 1.28 (1H, brd s), 1.56-1.83 (4H, m), 1.94 (1H, m), 2.13 (1H, t, J=10 Hz), 2.67 (1H, m), 2.77 (1H, m), 2.88 (1H, m), 3.16 (1H, t, J=5 Hz), 3.81 (1H, m), 4.95 (1H, s), 5.10 (1H, s), 5.14 (1H, m), 6.54 (2H, m), 6.69 (1H, m), 7.18-7.27 (4H, m), 7.32-7.38 (4H, m), 7.42 (2H, d, J=10 Hz). MS (ESI) (M+Na)$^+$ 485.12.

Step I (8): Preparation of (1S,2S)-2-amino-1-((R)-1-benzhydrylpiperidin-2-yl)-3-(3,5-difluorophenyl)propan-1-ol. To a solution of of (4S,5S)-4-(3,5-difluorobenzyl)-5-((R)-1-benzhydrylpiperidin-2-yl)oxazolidin-2-one (Step I (7), 60 mg, 0.13 mmol) in EtOH (3 mL) was added a solution of LiOH (31 mg, 1.3 mmol) in H$_2$O (1 mL). This reaction mixture was brought to 100° C. and stirred for 16 h. 1N HCl solution (50 mL) was added to the mixture and washed with diethyl ether. The aqueous phase was basified with 50% aqueous NaOH solution. This mixture was extracted with ethyl acetate (50 mL) twice. The combined organic layer was dried (Na$_2$SO$_4$), and concentrated in vacuo to give 55 mg of the title compound of Preparation 1 (97% yield): $^1$H NMR (CDCl$_3$, 500 MHz) δ 1.24-1.36 (2H, m), 1.38-1.43 (1H, m), 1.62-1.70 (2H, m), 1.73-1.82 (2H, m), 2.01 (2H, brd s), 2.36-2.43 (2H, m), 2.70 (1H, m), 2.91 (1H, m), 2.98 (1H, d, J=15 Hz), 3.28 (1H, s), 4.09 (1H, m), 5.41 (1H, s), 6.69 (1H, m), 6.80 (2H, d, J=10 Hz), 7.17 (1H, m), 7.22-7.28 (3H, m), 7.30-7.34 (4H, m), 7.36 (2H, d, J=5 Hz). MS (ESI) (M+H)$^+$ 437.19.

Preparation J (4S,5S)-4-(3,5-difluorobenzyl)-5-((2R,4R)-1-benzhydryl-4-hydroxypyrrolidin-2-yl)oxazolidin-2-one

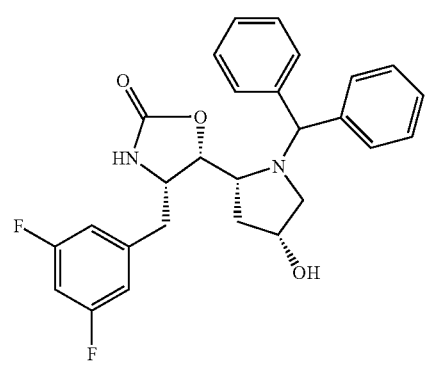

Step J (1): (4S,5S)-4-(3,5-difluorobenzyl)-5-((2R,4R)-4-(allyloxy)-1-benzhydrylpyrrolidin-2-yl)oxazolidin-2-one. A mixture of (4S,5R)-4-(3,5-difluorobenzyl)-5-((2R,4R)-4-(allyloxy)pyrrolidin-2-yl)oxazolidin-2-one (Step C (8), 2.03 g, 6.0 mmol), benzylhydryl bromide (2.22 g, 9.0 mmol), and potassium carbonate (1.24 g, 9.0 mmol) in acetonitrile (40 mL) was stirred at reflux for 35 min. After cooling to rt, the mixture was filtered and concentrated in vacuo. The crude mixture was purified by Flash Chromatography (silica gel, 0-7.5% methanol/chloroform) to give a slightly yellow oil as the title compound (2.64 g, 87% yield): $^1$H NMR (CDCl$_3$, 300 MHz) δ 1.95-2.23 (2H, m), 2.36 (1H, t, J=12 Hz), 2.70 (1H, m), 3.02 (2H, d, J=6 Hz), 3.48 (1H, m), 3.71-3.99 (4H, m), 4.70 (2H, s), 4.78 (1H, t, J=6 Hz), 4.93 (1H, s), 5.12 (1H, m), 5.22 (1H, dd, J=3, 18 Hz), 5.84 (1H, m), 6.49 (1H, d, J=6 Hz), 6.67 (1H, m), 7.20-7.39 (11H, m).

Step J (2): (4S,5S)-4-(3,5-difluorobenzyl)-5-((2R,4R)-1-benzhydryl-4-hydroxypyrrolidin-2-yl)oxazolidin-2-one. To a solution of (4S,5S)-4-(3,5-difluorobenzyl)-5-((2R,4R)-4-(allyloxy)-1-benzhydrylpyrrolidin-2-yl)oxazolidin-2-one (Step J (1), 2.37 g, 4.7 mmol) in 10% H$_2$O/EtOH (45 mL) were added RhCl(PPh$_3$)$_3$ (326 mg, 0.353 mmol) and DABCO (111 mg, 0.987 mmol). The mixture was stirred at reflux for 4 h and then 45 drops of conc. HCl was added the mixture was stirred at reflux for another 2 h. H$_2$O was added and the mixture was concentrated to remove EtOH. pH 7 buffer was added and the mixture was extracted with diethyl ether. The combined organic phases were washed with sat. aqueous NaCl, dried (MgSO$_4$), and concentrated in vacuo. Flash chromatography (silica gel, 0-10% methanol/chloroform) gave the title compound (1.3 g, 60% yield): $^1$H NMR (CDCl$_3$, 300 MHz) δ 1.98 (1H, m), 2.23 (1H, m), 2.43-2.65 (3H, m), 2.92 (1H, d, J=9 Hz), 3.08 (1H, d, J=9 Hz), 3.26 (1H, d, J=9 Hz), 3.68 (1H, m), 4.19 (1H, brd s), 4.52 (1H, d, J=9 Hz), 4.75 (1H, s), 5.05 (1H, s), 6.58 (1H, m), 6.73 (1H, m), 7.24-7.35 (10H, m). HPLC retention time: 1.32 min (method A). MS (ESI) (M+H)$^+$ 465.15.

Preparation K (4S,5S)-4-(3,5-difluorobenzyl)-5-((2R,4S)-1-benzhydryl-4-hydroxypyrrolidin-2-yl)oxazolidin-2-one

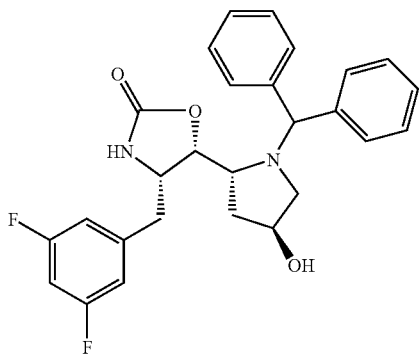

Step K (1): (3S,5R)-5-((4S,5S)-4-(3,5-difluorobenzyl)-2-oxooxazolidin-5-yl)-1-benzhydrylpyrrolidin-3-yl acetate. To a solution of triphenylphosphine (510 mg, 1.94 mmol) in THF (20 mL) at 0° C. was added DEAD (0.36 mL, 1.94 mmol) and the mixture was allowed to come to rt for 5 min and was again cooled to 0° C. A solution of (4S,5S)-4-(3,5-difluorobenzyl)-5-((2R,4R)-1-benzhydryl-4-hydroxypyrrolidin-2-yl)oxazolidin-2-one (Preparation J, 750 mg, 1.62 mmol) in THF (20 mL) was added and the mixture was allowed to come to rt for 5 min and was again cooled to 0° C. Acetic acid (0.093 mL, 1.62 mmol) was added and the mixture was warmed to rt and stirred for 30 min. pH 7 buffer was added and the mixture was extracted with ethyl acetate. The combined organic phases were washed with sat. aqueous NaCl, dried (MgSO$_4$), and concentrated in vacuo. Flash chromatography (silica gel, 5-100% ethyl acetate/hexane) gave 661 mg (81% yield) of the title compound as a clear, very slightly yellow oil: $^1$H NMR (CDCl$_3$, 500 MHz) δ 1.31-1.34 (1H, m), 2.08-2.16 (1H, m), 2.39 (3H, m), 2.80 (1H, brd s), 3.26 (1H, brd s), 3.60 (2H, brd s), 4.11 (1H, m), 4.27-4.33 (1H, m), 4.91 (2H, m), 5.28 (1H, m), 6.40 (2H, brd s), 6.51 (2H, m), 6.69 (1H, m), 7.22 (1H, m), 7.28-7.49 (8H, m). HPLC retention time: 1.50 min (method A). MS (ESI) (M+H)$^+$ 507.17.

Step K (2): (4S,5S)-4-(3,5-difluorobenzyl)-5-((2R,4S)-1-benzhydryl-4-hydroxypyrrolidin-2-yl)oxazolidin-2-one. A solution of (3S,5R)-5-((4S,5S)-4-(3,5-difluorobenzyl)-2-oxooxazolidin-5-yl)-1-benzhydrylpyrrolidin-3-yl acetate (Step K (1), 661 mg, 1.31 mmol) in MeOH (20 mL) was treated with potassium carbonate (400 mg). The mixture was stirred at rt for 2 h. The mixture was filtered and concentrated in vacuo. Flash chromatography (silica gel, 0-75% ethyl acetate/hexane) gave the title compound of Preparation K (300 mg):

$^1$H NMR (CDCl$_3$, 500 MHz) δ 1.80 (1H, d, J=5 Hz), 1.98 (1H, m), 2.26-2.31 (1H, m), 2.41-2.49 (2H, m), 2.55 (1H, m), 3.14 (1H, dd, J=5, 10 Hz), 3.47-3.54 (2H, m), 4.50 (1H, d, J=5 Hz), 4.60 (1H, d, J=5 Hz), 4.90 (2H, m), 6.52 (2H, m), 6.69 (1H, m), 7.20-7.23 (2H, m), 7.26-7.32 (4H, m), 7.41 (4H, t, J=10 Hz). HPLC retention time: 1.26 min (method A). MS (ESI) (M+H)$^+$ 465.14.

Preparation L (4S,5S)-4-(3,5-difluorobenzyl)-5-((2R,4S)-1-benzhydryl-4-hydroxypyrrolidin-2-yl)oxazolidin-2-one

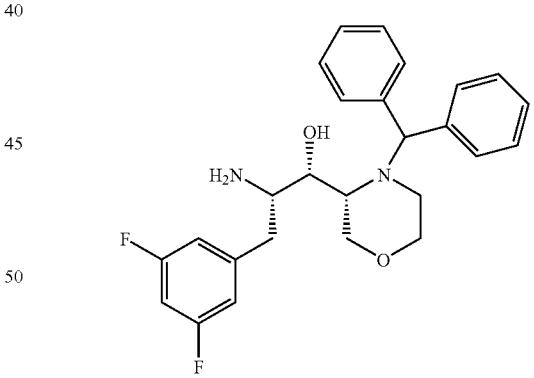

Step L (1): tert-Butyl 3-(hydroxymethyl)morpholine-4-carboxylate. To a solution of 4-(tert-butoxycarbonyl)morpholine-3-carboxylic acid (4.7 g, 20.35 mmol) in THF (120 mL) were added Hunig's base (6.6 g, 50.875 mmol). Then chloroethylformate (2.65 g, 24.4 mmol) was added at 0° C. After stirring from 0° C. to rt over 1.5 h, NaBH$_4$ (3.1 g, 81.4 mmol) was added and after 15 min, MeOH (20 mL) was added slowly at 0° C. After stirring at rt for 1 h, THF and MeOH was removed and ethyl acetate (600 mL) was added and the mixture was washed with NaHCO$_3$, H$_2$O, and dried (Na$_2$SO$_4$), and concentrated in vacuo. 3.56 g of product was obtained as the title compound (81% yield): $^1$H NMR (CDCl$_3$, 500 MHz) δ 1.46 (9H, s), 2.03 (1H, brd s), 3.17 (1H, m), 3.46 (1H, m), 3.56 (1H, m), 3.72-3.86 (4H, m), 3.91 (1H, d, J=10 Hz), 3.99 (1H, brd s).

Step L (2): tert-Butyl 3-formylmorpholine-4-carboxylate. To a solution of dimethyl sulfoxide (32.4 g, 41.5 mmol) in dichloromethane (100 mL) was added oxalyl dichloride (3.14 g, 24.7 mmol) at −78° C. After stirring at −78° C. for 15 min, the mixture was added a solution of tert-butyl 3-(hydroxymethyl)morpholine-4-carboxylate (step L (1), 3.58 g, 16.5 mmol) in dichloromethane (100 mL) and stirred at −78° C. for 1 h. Then Hunig base (8.5 g, 66 mmol) was added and the reaction mixture was warmed up to rt over 3 h. The solvent was removed and ethyl acetate (500 mL) was added. The mixture was washed with sodium carbonate solution, H$_2$O, and dried (Na$_2$SO$_4$), and concentrated in vacuo. 3.4 g of product was obtained as the title compound.

Step L (3): tert-Butyl 3-((1S,2S)-2-(3,5-difluorobenzyl)-3-((S)-4-benzyl-2-oxooxazolidin-3-yl)-1-hydroxy-3-oxopropyl)morpholine-4-carboxylate. To a solution of (S)-4-benzyl-3-(3-(3,5-difluorophenyl)propanoyl)oxazolidin-2-one (Preparation M, 6.0 g, 17.4 mmol) in CH$_2$Cl$_2$ (200 mL) at −78° C. was added Bu$_2$BOTf (20.5 ml, 20.5 mmol, 1M in CH$_2$Cl$_2$) and Hunig's base (5.1 g, 39.5 mmol). The resulting mixture was brought up to 0° C. over 15 min. and cooled back to −78° C. A solution of tert-butyl 3-formylmorpholine-4-carboxylate (step L (2), 3.4 g, 15.8 mmol) in CH$_2$Cl$_2$ (200 mL) was added. When the addition was complete, the mixture was allowed to warm to and stirred at rt overnight. Dichloromethane (500 mL) was added and the mixture was washed with H$_2$O, dried and concentrated in vacuo. The crude mixture was purified by silica gel Flash Chromatography (0% to 30% to 50% to 70% EtOAc/Hexane step gradient) to give 5.6 g of the title compound (63% yield): MS (ESI) (M+Na)$^+$ 583.21.

Step L (4): (2S,3S)-2-(3,5-Difluorobenzyl)-3-(4-(tert-butoxycarbonyl)morpholin-3-yl)-3-hydroxypropanoic acid. To a solution of tert-butyl 3-((1S,2S)-2-(3,5-difluorobenzyl)-3-((S)-4-benzyl-2-oxooxazolidin-3-yl)-1-hydroxy-3-oxopropyl)morpholine-4-carboxylate (step L (3), 2.8 g, 5 mmol) in THF (60 mL) was added a solution of LiOH (240 mg, 10 mmol) in H$_2$O (10 mL), then 30% H$_2$O$_2$ (5.7 g, 50 mmol) was added at 0° C. This reaction mixture was warmed up to rt and stirred at rt overnight. THF was removed and ethyl ether (200 mL) was added. The mixture was washed with 1N NaOH (150 mL) twice. The aqueous layer was treated with conc. HCl to pH=1 and extracted with ethyl acetate (300 mL) twice. The organic layers were dried (Na$_2$SO$_4$), and concentrated in vacuo to give 1.6 g of the title compound (80% yield) which was ready for next step without purification. MS (ESI) (M+Na)$^+$ 424.13.

Step L (5): tert-Butyl 3-((4S,5S)-4-(3,5-difluorobenzyl)-2-oxooxazolidin-5-yl)morpholine-4-carboxylate. To a solution of (2S,3S)-2-(3,5-difluorobenzyl)-3-(4-(tert-butoxycarbonyl)morpholin-3-yl)-3-hydroxypropanoic acid (step L (6), 1.6 g, 4 mmol) in toluene (100 mL) was added diphenylphosphoryl azide (1.65 g, 6 mmol) and triethyl amine (1.01 g, 10 mmoL). This reaction mixture was stirred at 80° C. for 4 h. Ethyl acetate (500 mL) was added. The mixture was washed with sodium carbonate solution, H$_2$O, dried over Na$_2$SO$_4$ and concentrated. The crude mixture was purified by silica gel Flash Chromatography (0% to 20% to 30% to 50% to 70% EtOAc/Hexane step gradient) to give 800 mg of the title compound: MS (ESI) (M−H)$^−$ 397.12.

Step L (6): (4S,5S)-4-(3,5-Difluorobenzyl)-5-(morpholin-3-yl)oxazolidin-2-one. A solution of tert-butyl 3-((4S,5S)-4-(3,5-difluorobenzyl)-2-oxooxazolidin-5-yl)morpholine-4-carboxylate (step L (5), 230 mg) in CH$_2$Cl$_2$ (4 mL) was treated with TFA (3 mL). This reaction mixture was stirred at rt for 1.5 h. The mixture was then concentrated in vacuo. Diethyl ether (50 mL) was added and the mixture was washed with 1N HCl solution (40 mL) twice. Aqueous layer was neutralized with 50% aqueous NaOH to pH=12. The mixture was extracted with ethyl acetate (80 mL) twice. The combined organic layers were dried (Na$_2$SO$_4$), and concentrated in vacuo to give 180 mg of the title compound: MS (ESI) (M+H)$^+$ 299.17.

Step L (7): (4S,5S)-4-(3,5-Difluorobenzyl)-5-((R)-4-benzhydrylmorpholin-3-yl)oxazolidin-2-one. To a solution of (4S,5S)-4-(3,5-difluorobenzyl)-5-(morpholin-3-yl)oxazolidin-2-one (step L (6), 180 mg, 0.6 mmol) in acetonitrile (5 mL) were added potassium carbonate (248 mg, 1.8 mmol) and bromodiphenylmethane (296 mg, 1.2 mmol). This mixture was stirred at 100° C. for 1.5 h. Solvent was removed and the crude mixture was purified by silica gel Flash Chromatography (0% to 20% to 40% to 65% EtOAc/Hexane step gradient) to give 85 mg of the title compound (29% yield):
$^1$H NMR (CDCl$_3$, 500 MHz) δ 2.14 (1H, m), 2.76 (2H, d, J=15 Hz), 2.98 (1H, d, J=5 Hz), 3.15 (1H, m), 3.52 (1H, m), 3.67 (1H, m), 3.87-3.94 (3H, m), 5.23 (2H, d, J=10 Hz), 5.31 (1H, m), 6.56 (2H, d, J=5 Hz), 6.70 (1H, m), 7.16 (1H, d, J=5 Hz), 7.21-7.37 (7H, m), 7.41 (2H, d, J=10 Hz). MS (ESI) (M+H)$^+$ 465.14.

Step L (8): (1S,2S)-2-Amino-1-((R)-4-benzhydrylmorpholin-3-yl)-3-(3,5-difluorophenyl)propan-1-ol. To a solution of (4S,5S)-4-(3,5-difluorobenzyl)-5-((R)-4-benzhydrylmorpholin-3-yl)oxazolidin-2-one (step L (7), 85 mg, 0.18 mmol) in EtOH (2 mL) was added a solution of LiOH (66 mg, 2.75 mmol) in H$_2$O (1 mL). This reaction mixture was brought to 98° C. and stirred for overnight. Solvent was removed and 1N HCl solution (50 mL) was added to the mixture and washed with diethyl ether. The aqueous phase was basified with 50% aqueous NaOH solution. This mixture was extracted with ethyl acetate. The combined organic layer was dried (Na$_2$SO$_4$), and concentrated in vacuo to give 80 mg of the title compound: $^1$H NMR (CDCl$_3$, 500 MHz) δ 1.94-2.06 (3H, m), 2.30 (1H, dd, J=10, 15 Hz), 2.51-2.59 (1H, m), 2.73-2.81 (1H, m), 2.90 (1H, m), 2.95 (1H, m), 3.08 (1H, m), 3.70 (1H, m), 3.80 (1H, dt, J=5, 10 Hz), 3.91 (1H, m), 4.09 (1H, m), 4.14 (1H, m), 5.05 (1H, s), 6.60-6.68 (3H, m), 7.15-7.31 (6H, m), 7.37 (2H, d, J=10 Hz), 7.42 (2H, d, J=5 Hz). MS (ESI) (M+H)$^+$ 439.20.

Preparation M (S)-4-benzyl-3-(3-(3,5-difluorophenyl)propanoyl)oxazolidin-2-one

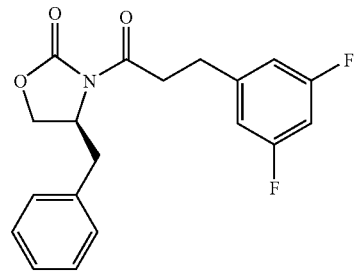

Step M (1): 3,5-difluorophenylhydrocinnamic acid. Commercial 3,5-difluorocinnamic acid (50.0 g, 0.271 mol) was dissolved in a mixture of 800 mL of ethyl acetate and 200 mL of methanol and added to a prewetted bed (methanol) of 5 g of 5% palladium on carbon. The mixture was placed under 40 psi of hydrogen in a Parr apparatus for 30 min, and the hydrogen pressure refilled until it stabilized. After an additional 30 min, the suspension was filtered through a bed of Celite and concentrated to a crude oil which solidified upon standing. This material was carried onto the next step without further purification.

Step M (2): 3,5-difluorophenylhydrocinnamoyl chloride. To a solution of 3,5-difluorophenylhydrocinnamic acid (step M (1), 10 g, 54 mmol) in 250 mL of $CH_2Cl_2$ was added 2.5 mL of DMF. To this solution was added dropwise oxalyl chloride (6.6 mL, 75 mmol, vigorous gas evolution) and the resulting solution was then stirred at rt for 2 h and then concentrated to a crude oil which was used in the next step without further purification.

Step M (3): (S)-4-benzyl-3-(3-(3,5-difluorophenyl)propanoyl)oxazolidin-2-one. (S)-4-benzyloxazolidin-2-one (10.5 g, 59 mmol) was dissolved in 200 mL of THF and chilled to −78° C. A solution of n-butyllithium in pentane (55.6 mL, 1.18 M, 65 mmol) was then added dropwise. After stirring for an additional 30 min at −78° C., the solution was allowed to come to 0° C. Separately, the acid chloride prepared in step M (2) was dissolved in 100 mL of THF and chilled to −78° C. The oxazolidinone anion solution from above was added dropwise to the acid chloride solution, and upon completion of the addition, the reaction mixture was allowed to warm to rt and stir for 2 h. The reaction solution was then partitioned between water and ethyl acetate and the organic layer was separated and dried with brine and $MgSO_4$ and then concentrated. The crude product was then recrystallized from 95% EtOH to provide white needles. $^1$H NMR (500 MHz, $CDCl_3$) δ ppm 2.77 (dd, J=13.43, 9.46 Hz, 1 H) 3.00 (m, 2 H) 3.25 (m, 3 H) 4.18 (m, 2 H) 4.67 (m, 1 H) 6.64 (m, J=9.08, 9.08, 2.29, 2.14 Hz, 1 H) 6.79 (dd, J=8.24, 1.83 Hz, 2 H) 7.16 (d, J=6.71 Hz, 2 H) 7.27 (m, 1 H) 7.32 (t, J=7.17 Hz, 2 H).

Preparation N (2R,4R)-tert-butyl 2-((1S,2S)-2-((S)-2-((S)-3-acetamido-3-((R)-sec-butyl)-2-oxopyrrolidin-1-yl)-4-phenylbutanamido)-1-(tert-butyldimethylsilyloxy)-3-(3,5-difluorophenyl)propyl)-4-hydroxypyrrolidine-1-carboxylate

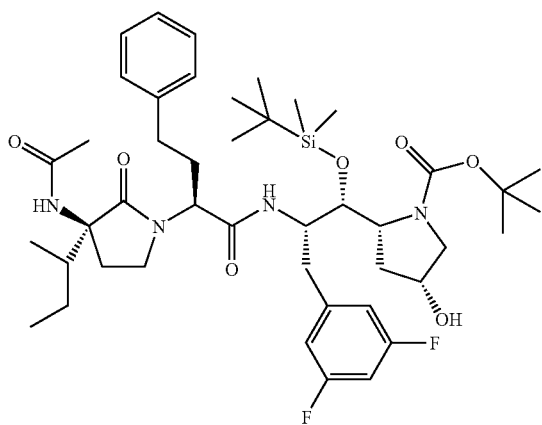

Step N (1): Preparation of (2R,4R)-tert-butyl 2-((1S,2S)-2-(3,5-difluorobenzyl)-3-((S)-4-benzyl-2-oxooxazolidin-3-yl)-1-(tert-butyldimethylsilyloxy)-3-oxopropyl)-4-(allyloxy)pyrrolidine-1-carboxylate. To a solution of the product from step C (5), (2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine-1-carboxylate, (10.0 g, 16.7 mmol), in $CH_2Cl_2$ (50 mL) at −30° C. was added 2,6-lutidine (2.91 mL, 25.1 mmol). A solution of tert-butyl dimethylsilyl trifluoromethanesulfonate (4.6 mL, 20 mmol) and 2,6-lutidine (2.91 mL, 25.1 mmol) in $CH_2Cl_2$ (15 mL) was added slowly, keeping the reaction below −25° C. during the addition. When the addition was complete, the reaction was allowed to warm to 0° C., and was stirred at this temperature for 3 hours. The mixture was then washed with 0.1 M HCl, dried over $MgSO_4$, and filtered. The solution was then concentrated in vacuo. Silica gel purification (0 to 30% EtOAc/Hexane) afforded a clear, colorless oil (8.57 g, 72% yield). $^1$H NMR ($CDCl_3$, 500 MHz) δ 0.04-0.22 (6H, m), 0.96 (9H, s), 1.47 (9H, s), 2.08-2.36 (3H, m), 2.83-3.15 (3H, m), 3.16-3.29 (1H, m), 3.65-3.83 (1H, m), 3.87-4.06 (6H, m), 4.39-4.46 (1H, m), 4.47-4.62 (2H, m), 5.10-5.18 (1H, m), 5.25 (1H, d, J=17.1 Hz), 5.82-5.93 (1H, m), 6.56-6.66 (1H, m), 6.72-7.04 (4H, m), 7.19-7.30 (3H, m).

Step N (2): Preparation of (2S,3S)-2-(3,5-difluorobenzyl)-3-((2R,4R)-4-(allyloxy)-1-(tert-butoxycarbonyl)pyrrolidin-2-yl)-3-(tert-butyldimethylsilyloxy)propanoic acid. To a solution of (2R,4R)-tert-butyl 2-((1S,2S)-2-(3,5-difluorobenzyl)-3-((S)-4-benzyl-2-oxooxazolidin-3-yl)-1-(tert-butyldimethylsilyloxy)-3-oxopropyl)-4-(allyloxy)pyrrolidine-1-carboxylate (Step N (1), 500 mg, 700 mmol) in THF (12.5 mL) was added a solution of LiOH (33.6 mg, 1.4 mmol) in water (3 mL), then 30% $H_2O_2$ (1.1 mL). the mixture was stirred at room temperature for 2 hours. A saturated solution of $Na_2SO_3$ was then added slowly. After stirring for 15 min, 1 N HCl was added to make the mixture acidic (pH~2). The mixture was extracted 3 times into $CH_2Cl_2$, dried over $MgSO_4$, filtered and concentrated in vacuo. The residue was purified by flash chromatography (0 to 10% MeOH/$CHCl_3$ to afford a clear, colorless oil (360 mg, 93% yield). $^1$H NMR ($CDCl_3$, 300 MHz) (mixture of Boc rotamers) δ −0.06-0.15 (6H, m), 0.81-1.01 (9H, m), 1.29-1.52 (9H, m), 1.98-2.31 (2H, m), 2.39-2.55 (1H, m), 2.65-3.15 (3H, m), 3.54-4.11 (5H, m), 4.34-4.58 (1H, m), 5.08-5.32 (2H, m), 5.71-5.95 (1H, m), 6.52-6.85 (3H, m). HPLC retention time: 2.56 min (method D). MS (ESI) (M+H)$^+$ 556.31.

Step N (3): Preparation of (2R,4R)-tert-butyl 4-(allyloxy)-2-((1S,2S)-2-(benzyloxycarbonyl)-1-(tert-butyldimethylsilyloxy)-3-(3,5-difluorophenyl)propyl)pyrrolidine-1-carboxylate. To a solution of (2S,3S)-2-(3,5-difluorobenzyl)-3-((2R,4R)-4-(allyloxy)-1-(tert-butoxycarbonyl)pyrrolidin-2-yl)-3-(tert-butyldimethylsilyloxy)propanoic acid (Step N (2), 2.20 g, 3.96 mmol) in toluene (250 mL) was added diisopropylethylamine (1.03 mL, 5.94 mmol) and diphenylphosphoryl azide (1.03 mL, 4.75 mmol). The mixture was brought to 75° C. and stirred for 4 h. Diisopropylethylamine (3.45 mL, 19.8 mmol) and benzyl alcohol (1.03 mL, 9.9 mmol) were then added, and the mixture heated for an additional 5 h. The mixture was concentrated, and the residue taken up in EtOAc. The solution was washed with saturated $NaHCO_3$, brine, dried over $MgSO_4$, and concentrated in vacuo. Flash chromatography (0 to 30% EtOAc/Hexane) gave a clear, colorless oil (1.08 g, 41% yield). $^1$H NMR ($CDCl_3$, 300 MHz) δ 0.04 (6H, s), 0.91 (9H, s), 1.47 (9H, s), 1.86 (2H, J=5.9 Hz, t), 2.40 (1H, J=12.3 Hz, app t), 3.14 (1H, J=4.0, 12.3 Hz, dd), 3.68-4.20 (6H, m), 4.84-5.05 (2H, m), 5.10-5.38 (3H, m), 5.75-5.94 (1H, m), 6.53-6.79 (3H, m), 7.11-7.35 (5H, m). HPLC retention time: 2.76 min (method D). MS (ESI) (M+H)$^+$ 661.34.

Step N (4): Preparation of (2R,4R)-tert-butyl 2-((1S,2S)-2-(benzyloxycarbonyl)-1-(tert-butyldimethylsilyloxy)-3-(3,5-difluorophenyl)propyl)-4-hydroxypyrrolidine-1-carboxylate. To a solution of (2R,4R)-tert-butyl 4-(allyloxy)-2-((1S,2S)-2-(benzyloxycarbonyl)-1-(tert-butyldimethylsilyloxy)-3-(3,5-difluorophenyl)propyl)pyrrolidine-1-carboxylate (Step N (3), 1.08 g, 1.64 mmol) in 10% water/ethanol (15 mL) was added Wilkinson's catalyst (114 mg, 123 mmol). The mixture was stirred at reflux for 5 h. The reaction was allowed to cool to room temperature. A buffer solution (pH 10, 5 mL) was added, then KMnO$_4$ (518 mg, 3.28 mmol) in minimal water was added slowly. An additional 10 mL EtOH was added, and the mixture stirred at rt for 30 min. The mixture was filtered through Celite and concentrated in vacuo. Silica gel chromatography (0 to 75% EtOAc/Hexane) afforded a clear, colorless oil (535 mg, 53% yield). $^1$H NMR (CDCl$_3$, 300 MHz) δ 0.07-0.21 (6H, m), 0.93 (9H, s), 1.47 (9H, s), 2.06-2.19 (1H, br s), 2.30-2.46 (1H, m), 3.11-3.40 (2H, m), 3.46-3.69 (1H, m), 3.82-3.99 (1H, br s), 4.05-4.38 (3H, m), 4.74-5.05 (2H, m), 6.54-6.77 (3H, m), 7.10-7.37 (5H, m). HPLC retention time: 2.49 min (method D). MS (ESI) (M+H)$^+$ 621.35.

Step N (5): Preparation of (2R,4R)-tert-butyl 2-((1S,2S)-2-amino-1-(tert-butyldimethylsilyloxy)-3-(3,5-difluorophenyl)propyl)-4-hydroxypyrrolidine-1-carboxylate. To a solution of (2R,4R)-tert-butyl 2-((1S,2S)-2-(benzyloxycarbonyl)-1-(tert-butyldimethylsilyloxy)-3-(3,5-difluorophenyl)propyl)-4-hydroxypyrrolidine-1-carboxylate (Step N (4), 1.04 g, 1.68 mmol) in Methanol was added 10% Pd/C. The mixture was shaken on a Parr apparatus at 50 psi H$_2$ for 2 h. The mixture was filtered, and concentrated in vacuo. Flash chromatography (EtOAc/Hexane gradient) afforded a clear, colorless oil (745 mg, 91% yield). $^1$H NMR (CDCl$_3$, 300 MHz) δ 0.07-0.22 (6H, m), 0.93 (9H, s), 1.47 (9H, s), 2.11-2.54 (3H, m), 2.98-3.18 (2H, m), 3.31 (2H, J=11.7 Hz, d), 3.40-3.64 (1H, m), 4.10-4.43 (3H, m), 6.56-6.80 (3H, m). HPLC retention time: 2.00 min (method D). MS (ESI) (M+H)$^+$ 487.27.

Step N (6): Preparation of (2R,4R)-tert-butyl 2-((1S,2S)-2-((S)-2-((S)-3-acetamido-3-((R)-sec-butyl)-2-oxopyrrolidin-1-yl)-4-phenylbutanamido)-1-(tert-butyldimethylsilyloxy)-3-(3,5-difluorophenyl)propyl)-4-hydroxypyrrolidine-1-carboxylate. To a solution of (S)-2-((S)-3-acetamido-3-((S)-sec-butyl)-2-oxopyrrolidin-1-yl)-4-phenylbutanoic acid (Preparation A, 547.2 mg, 1.52 mmol) in DMF (15 ml) was added HATU (696 mg, 1.83 mmol). A solution of (2R,4R)-tert-butyl 2-((1S,2S)-2-amino-1-(tert-butyldimethylsilyloxy)-3-(3,5-difluorophenyl)propyl)-4-hydroxypyrrolidine-1-carboxylate (Step N (5), 740 mg, 1.52 mmol) in DMF (1.0 ml) was then added, followed by N-methylmorpholine (586 μl, 5.33 mmol). The reaction mixture was stirred at rt for 2 h. pH 4 buffer was then added to quench. The mixture was extracted with ethyl acetate. The organic phase was washed with sat. aqueous NaCl, dried (MgSO$_4$), and concentrated in vacuo. Flash chromatography (silica gel, ethyl acetate/hexane gradient) gave 1.26 g (100% yield) of (2R,4R)-tert-butyl 2-((1S,2S)-2-((S)-2-((S)-3-acetamido-3-((R)-sec-butyl)-2-oxopyrrolidin-1-yl)-4-phenylbutanamido)-1-(tert-butyldimethylsilyloxy)-3-(3,5-difluorophenyl)propyl)-4-hydroxypyrrolidine-1-carboxylate as a clear, colorless oil. NMR (CDCl$_3$, 300 MHz) δ 0.05-0.27 (6H, m), 0.72 (3H, J=6.6 Hz, d), 0.95-1.04 (13H, m), 1.47 (9H, s), 1.62-1.75 (2H, m), 1.97 (3H, s), 2.02-2.40 (6H, m), 2.51-2.79 (3H, m), 2.90-2.99 (1H, m), 3.13-3.25 (1H, m), 3.35-3.44 (1H, m), 3.53-3.68 (1H, m), 3.73-4.08 (3H, m), 4.09-4.22 (1H, m), 4.24-4.39 (2H, m), 6.66-6.86 (3H, m), 7.11-7.31 (5H, m), 7.94 (1H, s), 8.25 (1H, J=9.5 Hz, d). HPLC retention time: 2.52 min (method D). MS (ESI) (M+H)$^+$ 829.41.

Preparation O (2R,4R)-tert-butyl 4-(allyloxy)-2-((1S,2S)-2-(benzyloxycarbonyl)-1-(tert-butyldimethylsilyloxy)-3-(3,5-difluorophenyl)propyl)pyrrolidine-1-carboxylate

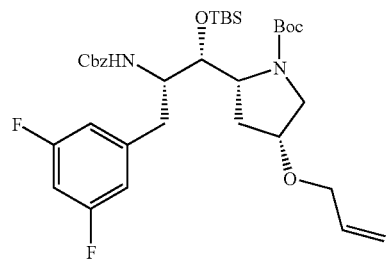

Step O (1): (2R,4R)-1-(tert-butoxycarbonyl)-4-hydroxypyrrolidine-2-carboxylic acid. To a suspension of H-D-Cis-Hyp-OH (purchased from Aldrich, 10.0 g, 76.3 mmol) in 2:1 THF:H$_2$O (125 ml) was added a 2.5 molar aqueous sodium hydroxide solution (42.0 ml). To this mixture was added a solution of Di-tert-butyldicarbonate (22.6 g, 103.6 mmol) in 2:1 THF: H$_2$O (125 ml). The resulting reaction mixture was stirred at rt for 18 h. The mixture was then concentrated in vacuo to remove the THF. To the remaining aqueous mixture was added a 10% aqueous potassium hydrogen sulfate solution (150 ml). The resulting mixture was extracted with ethyl acetate. The organic phase was washed with H$_2$O, sat. aqu. NaCl, dried (MgSO$_4$), and concentrated in vacuo. The resulting slightly yellow oil was crystallized from hot ethyl acetate to give 11.8 g (67%) of (2R,4R)-1-(tert-butoxycarbonyl)-4-hydroxypyrrolidine-2-carboxylic acid as a white solid: $^1$H NMR (CD$_3$OD, 300 MHz) δ 1.44 (9H, m), 1.99-2.09 (1H, m), 2.35-2.49 (1H, m), 3.32-3.35 (1H, m), 3.60 (1H, dd, J=6, 12 Hz), 4.25 (1H, dd, J=6, 12 Hz), 4.31-4.36 (1H, m).

Step O (2): (2R,4R)-4-(allyloxy)-1-(tert butoxycarbonyl)pyrrolidine-2-carboxylic acid. To a suspension of NaH (60% in oil, 5.84 g, 146 mmol) in DMF (125 ml) cooled to 0° C. was added a solution of (2R,4R)-1-(tert-butoxycarbonyl)-4-hydroxypyrrolidine-2-carboxylic acid (Step O (1), 13.5 g, 58.4 mmol) in THF (100 ml) dropwise. When the addition was complete, the mixture was allowed to come to rt and stir until gas evolution ceased (30-45 min.). To the reaction mixture was then added allyl bromide (5.05 ml, 58.4 mmol) dropwise. The resulting mixture was stirred at rt for 2 h. The reaction was quenched by the slow addition of 1N HCl (150 ml). pH 4 buffer was added and the mixture was extracted with ethyl acetate. The organic phase was washed with sat. aqu. NaCl, dried (MgSO$_4$), and concentrated in vacuo. Flash chromatography (silica gel, 0-20% methanol/chloroform) gave 13.06 g (83%) of (2R,4R)-4-(allyloxy)-1-(tert-butoxycarbonyl)pyrrolidine-2-carboxylic acid as a clear, colorless oil: $^1$H NMR (CD$_3$OD, 300 MHz) δ 1.44 (9H, m), 2.18-2.44 (2H, m), 3.42 (1H, dd, J=3, 12 Hz), 3.59 (1H, dd, J=6, 12 Hz), 3.95-3.96 (2H, m), 4.10-4.14 (1H, m), 4.26-4.34 (1H, m), 5.12 (1H, d, J=12 Hz), 5.26 (1H, d, J=18 Hz), 5.80-5.92 (1H, m). HPLC retention time: 1.21 min (method A). MS (ESI) (M+H)$^+$ 272.17.

Step O (3): Preparation of (2R,4R)-tert-butyl 4-(allyloxy)-2-(hydroxymethyl)pyrrolidine-1-carboxylate. A solution of (2R,4R)-4-(allyloxy)-1-(tert-butoxycarbonyl)pyrrolidine-2-carboxylic acid (Step O (2), 13.06 g, 48.2 mmol) in THF (250 ml) was cooled to 0° C. Hunig's base (12.6 ml, 72.3 mmol) and ethyl chloroformate (5.51 ml, 57.8 mmol) were added and the mixture was stirred at 0° C. for 15 min. The mixture was then allowed to come to rt and stir for 2 h. during which white ppt. formed. NaBH$_4$ (1.68 g, 44.28 mmol) was then added and the mixture was again cooled to 0° C. To the resulting mixture was added MeOH (179 ml) very slowly. The MeOH addition results in gas evolution and an exotherm. When the addition was complete, the mixture was allowed to come to rt and stir for 2 h. The reaction was then concentrated in vacuo and the residue was partitioned between 1N HCl and ethyl acetate. The organic phase was washed with sat. aqu. NaCl, dried (MgSO$_4$), and concentrated in vacuo. Flash chromatography (silica gel, 0-10% methanol/chloroform) gave 9.58 g (77%) of (2R,4R)-tert-butyl 4-(allyloxy)-2-(hydroxymethyl)pyrrolidine-1-carboxylate as a clear, colorless oil: $^1$H NMR (CD$_3$OD, 300 MHz) δ 1.43 (9H, s), 1.82 (1H, brd s), 2.18 (1H, m), 3.40-3.54 (2H, m), 3.66-3.69 (2H, m), 3.93-4.00 (5H, m), 5.16 (1H, dd, J=3, 9 Hz), 5.24 (1H, dd, J=3, 15 Hz), 5.78-5.91 (1H, m). HPLC retention time: 1.28 min (method A). MS (ESI) (M+H)$^+$ 258.19.

Step O (4): (2R,4R)-tert-butyl 4-(allyloxy)-2-formylpyrrolidine-1-carboxylate. To a solution of (2R,4R)-tert-butyl 4-(allyloxy)-2-(hydroxymethyl)pyrrolidine-1-carboxylate (Step O (3), 9.58 g, 37.28 mmol) in CH$_2$Cl$_2$ (500 ml) was added Dess Martin periodinane (32.0 g, 74.55 mmol). The resulting mixture was stirred at rt for 2 h. and then concentrated in vacuo. Flash chromatography (silica gel, 0-50% ethyl acetate/hexane) gave 7.39 g (78%) of (2R,4R)-tert-butyl 4-(allyloxy)-2-formylpyrrolidine-1-carboxylate as a slightly yellow oil: $^1$H NMR (CD$_3$OD, 300 MHz) δ 1.44 (9H, m), 2.01-2.35 (2H, m), 3.40-3.48 (1H, m), 3.55-3.70 (1H, m), 3.84-3.92 (2H, m), 4.04-4.20 (2H, m), 5.12-5.24 (2H, m), 5.74-5.87 (1H, m), 9.51-9.57 (1H, m). HPLC retention time: 1.39 min (method A). MS (ESI) (M+H+ CH$_3$OH)$^+$ 288.21.

Step O (5): 2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine 1-carboxylate. To a solution of (S)-4-benzyl-3-(3-(3,5-difluorophenyl)propanoyl)oxazolidin-2-one (Preparation M), 1.47 g, 4.27 mmol) in CH$_2$Cl$_2$ (15 ml) at −78° C. was added Bu$_2$BOTf (5.12 ml, 5.12 mmol, 1M in CH$_2$Cl$_2$) and Hunig's base (1.12 ml, 6.41 mmol). The resulting mixture was brought to 0° C. and stirred for 30 min. The mixture was again cooled to −78° C. and a solution of (2R,4R)-tert-butyl 4-(allyloxy)-2-formylpyrrolidine 1-carboxylate (Step O (4), 1.09 g, 4.27 mmol) in CH$_2$Cl$_2$ (10 ml) was added dropwise. When the addition was complete, the mixture was stirred at −78° C. for 5 min., then was allowed to warm to rt. After stirring at rt for 4 h. the mixture was concentrated in vacuo. Flash chromatography (silica gel, 0-75% ethyl acetate/hexane) gave 1.22 g (48%) of (2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine-1-carboxylate as a slightly yellow oil: $^1$H NMR (CDCl$_3$, 300 MHz) δ 1.49 (9H, s), 2.03-2.22 (2H, m), 2.31 (1H, d, J=12 Hz), 2.98 (1H, dd, J=3, 15 Hz), 3.07 (1H, t, J=12 Hz), 3.42-3.57 (3H, m), 3.97-4.11 (8H, m), 4.57 (2H, brd s), 5.17-5.30 (2H, m), 5.81-5.94 (1H, m), 6.61 (1H, t, J=9 Hz), 6.90 (2H, brd s), 7.00 (2H, brd s), 7.26 (3H, m). HPLC retention time: 2.04 min (method A). MS (ESI) (M+H)$^+$ 601.37.

Step O (6): (2S,3S)-2-(3,5-difluorobenzyl)-3-((2R,4R)-4-(allyloxy)-1-(tert-butoxycarbonyl)pyrrolidin-2-yl)-3-(tert-butyldimethylsilyloxy)propanoic acid. The compound of Step O (5), (2R,4R)-tert-butyl 2-((1S,2S)-2-(3,5-difluorobenzyl)-3-((S)-4-benzyl-2-oxooxazolidin-3-yl)-1-hydroxy-3-oxopropyl)-4-(allyloxy)pyrrolidine-1-carboxylate, 6.5 grams, 0.011 mmol) was dissolved in 30 mL of dichloromethane and treated with 5.6 mL (32 mmol) of DIEA, followed by 3.43 g (13.0 mmol) of tert-butyldimethylsilyl triflate. After 30 min, the reaction had gone to completion by tlc analysis eluting with 2:3 ethyl acetate:hexanes and was washed twice with a satd. NaHCO$_3$ solution and once with brine. The organic layer was dried and concentrated in vacuo to an oil. The crude product thus obtained was dissolved in 150 mL of THF and chilled to 0° C. A solution of 30% H$_2$O$_2$ in water (9 mL, 0.088 mmol) was then added, followed by a solution of lithium hydroxide (0.53 g, 0.022 mmol) dissolved in 40 mL of water. The reaction solution was allowed to warm to rt and stirred 16 h. The mixture was then diluted with 100 mL of ether and washed twice with a satd. NaHCO$_3$ solution and once with brine. The organic layer was dried and concentrated to an oil which was purified by silica gel chromatography eluting with 2:3 ethyl acetate:hexanes to provide 3.77 g (62%) of the desired title compound as a white foam. $^1$H NMR (400 MHz, CDCl$_3$) δ 0.07 (d, J=23.67 Hz, 6 H) 0.93 (s, 9 H) 1.35 (s, 9 H) 2.06 (m, 1 H) 2.22 (m, 1 H) 2.46 (m, 1 H) 2.78 (t, J=12.59 Hz, 1 H) 2.94 (m, 1 H) 3.08 (m, 1 H) 3.82 (m, 1 H) 3.97 (m, 4 H) 4.53 (d, J=6.80 Hz, 1 H) 5.15 (d, J=10.32 Hz, 1 H) 5.25 (dd, J=17.25, 1.13 Hz, 1 H) 5.86 (m, J=22.54, 10.70, 5.54 Hz, 1 H) 6.59 (t, J=9.06 Hz, 1 H) 6.64 (m, 1 H) 6.69 (d, J=6.55 Hz, 1 H).

Step O (7): (2R,4R)-tert-butyl 4-(allyloxy)-2-((1S,2S)-2-(benzyloxycarbonyl)-1-(tert-butyldimethylsilyloxy)-3-(3,5-difluorophenyl)propyl)pyrrolidine-1-carboxylate. The compound of step O (6) (3.77 g, 6.8 mmol) was dissolved in 20 mL of toluene, and treated with 1.31 g of DIEA (10.2 mmol), followed by 2.24 g (8.2 mmol) of DPPA. The reaction solution was heated to 70° C. for 4 h, then allowed to cool to rt. Excess DIEA (4.4 g, 34 mmol) was then added, followed by 1.83 g (17 mmol) of benzyl alcohol. The reaction solution was again heated to 70° C. for 16 h and then the solvent ws directly removed in vacuo. The residue was purified by flash chromatography eluting with a gradient of 2.5% to 10% ethyl acteate in hexanes to provide 2.5 g (56%) of the title compound of preparation O as a white foam.

MS (ESI, M+H)$^+$=661.26 $^1$H NMR (500 MHz, CDCl$_3$) δ 0.05 (m, 6 H) 0.91 (s, 9 H) 1.45 (d, J=24.41 Hz, 9 H) 2.14 (s, 1 H) 2.41 (m, 1 H) 3.14 (d, J=9.77 Hz, 2 H) 3.79 (s, 1 H) 3.95 (s, 4 H) 4.03 (d, J=5.80 Hz, 1 H) 4.13 (s, 1 H) 4.94 (d, J=12.51 Hz, 1 H) 5.00 (m, 1 H) 5.15 (d, J=10.68 Hz, 1 H) 5.24 (m, 1 H) 5.85 (m, 1 H) 6.60 (s, 1 H) 6.73 (d, J=5.80 Hz, 1 H) 7.27 (m, 8 H).

EXAMPLE 1

(S)-2-((R)-3-acetamido-3-isobutyl-2-oxopyrrolidin-1-yl)-N-((1R,2S)-3-(3,5-difluorophenyl)-1-hydroxy-1-((2R,4R)-4-propoxypyrrolidin-2-yl)propan-2-yl)-4-phenylbutanamide

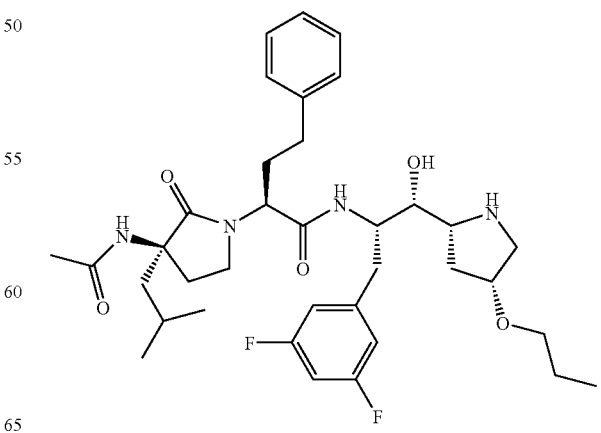

Step 1 (A): To a solution of (S)-2-((R)-3-acetamido-3-isobutyl-2-oxopyrrolidin-1-yl)-4-phenylbutanoic acid (Preparation B, 96 mg, 0.266 mmol) in DMF (1.5 ml) was added HATU (121 mg, 0.319 mmol). A solution of (1S,2S)-1-((2R,4R)-1-(4-methoxybenzyl)-4-(allyloxy)pyrrolidin-2-yl)-2-amino-3-(3,5-difluorophenyl)propan-1-ol (Preparation C, 115 mg, 0.266 mmol) in DMF (1.0 ml) was then added, followed by N-methylmorpholine (102 μl, 0.931 mmol). The reaction mixture was stirred at rt for 30 min. pH 4 buffer was then added to quench. The mixture was extracted with ethyl acetate. The organic phase was washed with sat. aqueous NaCl, dried (MgSO$_4$), and concentrated in vacuo. Flash chromatography (silica gel, 75-100% ethyl acetate/hexane) gave 114 mg (55%) of (S)-N-((1S,2S)-1-((2R,4R)-1-(4-methoxybenzyl)-4-(allyloxy)pyrrolidin-2-yl)-3-(3,5-difluorophenyl)-1-hydroxypropan-2-yl)-2-((R)-3-acetamido-3-isobutyl-2-oxopyrrolidin-1-yl)-4-phenylbutanamide as a clear, colorless oil:

$^1$H NMR (CDCl$_3$, 500 MHz) δ 1.00 (6H, t, J=10 Hz), 1.24 (1H, t, J=7.5 Hz), 1.54 (1H, dd, J=5, 15 Hz), 1.70 (1H, dd, J=5, 15 Hz), 1.86 (1H, m), 1.91 (3H, s), 2.04 (2H, m), 2.14-2.22 (2H, m), 2.28 (1H, dd, J=5, 10 Hz), 2.32-2.38 (1H, m), 2.49 (1H, m), 2.53-2.61 (1H, m), 2.64-2.69 (1H, m), 2.78 (2H, dd, J=10, 15 Hz), 3.02 (1H, d, J=0 Hz), 3.12-3.23 (3H, m), 3.32 (1H, dt, J=5, 10 Hz), 3.66 (1H, q, J=5 Hz), 3.76 (3H, s), 3.81-3.85 (2H, m), 3.88-3.96 (3H, m), 4.02 (1H, dq, J=5, 10 Hz), 5.11 (1H, d, J=10 Hz), 5.21 (1H, d, J=20 Hz), 5.83 (1H, m), 5.91 (1H, s), 6.55 (1H, t, J=7.5 Hz), 6.80 (2H, d, J=10 Hz), 6.84 (2H, d, J=5 Hz), 7.06 (1H, d, J=5 Hz), 7.13-7.18 (5H, m), 7.25 (2H, t, J=7.5 Hz). HPLC retention time: 1.87 min (method A). MS (ESI) (M+H)$^+$ 775.47.

Step 1 (B): Preparation of (S)-2-((R)-3-acetamido-3-isobutyl-2-oxopyrrolidin-1-yl)-N-((1R,2S)-3-(3,5-difluorophenyl)-1-hydroxy-1-((2R,4R)-4-propoxypyrrolidin-2-yl)propan-2-yl)-4-phenylbutanamide. To a solution of (S)-N-((1S,2S)-1-((2R,4R)-1-(4-methoxybenzyl)-4-(allyloxy)pyrrolidin-2-yl)-3-(3,5-difluorophenyl)-1-hydroxypropan-2-yl)-2-((R)-3-acetamido-3-isobutyl-2-oxopyrrolidin-1-yl)-4-phenylbutanamide (Step 1 (A), 55 mg, 0.071 mmol) in MeOH (5 ml) was added a catalytic amount of Pd(OH)$_2$. The reaction mixture was stirred under 1 atm. of H$_2$ for 18 h. The mix was then filtered through Celite and concentrated in vacuo. Flash chromatography (silica gel, 0-30% methanol/chloroform) gave 29.9 mg (64%) of (S)-2-((R)-3-acetamido-3-isobutyl-2-oxopyrrolidin-1-yl)-N-((1R,2S)-3-(3,5-difluorophenyl)-1-hydroxy-1-((2R,4R)-4-propoxypyrrolidin-2-yl)propan-2-yl)-4-phenylbutanamide, the title compound of Example 1 as an opaque glass: $^1$H NMR (CDCl$_3$, 500 MHz) δ 0.88 (3H, t, J=7.5 Hz), 1.00 (6H, dd, J=5, 7.5 Hz), 1.54 (3H, q, J=5 Hz), 1.69 (1H, dd, J=5, 15 Hz), 1.85 (1H, m), 1.92-1.97 (1H, m), 1.99 (3H, s), 2.11-2.17 (3H, m), 2.36-2.48 (3H, m), 2.52-2.57 (1H, m), 2.72 (1H, dd, J=10, 15 Hz), 2.92 (1H, dd, J=5, 15 Hz), 3.12-3.19 (3H, m), 3.29-3.42 (4H, m), 3.62 (1H, dd, J=5, 10 Hz), 3.98 (1H, m), 4.09-4.15 (1H, m), 4.63 (2H, brd s), 6.06 (1H, s), 6.52 (1H, m), 6.84 (2H, d, J=5 Hz), 7.10 (2H, d, J=5 Hz), 7.15 (1H, t, J=7.5 Hz), 7.24 (2H, t, J=7.5 Hz), 7.54 (1H, d, J=10 Hz). HPLC retention time: 1.69 min (method A). MS (ESI) (M+H)$^+$ 657.38.

EXAMPLE 2

(S)-2-((R)-3-acetamido-3-secbutyl-2-oxopyrrolidin-1-yl)-N-((1R,2S)-3-(3,5-difluorophenyl)-1-hydroxy-1-((2R,4R)-4-propoxypyrrolidin-2-yl)propan-2-yl)-4-phenylbutanamide

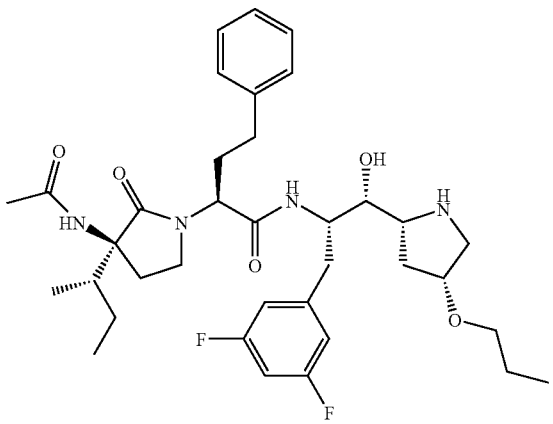

Step 2 (A): In a manner similar to the preparation of the compound of step 1 (A), Preparation A and Preparation C were coupled to provide the compound of step 2 (A).

Step 2 (B): (S)-2-((R)-3-acetamido-3-secbutyl-2-oxopyrrolidin-1-yl)-N-((1R,2S)-3-(3,5-difluorophenyl)-1-hydroxy-1-((2R,4R)-4-propoxypyrrolidin-2-yl)propan-2-yl)-4-phenylbutanamide. In a manner similar to the preparation of the compound of Example 1, Step 1 (B), the compound of step 2 (A) was hydrogenated to provide the title compound of Example 2. $^1$H NMR (CDCl$_3$, 300 MHz) δ 0.87 (6H, t, J=6 Hz), 0.97 (3H, t, J=6 Hz), 1.03-1.16 (1H, m), 1.48-1.64 (3H, m), 1.71-1.78 (1H, m), 1.97 (3H, s), 2.02-2.32 (6H, m), 2.43 (2H, t, J=6 Hz), 2.68 (1H, dd, J=12, 15 Hz), 3.00 (1H, dd, J=6, 12 Hz), 3.09-3.41 (5H, m), 3.44-3.54 (3H, m), 3.78 (1H, dd, J=3, 9 Hz), 4.02-4.11 (2H, m), 5.78 (2H, brd s), 6.35 (1H, s), 6.51 (1H, tt, J=3, 9 Hz), 6.82 (2H, d, J=6 Hz), 7.06 (2H, d, J=6 Hz), 7.15 (1H, t, J=6 Hz), 7.23 (2H, t, J=6 Hz), 7.90 (1H, d, J=9 Hz). HPLC retention time: 1.73 min (method A). MS (ESI) (M+H)$^+$ 657.29.

EXAMPLE 3

(S)-((1R,2S)-3-(3,5-difluorophenyl)-1-hydroxy-1-((2R,4R)-4-propoxypyrrolidin-2-yl)propan-2-yl) 2-((S)-3-butyl-2-oxopyrrolidin-1-yl)-4-phenylbutanoate

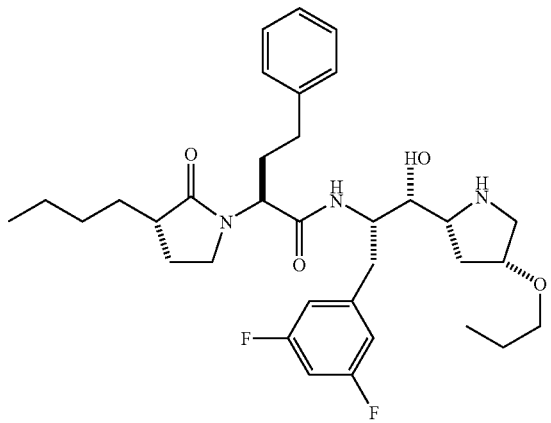

Step 3 (A): (S)-((1R,2S)-1-((2R,4R)-1-(4-methoxybenzyl)-4-(allyloxy)pyrrolidin-2-yl)-3-(3,5-difluorophenyl)-1- hydroxypropan-2-yl) 2-((S)-3-butyl-2-oxopyrrolidin-1-yl)-4-phenylbutanoate. To a solution of the compound of Preparation G (42.3 mg, 139 μmol) and the compound of Preparation C (50.3 mg, 116 μmol) in DMF (1.29 mL) was added HATU (66.4 mg, 140 μmol) and N-Methyl morpholine (53.5 μL, 410 μmol). The reaction was stirred at rt until LC showed conversion to product (<45 min). The crude reaction mixture was injected onto a reverse-phase HPLC column (XTERRA S5 19×100 mm, gradient from 10% MeOH/H$_2$O to 90% MeOH/H$_2$O, containing 0.1% TFA) to afford, after solvent removal, pure product. $^1$H NMR (500 MHz, CDCl$_3$) δ ppm 0.85-0.94 (m, 3 H) 1.06-1.16 (m, 1 H) 1.23-1.43 (m, 7 H) 1.70-2.61 (m, 9 H) 2.74 (dd, J=14.95, 9.46 Hz, 1 H) 2.93-3.01 (m, 1 H) 3.07-3.28 (m, 3 H) 3.37-3.51 (m, 1 H) 3.77 (s, 3 H) 3.81-3.99 (m, 4 H) 4.06-4.16 (m, 1 H) 4.35-4.44 (m, 1 H) 5.14 (d, J=10.38 Hz, 1 H) 5.20-5.28 (m, 1 H) 5.80-5.91 (m, 1 H) 5.97 (d, J=8.85 Hz, 1 H) 6.58-6.65 (m, 1 H) 6.72 (d, J=6.10 Hz, 2 H) 6.83 (d, J=8.55 Hz, 2 H) 7.10-7.32 (m, 7 H). HPLC retention time: 2.08 min (method B). MS (ESI) (M+H)$^+$ 718.

Step 3 (B): (S)-((1R,2S)-3-(3,5-difluorophenyl)-1-hydroxy-1-((2R,4R)-4-propoxypyrrolidin-2-yl)propan-2-yl) 2-((S)-3-butyl-2-oxopyrrolidin-1-yl)-4-phenylbutanoate. To a solution of the compound of step 3 (A) (70.7 mg, 98.6 μmol) in 1:1 MeOH/EtOH (4 mL) was added 10% Pd/C. The flask was capped with a H$_2$ balloon, and after 3 pump/flush cycles, the reaction was allowed to stir under H$_2$ overnight. The reaction was filtered through a 0.45 μm filter, and solvents removed in vacuo. Silica gel chromatography (0% to 25% MeOH/CHCl$_3$) afforded the title compound as a pure product (43.5 mg, 74% yield). $^1$H NMR (500 MHz, CD$_3$OD) δ ppm 0.89-0.98 (m, 6 H) 1.17-1.26 (m, 1 H) 1.28-1.50 (m, 5 H) 1.53-1.63 (m, 2 H) 1.73-1.82 (m, 1 H) 1.91-2.13 (m, 4 H) 2.27-2.38 (m, 2 H) 2.44-2.52 (m, 2 H) 2.72 (dd, J=14.34, 11.29 Hz, 1 H) 3.03-3.10 (m, 1 H) 3.14-3.46 (m, 5 H) 3.52 (dt, J=8.7, 3.2 Hz 1 H) 3.82 (dd, J=8.55, 3.36 Hz, 1 H) 4.02-4.10 (m, 1 H) 4.14-4.20 (m, 1 H) 4.39 (dd, J=8.70, 6.56 Hz, 1 H) 6.70-6.77 (m, 1 H) 6.83 (d, J=6.10 Hz, 2 H) 7.10-7.19 (m, 3 H) 7.21-7.28 (m, 2 H). HPLC retention time: 1.86 min (method C). MS (ESI) (M+H)$^+$ 600.

EXAMPLE 4

(S)-((1R,2S)-3-(3,5-difluorophenyl)-1-hydroxy-1-((2R,4R)-4-propoxypyrrolidin-2-yl)propan-2-yl) 2-((S)-3-butyl-2-oxopyrrolidin-1-yl)propanoate

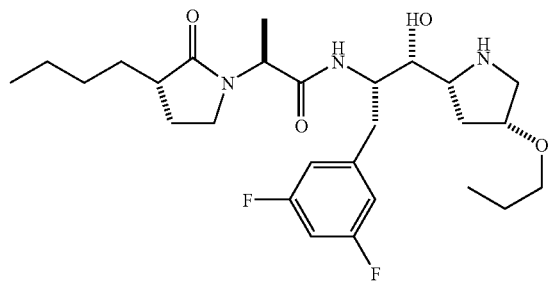

Step 4 (A): (S)-((1R,2S)-1-((2R,4R)-1-(4-methoxybenzyl)-4-(allyloxy)pyrrolidin-2-yl)-3-(3,5-difluorophenyl)-1-hydroxypropan-2-yl) 2-((S)-3-butyl-2-oxopyrrolidin-1-yl)propanoate. To a solution of the compound of Preparation H (50.0 mg, 235 μmol) and the compound of Preparation C (84.7 mg, 196 μmol) in DMF (2.2 mL) was added HATU (112 mg, 295 μmol) and N-Methyl morpholine (90 μL, 820 μmol). The reaction was stirred at rt until LC showed conversion to product (<1 h). The crude reaction mixture was injected onto a reverse-phase HPLC column (XTERRA S5 19×100 mm, gradient from 10% MeOH/H$_2$O to 90% MeOH/H$_2$O, containing 0.1% TFA) to afford, after solvent removal, pure product. HPLC retention time: 1.65 min (method C). MS (ESI) (M+H)$^+$ 628.

Step 4 (B): (S)-((1R,2S)-3-(3,5-difluorophenyl)-1-hydroxy-1-((2R,4R)-4-propoxypyrrolidin-2-yl)propan-2-yl) 2-((S)-3-butyl-2-oxopyrrolidin-1-yl)propanoate. To a solution of the compound of step 4 (A) in 1:1 MeOH/EtOH was added 10% Pd/C. The flask was capped with a H$_2$ balloon, and after 3 pump/flush cycles, the reaction was allowed to stir under H$_2$ overnight. The reaction was filtered through a 0.45 μm filter, and solvents removed in vacuo. Silica gel chromatography (0% to 25% MeOH/CHCl$_3$) afforded pure product of the title compound. $^1$H NMR (500 MHz, CD$_3$OD) δ ppm 0.88-0.99 (m, 6 H) 1.17-1.43 (m, 7 H) 1.46-1.66 (m, 3 H) 1.73-1.84 (m, 1 H) 1.99-2.09 (m, 1 H) 2.09-2.20 (m, 1 H) 2.29-2.43 (m, 2 H) 2.75 (dd, J=14.19, 11.14 Hz, 1 H) 3.00-3.10 (m, 1 H) 3.20-3.49 (m, 7 H) 3.61-3.72 (m, 1 H) 3.87-3.93 (m, 1 H) 3.94-4.05 (m, 1 H) 4.17-4.29 (m, 1 H) 4.38 (q, J=7.32 Hz, 1 H) 6.70-6.90 (m, 3 H). HPLC retention time: 1.57 min (method C). MS (ESI) (M+H)$^+$ 510.

EXAMPLE 5

(S)-((1R,2S)-3-(3,5-difluorophenyl)-1-hydroxy-1-((2R,4R)-4-propoxypyrrolidin-2-yl)propan-2-yl) 2-((R)-3-isopropyl-2-oxopyrrolidin-1-yl)-4-phenylbutanoate

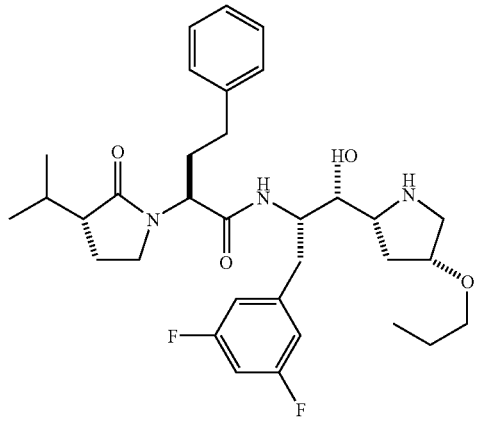

Step 5 (A): (S)-((1R,2S)-1-((2R,4R)-1-(4-methoxybenzyl)-4-(allyloxy)pyrrolidin-2-yl)-3-(3,5-difluorophenyl)-1-hydroxypropan-2-yl) 2-((R)-3-isopropyl-2-oxopyrrolidin-1-yl)-4-phenylbutanoate. To a solution of the compound of Preparation D (48.2 mg, 167 μmol) and the compound of Preparation C (60.0 mg, 139 μmol) in DMF (1.55 mL) was added HATU (78.5 mg, 206 μmol) and N-Methyl morpholine (63.9 μL, 581 μmol). The reaction was stirred at rt until LC showed conversion to product (<1 h). The crude reaction mixture was injected onto a reverse-phase HPLC column (XTERRA S5 19×100 mm, gradient from 10% MeOH/H$_2$O to 90% MeOH/H$_2$O, containing 0.1% TFA) to afford, after solvent removal, pure product. $^1$H NMR (400 MHz, CDCl$_3$) δ ppm 0.76 (d, J=6.85 Hz, 3 H) 0.98 (d, J=6.85 Hz, 3 H) 1.44-1.57 (m, 1 H) 1.87-2.16 (m, 4 H) 2.29-2.54 (m, 5 H) 2.64

(dd, J=115.16, 9.54 Hz, 1 H) 2.74-2.84 (m, 1 H) 3.03 (dd, J=11.74, 5.14 Hz, 1 H) 3.13 (q, J=8.31 Hz, 1 H) 3.25 (dd, J=15.16, 2.93 Hz, 1 H) 3.46 (t, J=8.56 Hz, 1 H) 3.53-3.64 (m, 2 H) 3.77 (s, 3 H) 3.88-4.15 (m, 5 H) 4.29 (d, J=13.45 Hz, 1 H) 4.37 (dd, J=9.78, 5.14 Hz, 1 H) 5.14-5.30 (m, 2 H) 5.77-5.90 (m, 2 H) 6.59-6.69 (m, 3 H) 6.86 (d, J=8.56 Hz, 2 H) 7.11-7.33 (m, 7 H). HPLC retention time: 1.80 min (method C). MS (ESI) (M+H)$^+$ 704.

Step 5 (B): (S)-((1R,2S)-3-(3,5-difluorophenyl)-1-hydroxy-1-((2R,4R)-4-propoxypyrrolidin-2-yl)propan-2-yl) 2-((R)-3-isopropyl-2-oxopyrrolidin-1-yl)-4-phenylbutanoate. To a solution of the compound of step 5 (A) (40 mg) in 2:1 MeOH/EtOH (4.5 mL) was added 10% Pd/C. The flask was capped with a H$_2$ balloon, and after 3 pump/flush cycles, the reaction was allowed to stir under H$_2$ over two days. The reaction was filtered through a 0.45 μm filter, and solvents removed in vacuo. Silica gel chromatography (0% to 25% MeOH/CHCl$_3$) afforded pure product of the title compound. $^1$H NMR (500 MHz, CD$_3$OD) o ppm 0.75 (d, J=7.02 Hz, 3 H) 0.91 (t, J=7.32 Hz, 3 H) 0.96 (d, J=7.02 Hz, 3 H) 1.50-1.68 (m, 3 H) 1.74-1.83 (m, 1 H) 1.84-2.12 (m, 5 H) 2.29-2.37 (m, 1 H) 2.49 (t, J=7.78 Hz, 2 H) 2.65-2.78 (m, 2 H) 3.05-3.26 (m, 5 H) 3.32-3.41 (m, 2 H) 3.65 (dd, J=7.63, 4.27 Hz, 1 H) 3.98-4.04 (m, 1 H) 4.09-4.16 (m, 1 H) 4.44 (dd, J=8.85, 6.41 Hz, 1 H) 6.68-6.75 (m, 1 H) 6.84 (d, J=6.41 Hz, 2 H) 7.11-7.19 (m, 3 H) 7.25 (t, J=7.48 Hz, 2 H). HPLC retention time: 1.80 min (method C). MS (ESI) (M+H)$^+$ 586.

EXAMPLE 6

(S)-((1R,2S)-3-(3,5-difluorophenyl)-1-hydroxy-1-((2R,4R)-4-propoxypyrrolidin-2-yl)propan-2-yl) 2-((S)-3-isobutyl-2-oxopyrrolidin-1-yl)-4-phenylbutanoate

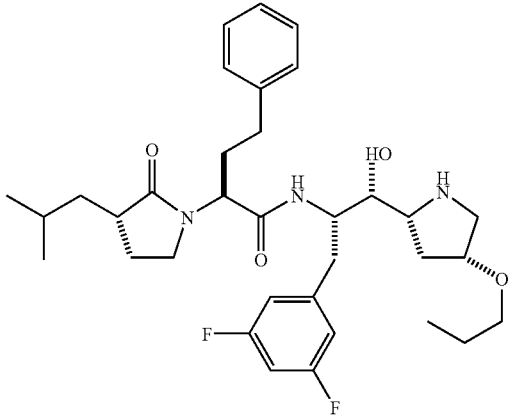

Step 6 (A): (S)-((1R,2S)-1-((2R,4R)-1-(4-methoxybenzyl)-4-(allyloxy)pyrrolidin-2-yl)-3-(3,5-difluorophenyl)-1-hydroxypropan-2-yl) 2-((S)-3-isobutyl-2-oxopyrrolidin-1-yl)-4-phenylbutanoate. To a solution of the compound of Preparation E (50.5 mg, 167 μmol) and the compound of Preparation C (60.0 mg, 139 μmol) in DMF (1.55 mL) was added HATU (78.5 mg, 206 μmol) and N-Methyl morpholine (63.9 μL, 581 μmol). The reaction was stirred at rt until LC showed conversion to product (<1 h). The crude reaction mixture was injected onto a reverse-phase HPLC column (XTERRA S5 19×100 mm, gradient from 10% MeOH/H$_2$O to 90% MeOH/H$_2$O, containing 0.1% TFA) to afford, after solvent removal, pure product. $^1$H NMR (400 MHz, CDCl$_3$) δ ppm 0.87 (d, J=6.11 Hz, 3 H) 0.92 (d, J=6.11 Hz, 3 H) 0.96-1.05 (m, 1 H) 1.20-1.33 (m, 1 H) 1.54-1.70 (m, 2 H) 1.88-2.00 (m, 1 H) 2.02-2.15 (m, 2 H) 2.31-2.54 (m, 5 H) 2.62 (dd, J=15.16, 10.03 Hz, 1 H) 2.79 (t, J=8.68 Hz, 1 H) 3.01-3.15 (m, 2 H) 3.29 (dd, J=15.04, 2.81 Hz, 1 H) 3.43 (t, J=8.56 Hz, 1 H) 3.57-3.65 (m, 2 H) 3.77 (s, 3 H) 3.93 (dd, J=12.72, 5.62 Hz, 1 H) 3.97-4.07 (m, 3 H) 4.08-4.14 (m, 1 H) 4.32 (d, J=13.45 Hz, 1 H) 4.40 (dd, J=9.54, 5.38 Hz, 1 H) 5.17 (d, J=11.00 Hz, 1 H) 5.25 (dd, J=17.24, 1.34 Hz, 1 H) 5.76-5.89 (m, 1 H) 6.01 (d, J=9.54 Hz, 2 H) 6.58-6.66 (m, 3 H) 6.87 (d, J=8.56 Hz, 2 H) 7.10-7.31 (m, 7 H). HPLC retention time: 1.93 min (method C). MS (ESI) (M+H)$^+$ 718.

Step 6 (B): (S)-((1R,2S)-3-(3,5-difluorophenyl)-1-hydroxy-1-((2R,4R)-4-propoxypyrrolidin-2-yl)propan-2-yl) 2-((S)-3-isobutyl-2-oxopyrrolidin-1-yl)-4-phenylbutanoate. To a solution of the compound of step 6 (A) (25 mg) in 2:1 MeOH/EtOH (4.5 mL) was added 10% Pd/C. The flask was capped with a H$_2$ balloon, and after 3 pump/flush cycles, the reaction was allowed to stir under H$_2$ over two days. The reaction was filtered through a 0.45 μm filter, and solvents removed in vacuo. Silica gel chromatography (0% to 25% MeOH/CHCl$_3$) afforded the pure title compound of Example 6. $^1$H NMR (500 MHz, CD$_3$OD) δ ppm 0.87-0.98 (m, 9 H) 1.09-1.19 (m, 1 H) 1.34-1.44 (m, 1 H) 1.51-1.70 (m, 4 H) 1.75-1.83 (m, 1 H) 1.86-2.12 (m, 4 H) 2.32-2.41 (m, 1 H) 2.49 (t, J=7.63 Hz, 2 H) 2.67 (dd, J=14.34, 11.29 Hz, 1 H) 2.76 (dd, J=12.21, 5.19 Hz, 1 H) 3.04-3.13 (m, 3 H) 3.13-3.26 (m, 2 H) 3.33-3.42 (m, 2 H) 3.65 (dd, J=7.78, 4.43 Hz, 1 H) 3.99-4.05 (m, 1 H) 4.10-4.17 (m, 1 H) 4.43 (dd, J=8.70, 6.56 Hz, 1 H) 6.68-6.75 (m, 1 H) 6.83 (d, J=6.41 Hz, 2 H) 7.12-7.18 (m, 3 H) 7.21-7.27 (m, 2 H). HPLC retention time: 2.63 min (method C). MS (ESI) (M+H)$^+$ 600.

EXAMPLE 7

(S)-((1R,2S)-3-(3,5-difluorophenyl)-1-hydroxy-1-((2R,4R)-4-propoxypyrrolidin-2-yl)propan-2-yl) 2-((S)-3-isobutyl-2-oxopyrrolidin-1-yl)propanoate

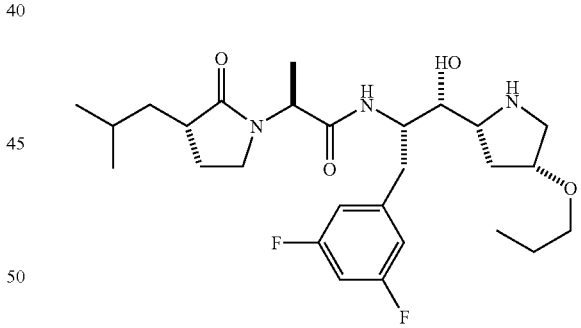

Step 7 (A): (S)-((1R,2S)-1-((2R,4R)-1-(4-methoxybenzyl)-4-(allyloxy)pyrrolidin-2-yl)-3-(3,5-difluorophenyl)-1-hydroxypropan-2-yl) 2-((S)-3-isobutyl-2-oxopyrrolidin-1-yl)propanoate. To a solution of the compound of Preparation F (35.5 mg, 167 μmol) and the compound of Preparation C (60.0 mg, 139 μmol) in DMF (1.55 mL) was added HATU (78.5 mg, 206 μmol) and N-Methyl morpholine (63.9 μL, 581 μmol). The reaction was stirred at rt until LC showed conversion to product (<1 h). The crude reaction mixture was injected onto a reverse-phase HPLC column (XTERRA S5 19×100 mm, gradient from 10% MeOH/H$_2$O to 90% MeOH/H$_2$O, containing 0.1% TFA) to afford, after solvent removal, pure product. $^1$H NMR (400 MHz, CDCl$_3$) δ ppm 0.84 (d, J=5.87 Hz, 3 H) 0.89 (d, J=6.11 Hz, 3 H) 0.98 (m, 1 H) 1.21

(d, J=7.34 Hz, 3 H 1.24-1.37 (m, 1 H) 1.52-1.66 (m, 2 H) 2.06-2.19 (m, 1 H) 2.31-2.52 (m, 3 H) 2.64 (dd, J=15.16, 10.52 Hz, 1 H) 2.82 (t, J=8.93 Hz, 1 H) 3.05 (dd, J=1.62, 5.01 Hz, 1 H) 3.12-3.21 (m, 1 H) 3.36 (dd, J=15.16, 2.69 Hz, 1 H) 3.47-3.62 (m, 2 H) 3.74-3.85 (m, 4 H) 3.88-4.06 (m, 3 H) 4.08-4.14 (m, 1 H) 4.17 (d, J=13.45 Hz, 1 H) 4.28 (d, J=13.45 Hz, 1 H) 4.44 (q, J=7.09 Hz, 1 H) 5.13-5.29 (m, 2 H) 5.74-5.88 (m, 1 H) 6.26 (d, J=9.54 Hz, 1 H) 6.58-6.67 (m, 3 H) 6.94 (d, J=8.56 Hz, 2 H) 7.30 (d, J=8.56 Hz, 2 H). HPLC retention time: 1.65 min (method C). MS (ESI) (M+H)$^+$ 628.

Step 7 (B): (S)-((1R,2S)-3-(3,5-difluorophenyl)-1-hydroxy-1-((2R,4R)-4-propoxypyrrolidin-2-yl)propan-2-yl) 2-((S)-3-isobutyl-2-oxopyrrolidin-1-yl)propanoate. To a solution of the compound of step 7 (A) (40 mg) in 2:1 MeOH/EtOH (6 mL) was added 10% Pd/C. The flask was capped with a H$_2$ balloon, and after 3 pump/flush cycles, the reaction was allowed to stir under H$_2$ overnight. The reaction was filtered through a 0.45 μm filter, and solvents removed in vacuo. Silica gel chromatography (0% to 25% MeOH/CHCl$_3$) afforded the title compound of Example 7 as a pure product. $^1$H NMR (500 MHz, CD$_3$OD) δ ppm 0.88-0.98 (m, 9 H) 1.13-1.24 (m, 4 H) 1.43-1.53 (m, 1 H) 1.55-1.72 (m, 4 H) 1.90-1.98 (m, 1 H) 2.10-2.19 (m, 1 H) 2.23-2.31 (m, 1 H) 2.35-2.46 (m, 1 H) 2.73 (dd, J=14.34, 11.29 Hz, 1 H) 3.00-3.07 (m, 1 H) 3.11 (dd, J=12.21, 5.49 Hz, 1 H) 3.20-3.29 (m, 3 H) 3.36-3.49 (m, 3 H) 3.81 (dd, J=8.55, 3.66 Hz, 1 H) 3.99-4.07 (m, 1 H) 4.13-4.19 (m, 1 H) 4.42 (q, J=7.02 Hz, 1 H) 6.72-6.78 (m, 1 H) 6.85 (d, J=6.4 Hz, 2 H). HPLC retention time: 2.28 min (method D). MS (ESI) (M+H)$^+$ 510.

EXAMPLE 8

(S)-2-((S)-3-acetamido-3-((R)-sec-butyl)-2-oxopyrrolidin-1-yl)-N-((1R,2S)-3-(3,5-difluorophenyl)-1-hydroxy-1-((R)-piperidin-2-yl)propan-2-yl)-4-phenylbutanamide

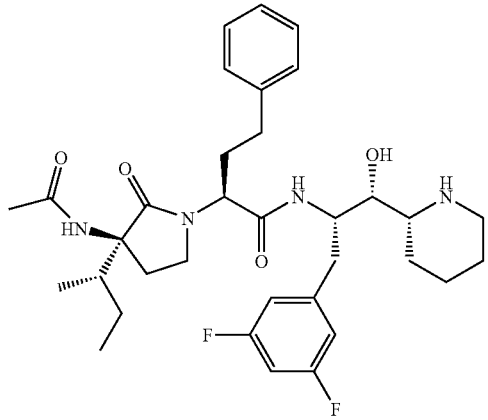

Step 8 (A): Preparation of (S)-2-((S)-3-acetamido-3-((R)-sec-butyl)-2-oxopyrrolidin-1-yl)-N-((1S,2S)-1-((R)-1-benzhydrylpiperidin-2-yl)-3-(3,5-difluorophenyl)-1-hydroxypropan-2-yl)-4-phenylbutanamide. To a solution of (S)-2-((S)-3-acetamido-3-((R)-sec-butyl)-2-oxopyrrolidin-1-yl)-4-phenylbutanoic acid (Preparation A, 45 mg, 0.126 mmol) in dichloromethane (3 mL) was added Hunig's base (45 mg, 0.38 mmol) to make a clear solution and HATU (62 mg, 0.164 mmol) was then added. After stirring for 20 min, the reaction mixture was added (1S,2S)-2-amino-1-((R)-1-benzhydrylpiperidin-2-yl)-3-(3,5-difluorophenyl)propan-1-ol (Preparation 1,55 mg, 0.126 mmol) and the reaction mixture was stirred at rt for 6 h. Solvent was removed and the crude mixture was purified by silica gel Flash Chromatography to give 75 mg of the title compound:
$^1$H NMR (CDCl$_3$, 500 MHz) δ 0.96 (3H, d, J=5 Hz), 0.98 (3H, m), 1.09-1.19 (2H, m), 1.57-1.67 (3H, m), 1.73-1.87 (5H, m), 1.99 (3H, s), 2.09-2.27 (3H, m), 2.41-2.50 (2H, m), 2.53-2.66 (4H, m), 2.76 (1H, m), 2.98 (1H, t, J=10 Hz), 3.14 (1H, m), 3.46-3.52 (2H, m), 4.42 (1H, d, J=10 Hz), 4.75 (1H, s), 4.94 (1H, m), 5.29 (1H, s), 6.07 (1H, s), 6.55 (1H, m), 6.90 (2H, d, J=5 Hz), 7.06-7.12 (5H, m), 7.16 (2H, m), 7.23-7.30 (3H, m), 7.34 (2H, d, J=5 Hz), 7.49 (2H, d, J=10 Hz), 7.60 (1H, d, J=5 Hz). MS (ESI) (M+H)$^+$ 779.42.

Step 8 (B): (S)-2-((S)-3-acetamido-3-((R)-sec-butyl)-2-oxopyrrolidin-1-yl)-N-((1R,2S)-3-(3,5-difluorophenyl)-1-hydroxy-1-((R)-piperidin-2-yl)propan-2-yl)-4-phenylbutanamide. To a solution of (S)-2-((S)-3-acetamido-3-((R)-sec-butyl)-2-oxopyrrolidin-1-yl)-N-((1S,2S)-1-((R)-1-benzhydrylpiperidin-2-yl)-3-(3,5-difluorophenyl)-1-hydroxypropan-2-yl)-4-phenylbutanamide (Step 8 (A), 75 mg) in MeOH (5 mL) was added a catalytic amount of Pd on activated charcoal (10 wt %, 20 mg). The reaction mixture was put on hydrogenator at 50 psi for 6 h. The mixture was then filtered and concentrated in vacuo and purified by silica gel Flash chromatography to give 29 mg of the title compound: $^1$H NMR (CD$_3$OD, 500 MHz) δ 0.88 (3H, d, J=10 Hz), 1.02 (3H, m), 1.09-1.16 (1H, m), 1.43-1.51 (1H, m), 1.63-1.76 (4H, m), 1.83 (1H, d, J=10 Hz), 1.92 (2H, t, J=15 Hz), 1.99 (3H, s), 2.08-2.16 (1H, m), 2.19 (2H, m), 2.30-2.37 (1H, m), 2.54-2.60 (1H, m), 2.70-2.75 (1H, m), 2.78-2.83 (1H, m), 2.88 (1H, m), 3.12 (1H, d, J=10 Hz), 3.24 (1H, d, J=15 Hz), 3.29-3.37 (2H, m), 3.42-3.47 (1H, m), 3.95-4.00 (3H, m), 6.73 (1H, m), 6.86-6.89 (2H, m), 7.17-7.20 (3H, m), 7.26-7.29 (2H, m). MS (ESI) (M+H)$^+$ 613.30.

EXAMPLE 9

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-phenoxypyrrolidin-2-yl)propan-2-yl)-4-phenylbutanamide

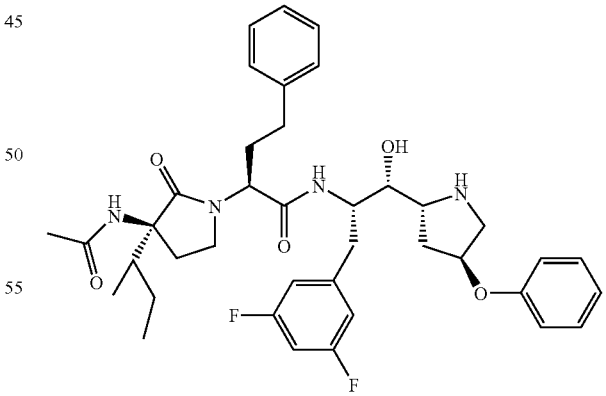

Step 9 (A): (4S,5S)-4-(3,5-difluorobenzyl)-5-((2R,4S)-1-benzhydryl-4-phenoxypyrrolidin-2-yl)oxazolidin-2-one. To a solution of triphenylphosphine (58 mg, 0.22 mmol) in THF (2.5 mL) at rt was added DEAD (0.035 mL, 0.22 mmol). After 1 min, a solution of (4S,5S)-4-(3,5-difluorobenzyl)-5-((2R,4R)-1-benzhydryl-4-hydroxypyrrolidin-2-yl)oxazolidin-2-one (Preparation J, 85 mg, 0.183 mmol) in THF (2.5 mL) was added. After 2 min, phenol (17.2 mg, 0.183 mmol) was added and the mixture was stirred at rt for 3.5 h. pH 7 buffer was added and the mixture was extracted with ethyl acetate. The combined organic phases were washed with sat. aqueous NaCl, dried (MgSO$_4$), and concentrated in vacuo. Flash chromatography (silica gel, 0-100% ethyl acetate/hexane) gave 57.6 mg (58% yield) of the title compound: $^1$H NMR (CDCl$_3$, 300 MHz) δ 2.22 (1H, m), 2.40-2.45 (3H, m), 2.88 (1H, m), 3.27 (1H, dd, J=6, 12 Hz), 3.55-3.62 (2H, m), 4.68 (1H, d, J=9 Hz), 4.96 (2H, s), 5.35 (1H, s), 6.50 (2H, m), 6.64-6.75 (2H, m), 6.85-6.95 (3H, m), 7.16-7.29 (7H, m), 7.41 (4H, d, J=6 Hz). HPLC retention time: 2.10 min (method B). MS (ESI) (M+H)$^+$ 541.11.

Step 9 (B): (1S,2S)-2-amino-1-((2R,4S)-1-benzhydryl-4-phenoxypyrrolidin-2-yl)-3-(3,5-difluorophenyl)propan-1-ol. To a solution of (4S,5S)-4-(3,5-difluorobenzyl)-5-((2R,4S)-1-benzhydryl-4-phenoxypyrrolidin-2-yl)oxazolidin-2-one (Step 9 (A), 57 mg, 0.11 mmol) in EtOH (5 mL) was added a solution of LiOH (53 mg, 2.2 mmol) in H$_2$O (1.5 mL). This reaction mixture was stirred at reflux for 4 h. After cooling down to rt, the mixture was concentrated to remove EtOH and H$_2$O was added followed by 1N HCl solution and pH 7 buffer. The mixture was extracted with ethyl acetate and the organic phase was washed with sat. aqueous NaCl, dried (MgSO$_4$), and concentrated in vacuo. Flash chromatography (silica gel, 0-10% MeOH/chloroform) gave 41.1 mg (73% yield) of the title compound: $^1$H NMR (CDCl$_3$, 300 MHz) δ 2.05-2.12 (1H, m), 2.21-2.30 (1H, m), 2.39 (1H, m), 2.62-2.72 (2H, m), 2.90-2.99 (2H, m), 3.39 (1H, dd, J=3, 12 Hz), 3.69 (1H, m), 4.80 (1H, m), 5.07 (1H, s), 6.65-6.68 (3H, m), 6.82 (2H, m), 6.93 (1H, m), 7.14 (1H, m), 7.20-7.31 (7H, m), 7.35-7.38 (4H, m). HPLC retention time: 1.65 min (method C). MS (ESI) (M+H)$^+$ 515.35.

Step 9 (C): (S)-2-((S)-3-acetamido-3-((R)-sec-butyl)-2-oxopyrrolidin-1-yl)-N-((1S,2S)-1-((2R,4S)-1-benzhydryl-4-phenoxypyrrolidin-2-yl)-3-(3,5-difluorophenyl)-1-hydroxypropan-2-yl)-4-phenylbutanamide. To a solution of (S)-2-((S)-3-acetamido-3-((R)-sec-butyl)-2-oxopyrrolidin-1-yl)-4-phenylbutanoic acid (Preparation A, 29 mg, 0.080 mmol) in DMF (2 mL) was added HATU (36.5 mg, 0.096 mmol). A solution of (1S,2S)-2-amino-1-((2R,4S)-1-benzhydryl-4-phenoxypyrrolidin-2-yl)-3-(3,5-difluorophenyl)propan-1-ol (Step 9 (B), 41.1 mg, 0.080 mmol) in DMF (2 mL) was then added, followed by N-methylmorpholine (37 μl, 0.336 mmol). The reaction mixture was stirred at rt for 3 h. pH 4 buffer was then added to quench. The mixture was extracted with ethyl acetate. The organic phase was washed with sat. aqueous NaCl, dried (MgSO$_4$), and concentrated in vacuo. The crude mixture was purified by reverse phase Prep HPLC to give the title compound (34 mg): $^1$H NMR (CDCl$_3$, 300 MHz) δ 0.82 (3H, d, J=6 Hz), 0.98 (3H, m), 1.07-1.15 (1H, m), 1.51-1.61 (1H, m), 1.68-1.74 (1H, m), 1.85-2.08 (5H, m), 2.17-2.30 (1H, m), 2.41-2.57 (2H, m), 2.63-2.76 (2H, m), 2.80-2.95 (3H, m), 3.09 (1H, dd, J=3, 15 Hz), 3.47-3.54 (3H, m), 3.67-4.05 (6H, m), 5.08 (1H, m), 5.39 (1H, s), 5.99 (1H, s), 6.56-6.69 (4H, m), 6.86 (2H, d, J=9 Hz), 7.03 (1H, m), 7.14-7.34 (12H, m), 7.68 (2H, m), 7.63-7.66 (2H, m). HPLC retention time: 1.99 min (method C). MS (ESI) (M+H)$^+$ 857.45.

Step 9 (D): (S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-phenoxypyrrolidin-2-yl)propan-2-yl)-4-phenylbutanamide. To a solution of (S)-2-((S)-3-acetamido-3-((R)-sec-butyl)-2-oxopyrrolidin-1-yl)-N-((1S,2S)-1-((2R,4S)-1-benzhydryl-4-phenoxypyrrolidin-2-yl)-3-(3,5-difluorophenyl) 1-hydroxypropan-2-yl)-4-phenylbutanamide (Step 9 (C), 34 mg) in MeOH (4 mL) was added a catalytic amount of Pd/C (10 wt %). The reaction mixture was stirred under 1 atm. of H$_2$ for 5 h. The mixture was then filtered and concentrated in vacuo. Flash chromatography (silica gel, 0-7.5% methanol/chloroform) gave 18.3 mg (67% yield) the title compound of Example 9 as an opaque glass:

$^1$H NMR (CD$_3$OD, 500 MHz) δ 0.81 (3H, d, J=10 Hz), 1.00 (3H, m), 1.06-1.13 (1H, m), 1.67-1.71 (2H, m), 1.92-1.99 (4H, m), 2.11-2.36 (5H, m), 2.48-2.54 (1H, m), 2.64-2.71 (2H, m), 3.21 (1H, m), 3.27-3.35 (2H, m), 3.50 (1H, d, J=15 Hz), 3.60 (1H, dd, J=10, 15 Hz), 3.92 (1H, dd, J=10, 15 Hz), 3.99 (2H, m), 4.09 (1H, m), 5.17 (1H, m), 6.71 (1H, m), 6.82-6.87 (4H, m), 6.96 (1H, m), 7.17-7.29 (7H, m). HPLC retention time: 2.14 min (method B). MS (ESI) (M+H)$^+$ 691.35. HRMS calcd for C$_{39}$H$_{49}$N$_4$O$_5$F$_2$ 691.3671 (MH$^+$), found 691.3677.

EXAMPLE 10

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-(pyridin-2-yloxy)pyrrolidin-2-yl)propan-2-yl)-4-phenylbutanamide

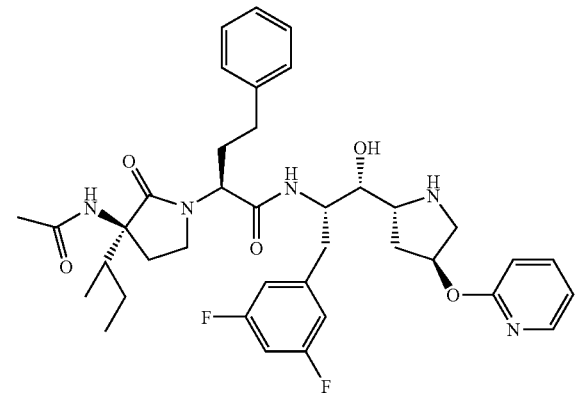

Step 10 (A): (4S,5S)-4-(3,5-difluorobenzyl)-5-((2R,4S)-1-benzhydryl-4-(pyridin-2-yloxy)pyrrolidin-2-yl)oxazolidin-2-one. To a solution of triphenylphosphine (58 mg, 0.22 mmol) in THF (2.5 mL) at rt was added DEAD (0.035 mL, 0.22 mmol). After 1 min, a solution of (4S,5S)-4-(3,5-difluorobenzyl)-5-((2R,4R)-1-benzhydryl-4-hydroxypyrrolidin-2-yl)oxazolidin-2-one (Preparation J, 85 mg, 0.183 mmol) in THF (2.5 mL) was added. After 2 min, 2-hydroxypyridine (17.4 mg, 0.183 mmol) was added and the mixture was stirred at rt for 3.5 h. pH 7 buffer was added and the mixture was extracted with ethyl acetate. The combined organic phases were washed with sat. aqueous NaCl, dried (MgSO$_4$), and concentrated in vacuo. Flash chromatography (silica gel, 0-100% ethyl acetate/hexane) gave 50.7 mg (52% yield) of the title compound: $^1$H NMR (CDCl$_3$, 300 MHz) δ 2.22 (1H, m), 2.38-2.55 (3H, m), 2.87 (1H, d, J=12 Hz), 3.32 (1H, dd, J=6, 12 Hz), 3.56-3.63 (2H, m), 4.70 (1H, d, J=9 Hz), 4.96 (1H, s), 5.42 (1H, s), 5.51 (1H, s), 6.47-6.53 (2H, m), 6.62-6.73 (3H, m), 6.81 (1H, t, J=6 Hz), 7.13-7.28 (5H, m), 7.37-7.42 (4H, m), 7.54 (1H, m), 8.08 (1H, m). HPLC retention time: 1.73 min (method C). MS (ESI) (M+H)$^+$ 542.31.

Step 10 (B): (1S,2S)-2-amino-1-((2R,4S)-1-benzhydryl-4-(pyridin-2-yloxy)pyrrolidin-2-yl)-3-(3,5-difluorophenyl)propan-1-ol. To a solution of (4S,5S)-4-(3,5-difluorobenzyl)-5-((2R,4S)-1-benzhydryl-4-(pyridin-2-yloxy)pyrrolidin-2- yl)oxazolidin-2-one (Step 10 (A), 50 mg, 0.092 mmol) in EtOH (5 mL) was added a solution of LiOH (44 mg, 1.84 mmol) in H$_2$O (1.5 mL). This reaction mixture was stirred at reflux for 4 h. After cooling down to rt, the mixture was concentrated to remove EtOH and H$_2$O was added followed by 1N HCl solution and pH 7 buffer. The mixture was extracted with ethyl acetate and the organic phase was washed with sat. aqueous NaCl, dried (MgSO$_4$), and concentrated in vacuo. Flash chromatography (silica gel, 0-10% MeOH/chloroform) gave 29.0 mg (61% yield) of the title compound: $^1$H NMR (CDCl$_3$, 300 MHz) δ 2.03-2.11 (2H, m), 2.23-2.42 (2H, m), 2.69 (2H, s), 2.92-2.97 (2H, m), 3.48 (1H, dd, J=3, 12 Hz), 3.73 (1H, m), 5.07 (1H, s), 5.44 (1H, s), 6.61-6.68 (4H, m), 6.82 (1H, m), 7.12-7.29 (6H, m), 7.32-7.44 (4H, m), 7.54 (1H, m), 8.06 (1H, dd, J=3, 6 Hz). HPLC retention time: 1.54 min (method C). MS (ESI) (M+H)$^+$ 516.35.

Step 10 (C): (S)-2-((S)-3-acetamido-3-((R)-sec-butyl)-2-oxopyrrolidin-1-yl)-N-((1S,2S)-1-((2R,4S)-1-benzhydryl-4-(pyridin-2-yloxy)pyrrolidin-2-yl)-3-(3,5-difluorophenyl)-1-hydroxypropan-2-yl)-4-phenylbutanamide. To a solution of (S)-2-((S)-3-acetamido-3-((R)-sec-butyl)-2-oxopyrrolidin-1-yl)-4-phenylbutanoic acid (Preparation A, 20.2 mg, 0.056 mmol) in DMF (2 mL) was added HATU (25.6 mg, 0.067 mmol). A solution of (1S,2S)-2-amino-1-((2R,4S)-1-benzhydryl-4-(pyridin-2-yloxy)pyrrolidin-2-yl)-3-(3,5-difluorophenyl)propan-1-ol (Step 10 (B), 29.0 mg, 0.056 mmol) in DMF (2 mL) was then added, followed by N-methylmorpholine (22 μl, 0.196 mmol). The reaction mixture was stirred at rt for 3 h. pH 4 buffer was then added to quench. The mixture was extracted with ethyl acetate. The organic phase was washed with sat. aqueous NaCl, dried (MgSO$_4$), and concentrated in vacuo. The crude mixture was purified by reverse phase Prep HPLC to give the title compound (19 mg):
$^1$H NMR (CDCl$_3$, 300 MHz) δ 0.82 (3H, d, J=6 Hz), 0.98 (3H, m), 1.04-1.15 (1H, m), 1.53-1.62 (1H, m), 1.68-1.73 (1H, m), 1.85-2.11 (6H, m), 2.25 (1H, m), 2.41-2.78 (6H, m), 2.85-2.95 (3H, m), 3.10 (1H, dd, J=3, 15 Hz), 3.52-3.56 (2H, m), 3.73-3.79 (1H, m), 3.90-4.03 (3H, m), 5.34 (1H, s), 5.67 (1H, m), 5.95 (1H, s), 6.56-6.67 (4H, m), 6.80 (1H, d, J=9 Hz), 6.94 (1H, m), 7.10-7.36 (9H, m), 7.59-7.70 (6H, m), 8.08 (1H, dd, J=3, 6 Hz). HPLC retention time: 1.94 min (method C). MS (ESI) (M+H)$^+$ 858.45.

Step 10 (D): (S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-(pyridin-2-yloxy)pyrrolidin-2-yl)propan-2-yl)-4-phenylbutanamide. To a solution of (S)-2-((S)-3-acetamido-3-((R)-sec-butyl)-2-oxopyrrolidin-1-yl)-N-((1S,2S)-1-((2R,4S)-1-benzhydryl-4-(pyridin-2-yloxy)pyrrolidin-2-yl)-3-(3,5-difluorophenyl)-1-hydroxypropan-2-yl)-4-phenylbutanamide (Step 10 (C), 19 mg) in MeOH (4 mL) was added a catalytic amount of Pd/C (10 wt %). The reaction mixture was stirred under 1 atm. of H$_2$ for 5 h. The mixture was then filtered and concentrated in vacuo. Flash chromatography (silica gel, 0-7.5% methanol/chloroform) gave 5.5 mg (36% yield) the title compound of Example 10 as an opaque glass: $^1$H NMR (CD$_3$OD, 500 MHz) δ 0.81 (3H, d, J=10 Hz), 1.00 (3H, m), 1.05-1.13 (1H, m), 1.68-1.71 (2H, m), 1.97-2.04 (4H, m), 2.14-2.28 (3H, m), 2.36 (2H, m), 2.50-2.56 (1H, m), 2.68-2.73 (2H, m), 3.24-3.29 (2H, m), 3.37-3.41 (1H, m), 3.52 (1H, d, J=10 Hz), 3.68 (1H, dd, J=5, 15 Hz), 3.98-4.05 (3H, m), 4.09-4.11 (1H, m), 5.67 (1H, m), 6.52 (1H, d, J=5 Hz), 6.73 (1H, m), 6.87-6.89 (2H, m), 6.96 (1H, m), 7.18-7.22 (3H, m), 7.27-7.30 (2H, m), 7.58 (1H, m), 8.12 (1H, m). HPLC retention time: 2.10 min (method B). MS (ESI) (M+H)$^+$ 692.34.

HRMS calcd for C$_{38}$H$_{48}$N$_5$O$_5$F$_2$ 692.3624 (MH$^+$), found 692.3658.

EXAMPLE 11

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-phenoxypyrrolidin-2-yl)propan-2-yl)-4-phenylbutanamide

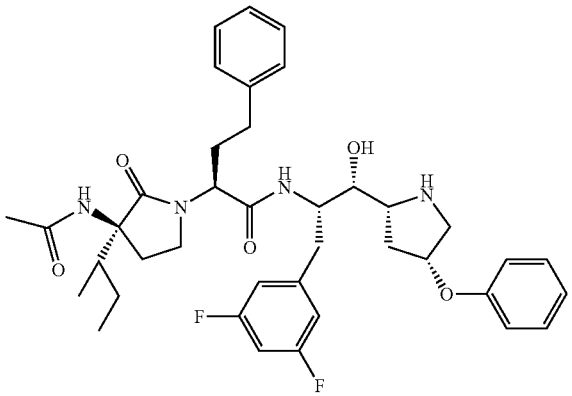

Step 11 (A): (4S,5S)-4-(3,5-difluorobenzyl)-5-((2R,4R)-1-benzhydryl-4-phenoxypyrrolidin-2-yl)oxazolidin-2-one.
To a solution of triphenylphosphine (54 mg, 0.206 mmol) in THF (2.5 mL) at rt was added DEAD (0.0324 mL, 0.206 mmol). After 1 min, a solution of (4S,5S)-4-(3,5-difluorobenzyl)-5-((2R,4S)-1-benzhydryl-4-hydroxypyrrolidin-2-yl)oxazolidin-2-one (Preparation K, 80 mg, 0.172 mmol) in THF (2.5 mL) was added. After 2 min, phenol (16.2 mg, 0.172 mmol) was added and the mixture was stirred at rt for 3.5 h. pH 7 buffer was added and the mixture was extracted with ethyl acetate. The combined organic phases were washed with sat. aqueous NaCl, dried (MgSO$_4$), and concentrated in vacuo. Flash chromatography (silica gel, 0-100% ethyl acetate/hexane) gave 34.7 mg of the title compound as an opaque oil: $^1$H NMR (CDCl$_3$, 300 MHz) δ 2.20-2.25 (2H, m), 2.43 (1H, t, J=12 Hz), 2.25 (1H, m), 3.15-3.29 (2H, m), 3.57 (1H, dd, J=6, 12 Hz), 3.85 (1H, m), 4.60 (1H, m), 4.83 (1H, m), 4.92 (1H, s), 5.04 (1H, s), 6.51 (2H, m), 6.68 (1H, m), 6.76 (2H, d, J=6 Hz), 6.91 (1H, m), 7.20-7.39 (12H, m). HPLC retention time: 1.75 min (method A). MS (ESI) (M+H)$^+$ 541.27.

Step 11 (B): (1S,2S)-2-amino-1-((2R,4R)-1-benzhydryl-4-phenoxypyrrolidin-2-yl)-3-(3,5-difluorophenyl)propan-1-ol. To a solution of (4S,5S)-4-(3,5-difluorobenzyl)-5-((2R,4R)-1-benzhydryl-4-phenoxypyrrolidin-2-yl)oxazolidin-2-one (Step 11 (A), (34.7 mg, 0.064 mmol) in EtOH (3 mL) was added a solution of LiOH (31 mg, 1.28 mmol) in H$_2$O (0.75 mL). This reaction mixture was stirred at reflux for 4 h. After cooling down to rt, the mixture was concentrated to remove EtOH and H$_2$O was added followed by 1N HCl solution and pH 7 buffer. The mixture was extracted with ethyl acetate and the organic phase was washed with sat. aqueous NaCl, dried (MgSO$_4$), and concentrated in vacuo. Flash chromatography (silica gel, 0-10% MeOH/chloroform) gave 29 mg of the title compound: $^1$H NMR (CDCl$_3$, 300 MHz) δ 2.16-2.29 (2H, m), 2.49-2.59 (2H, m), 2.78-3.42 (8H, m), 4.68 (1H, s), 4.95 (1H, s), 6.63-6.74 (3H, m), 6.88-6.93 (2H, m), 6.95-6.98 (1H, m), 7.09-7.36 (11H, m), 7.46-7.48 (1H, m). HPLC retention time: 1.59 min (method A). MS (ESI) (M+H)$^+$ 515.19.

Step 11 (C): (S)-2-((S)-3-acetamido-3-((R)-sec-butyl)-2-oxopyrrolidin-1-yl)-N-((1S,2S)-1-((2R,4R)-1-benzhydryl-4-phenoxypyrrolidin-2-yl)-3-(3,5-difluorophenyl)-1-hydroxypropan-2-yl)-4-phenylbutanamide. To a solution of (S)-2-((S)-3-acetamido-3-((R)-sec-butyl)-2-oxopyrrolidin-1-yl)-4-phenylbutanoic acid (Preparation A, 20.3 mg, 0.056 mmol) in DMF (1 mL) was added HATU (25.5 mg, 0.0672 mmol). A solution of (1S,2S)-2-amino-1-((2R,4R)-1-benzhydryl-4-phenoxypyrrolidin-2-yl)-3-(3,5-difluorophenyl)propan-1-ol (Step 11 (B), 29 mg, 0.056 mmol) in DMF (1 mL) was then added, followed by N-methylmorpholine (22 µl, 0.196 mmol). The reaction mixture was stirred at rt for 3 h. pH 4 buffer was then added to quench. The mixture was extracted with ethyl acetate. The organic phase was washed with sat. aqueous NaCl, dried (MgSO$_4$), and concentrated in vacuo. The crude mixture was purified by reverse phase Prep HPLC to give the title compound (27 mg, 56% yield) as a clear, slightly brown glass: $^1$H NMR (CDCl$_3$, 300 MHz) δ 0.90 (3H, d, J=6 Hz), 1.01 (3H, m), 1.09-1.19 (1H, m), 1.51-1.61 (1H, m), 1.66-1.90 (5H, m), 2.00-2.08 (2H, m), 2.15-2.30 (1H, m), 2.40-2.49 (2H, m), 2.58-2.67 (2H, m), 2.89-3.14 (3H, m), 3.38-3.53 (3H, m), 3.71-3.96 (3H, m), 4.21-4.42 (1H, m), 5.02-5.14 (2H, m), 6.07 (1H, s), 6.53-6.63 (3H, m), 6.81 (2H, d, J=6 Hz), 6.97 (1H, m), 7.12-7.39 (13H, m), 7.56 (2H, m), 7.67 (2H, d, J=6 Hz), 9.14 (3H, brd s). HPLC retention time: 1.93 min (method A). MS (ESI) (M+H)$^+$ 857.32.

Step 11 (D): (S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-phenoxypyrrolidin-2-yl)propan-2-yl)-4-phenylbutanamide. To a solution of (S)-2-((S)-3-acetamido-3-((R)-sec-butyl)-2-oxopyrrolidin-1-yl)-N-((1S,2S)-1-((2R,4R)-1-benzhydryl-4-phenoxypyrrolidin-2-yl)-3-(3,5-difluorophenyl)-1-hydroxypropan-2-yl)-4-phenylbutanamide (Step 11 (C), 27 mg) in MeOH (2 mL) was added a catalytic amount of Pd/C (10 wt %). The reaction mixture was stirred under 1 atm. of H$_2$ for 5 h. The mixture was then filtered and concentrated in vacuo. Flash chromatography (silica gel, 0-7.5% methanol/chloroform) gave 10.6 mg (49% yield) of the title compound of Example 11 as an opaque oil: $^1$H NMR (CD$_3$OD, 500 MHz) δ 0.90 (3H, d, J=5 Hz), 1.02 (3H, m), 1.10-1.17 (1H, m), 1.70-1.75 (2H, m), 1.98 (3H, s), 2.07-2.22 (4H, m), 2.40 (1H, m), 2.51-2.60 (2H, m), 2.71-2.82 (2H, m), 3.23 (1H, m), 3.32-3.37 (1H, m), 3.42-3.51 (3H, m), 3.67 (1H, m), 3.85-3.93 (2H, m), 4.10 (1H, dd, J=5, 10 Hz), 5.09 (1H, m), 6.71 (1H, m), 6.87-6.89 (2H, m), 6.93-6.94 (2H, m), 6.99 (1H, m), 7.17-7.20 (3H, m), 7.26-7.32 (4H, m). HPLC retention time: 1.78 min (method A). MS (ESI) (M+H)$^+$ 692.27. HRMS calcd for C$_{39}$H$_{49}$N$_4$O$_5$F$_2$ 691.3671 (MH$^+$), found 691.3642.

EXAMPLE 12

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-2-yloxy)pyrrolidin-2-yl)propan-2-yl)-4-phenylbutanamide

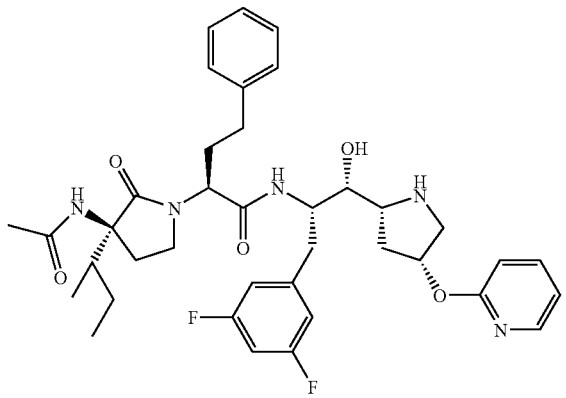

Step 12 (A): (4S,5S)-4-(3,5-difluorobenzyl)-5-((2R,4R)-1-benzhydryl-4-(pyridin-2-yloxy)pyrrolidin-2-yl)oxazolidin-2-one. To a solution of triphenylphosphine (54 mg, 0.206 mmol) in THF (2.5 mL) at rt was added DEAD (0.0324 mL, 0.206 mmol). After 1 min, a solution of (4S,5S)-4-(3,5-difluorobenzyl)-5-((2R,4S)-1-benzhydryl-4-hydroxypyrrolidin-2-yl)oxazolidin-2-one (Preparation K, 80 mg, 0.172 mmol) in THF (2.5 mL) was added. After 2 min, 2-hydroxypyridine (16.4 mg, 0.172 mmol) was added and the mixture was stirred at rt for 3.5 h. pH 7 buffer was added and the mixture was extracted with ethyl acetate. The combined organic phases were washed with sat. aqueous NaCl, dried (MgSO$_4$), and concentrated in vacuo. Flash chromatography (silica gel, 0-100% ethyl acetate/hexane) gave 39.7 mg of the title compound as an opaque oil: $^1$H NMR (CDCl$_3$, 300 MHz) δ 2.17-2.22 (1H, m), 2.32-2.42 (2H, m), 2.74 (1H, dd, J=3, 12 Hz), 3.20 (2H, m), 3.50 (1H, m), 3.78 (1H, m), 4.80 (1H, m), 4.97 (1H, s), 5.02 (1H, s), 5.38 (1H, m), 6.51 (2H, m), 6.66 (1H, m), 6.72 (1H, d, J=9 Hz), 6.81 (1H, t, J=6 Hz), 7.18-7.36 (10H, m), 7.52 (1H, m), 8.04 (1H, m). HPLC retention time: 1.52 min (method A). MS (ESI) (M+H)$^+$ 542.15.

Step 12 (B): (1S,2S)-2-amino-1-((2R,4R)-1-benzhydryl-4-(pyridin-2-yloxy)pyrrolidin-2-yl)-3-(3,5-difluorophenyl)propan-1-ol. To a solution of (4S,5S)-4-(3,5-difluorobenzyl)-5-((2R,4R)-1-benzhydryl-4-(pyridin-2-yloxy)pyrrolidin-2-yl)oxazolidin-2-one (Step 12 (A), 39.2 mg, 0.072 mmol) in EtOH (3 mL) was added a solution of LiOH (35 mg, 1.44 mmol) in H$_2$O (0.75 mL). This reaction mixture was stirred at reflux for 4 h. After cooling down to rt, the mixture was concentrated to remove EtOH and H$_2$O was added followed by 1N HCl solution and pH 7 buffer. The mixture was extracted with ethyl acetate and the organic phase was washed with sat. aqueous NaCl, dried (MgSO$_4$), and concentrated in vacuo. Flash chromatography (silica gel, 0-10% MeOH/chloroform) gave 34.5 mg (93% yield) of the title compound as a clear oil: $^1$H NMR (CDCl$_3$, 300 MHz) δ 2.12-2.31 (3H, m), 2.44 (1H, m), 2.64 (1H, dd, J=6, 12 Hz), 2.80 (1H, m), 2.99-3.09 (2H, m), 3.30-3.38 (2H, m), 4.98 (1H, s), 5.36 (1H, m), 6.60-6.73 (3H, m), 6.79-6.86 (2H, m), 7.11-7.39 (9H, m), 7.45-7.47 (1H, m), 7.58 (1H, m), 8.06 (1H, m). HPLC retention time: 1.55 min (method A). MS (ESI) (M+H)$^+$ 516.24.

Step 12 (C): (S)-2-((S)-3-acetamido-3-((R)-sec-butyl)-2-oxopyrrolidin-1-yl)-N-((1S,2S)-1-((2R,4R)-1-benzhydryl-4-(pyridin-2-yloxy)pyrrolidin-2-yl)-3-(3,5-difluorophenyl)-1-hydroxypropan-2-yl)-4-phenylbutanamide. To a solution of (S)-2-((S)-3-acetamido-3-((R)-sec-butyl)-2-oxopyrrolidin-1-yl)-4-phenylbutanoic acid (Preparation A, 21.1 mg, 0.067 mmol) in DMF (1 mL) was added HATU (30.0 mg, 0.081 mmol). A solution of (1S,2S)-2-amino-1-((2R,4R)-1-benzhydryl-4-(pyridin-2-yloxy)pyrrolidin-2-yl)-3-(3,5-difluorophenyl)propan-1-ol (Step 12 (B), 34.5 mg, 0.067 mmol) in DMF (1 mL) was then added, followed by N-methylmorpholine (26 µl, 0.235 mmol). The reaction mixture was stirred at rt for 3 h. pH 4 buffer was then added to quench. The mixture was extracted with ethyl acetate. The organic phase was washed with sat. aqueous NaCl, dried (MgSO$_4$), and concentrated in vacuo. The crude mixture was purified by reverse phase Prep HPLC to give the title compound (46.1 mg, 80% yield) as a yellow oil: $^1$H NMR (CDCl$_3$, 300 MHz) δ 0.88 (3H, d, J=6 Hz), 0.99 (3H, t, J=6 Hz), 1.10-1.17 (1H, m), 1.53-1.63 (1H, m), 1.74-1.80 (1H, m), 1.88-1.98 (3H, m), 2.08 (2H, m), 2.21-2.29 (1H, m), 2.38-2.51 (2H, m), 2.61-3.06 (5H, m), 3.47-3.61 (3H, m), 3.69-3.75 (1H, m), 3.90-3.96 (3H, m), 4.11 (1H, brd s), 5.20 (1H, s), 5.70 (1H, m), 6.15 (1H, s), 6.89-7.01 (3H, m), 7.11-7.22 (5H, m), 7.30-7.40 (5H, m), 7.60 (2H, m), 7.72 (3H, d, J=6 Hz), 8.08 (1H, m), 9.83 (3H, brd s). HPLC retention time: 1.87 min (method A). MS (ESI) (M+H)$^+$ 858.30.

Step 12 (D): (S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-2-yloxy)pyrrolidin-2-yl)

propan-2-yl)-4-phenylbutanamide. To a solution of (S)-2-((S)-3-acetamido-3-((R)-sec-butyl)-2-oxopyrrolidin-1-yl)-N-((1S,2S)-1-((2R,4R)-1-benzhydryl-4-(pyridin-2-yloxy)pyrrolidin-2-yl)-3-(3,5-difluorophenyl)-1-hydroxypropan-2-yl)-4-phenylbutanamide (Step 12 (C), 46.1 mg) in MeOH (2 mL) was added a catalytic amount of Pd/C (10 wt %). The reaction mixture was stirred under 1 atm. of H$_2$ for 5 h. The mixture was then filtered and concentrated in vacuo. Flash chromatography (silica gel, 0-7.5% methanol/chloroform) gave 19.9 mg of the title compound of Example 12 as an opaque glass: $^1$H NMR (CD$_3$OD, 500 MHz) δ 0.92 (3H, d, J=10 Hz), 1.03 (3H, m), 1.10-1.18 (1H, m), 1.71-1.76 (2H, m), 2.01 (3H, s), 2.11-2.24 (4H, m), 2.43-2.47 (1H, m), 2.56-2.66 (2H, m), 2.71-2.75 (1H, m), 2.82 (1H, m), 3.25 (1H, m), 3.34 (1H, m), 3.42-3.46 (1H, m), 3.55 (1H, d, J=15 Hz), 3.67 (1H, dd, J=5, 10 Hz), 3.81-3.87 (3H, m), 4.09 (1H, d, J=10 Hz), 5.90 (1H, s), 6.72 (1H, t, J=10 Hz), 6.84-6.89 (3H, m), 7.00 (1H, t, J=5 Hz), 7.18 (3H, d, J=10 Hz), 7.27 (2H, m), 7.71 (1H, m), 8.14 (2H, m), 8.24 (1H, d, J=10 Hz). HPLC retention time: 1.72 min (method A). MS (ESI) (M+H)$^+$ 692.28.

EXAMPLE 13

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-3-yloxy)pyrrolidin-2-yl)propan-2-yl)-4-phenylbutanamide

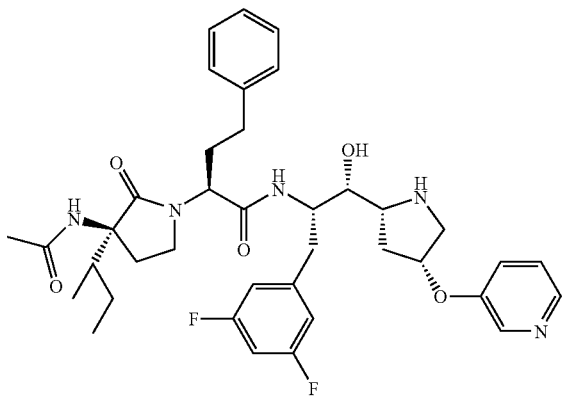

Step 13 (A): (4S,5S)-4-(3,5-difluorobenzyl)-5-((2R,4R)-1-benzhydryl-4-(pyridin-3-yloxy)pyrrolidin-2-yl)oxazolidin-2-one. To a solution of triphenylphosphine (54 mg, 0.206 mmol) in THF (2.5 mL) at rt was added DEAD (0.0324 mL, 0.206 mmol). After 1 min, a solution of (4S,5S)-4-(3,5-difluorobenzyl)-5-((2R,4S)-1-benzhydryl-4-hydroxypyrrolidin-2-yl)oxazolidin-2-one (Preparation K, 80 mg, 0.172 mmol) in THF (2.5 mL) was added. After 2 min, 3-hydroxypyridine (16.4 mg, 0.172 mmol) was added and the mixture was stirred at rt for 3.5 h. pH 7 buffer was added and the mixture was extracted with ethyl acetate. The combined organic phases were washed with sat. aqueous NaCl, dried (MgSO$_4$), and concentrated in vacuo. Flash chromatography (silica gel, 0-100% ethyl acetate/hexane) gave the title compound: HPLC retention time: 1.39 min (method A). MS (ESI) (M+H)$^+$ 542.18.

Step 13 (B): (1S,2S)-2-amino-1-((2R,4R)-1-benzhydryl-4-(pyridin-3-yloxy)pyrrolidin-2-yl)-3-(3,5-difluorophenyl)propan-1-ol. To a solution of (4S,5S)-4-(3,5-difluorobenzyl)-5-((2R,4R)-1-benzhydryl-4-(pyridin-3-yloxy)pyrrolidin-2-yl)oxazolidin-2-one (Step 13 (A), 119 mg, 0.22 mmol) in EtOH (10 mL) was added a solution of LiOH (106 mg, 4.4 mmol) in H$_2$O (3 mL). This reaction mixture was stirred at reflux for 4 h. After cooling down to rt, the mixture was concentrated to remove EtOH and H$_2$O was added followed by 1N HCl solution and pH 7 buffer. The mixture was extracted with ethyl acetate and the organic phase was washed with sat. aqueous NaCl, dried (MgSO$_4$), and concentrated in vacuo. Flash chromatography (silica gel, 0-10% MeOH/chloroform) gave 25.9 mg of the title compound as an opaque oil:
$^1$H NMR (CDCl$_3$, 300 MHz) δ 2.15-2.25 (2H, m), 2.49 (1H, dd, J=9, 15 Hz), 2.62 (1H, dd, J=3, 12 Hz), 2.85 (1H, m), 2.98 (1H, dd, J=3, 12 Hz), 3.16 (1H, m), 3.31-3.37 (2H, m), 4.70 (1H, s), 4.95 (1H, s), 6.62-6.70 (3H, m), 7.12-7.34 (12H, m), 8.20 (1H, m), 8.30 (1H, s). HPLC retention time: 1.41 min (method A). MS (ESI) (M+H)$^+$ 516.16.

Step 13 (C): (S)-2-((S)-3-acetamido-3-((R)-sec-butyl)-2-oxopyrrolidin-1-yl)-N-((1S,2S)-1-((2R,4R)-1-benzhydryl-4-(pyridin-3-yloxy)pyrrolidin-2-yl)-3-(3,5-difluorophenyl)-1-hydroxypropan-2-yl)-4-phenylbutanamide. To a solution of (S)-2-((S)-3-acetamido-3-((R)-sec-butyl)-2-oxopyrrolidin-1-yl)-4-phenylbutanoic acid (Preparation A, 18.1 mg, 0.050 mmol) in DMF (1 mL) was added HATU (22.8 mg, 0.06 mmol). A solution of (1S,2S)-2-amino-1-((2R,4R)-1-benzhydryl-4-(pyridin-3-yloxy)pyrrolidin-2-yl)-3-(3,5-difluorophenyl)propan-1-ol (Step 13 (B), 25.9 mg, 0.050 mmol) in DMF (1 mL) was then added, followed by N-methylmorpholine (23 μl, 0.21 mmol). The reaction mixture was stirred at rt for 3 h. pH 4 buffer was then added to quench. The mixture was extracted with ethyl acetate. The organic phase was washed with sat. aqueous NaCl, dried (MgSO$_4$), and concentrated in vacuo. The crude mixture was purified by reverse phase Prep HPLC to give the title compound (34 mg, 79% yield) as a clear, slightly brown glass: $^1$H NMR (CDCl$_3$, 300 MHz) δ 0.89 (3H, d, J=6 Hz), 1.00 (3H, m), 1.10-1.16 (1H, m), 1.59-2.16 (1H, m), 2.37 (1H, m), 2.47-2.54 (1H, m), 2.64 (1H, m), 2.90 (3H, m), 3.11-3.13 (2H, m), 3.27 (1H, m), 3.50 (2H, m), 3.96-3.99 (3H, m), 4.30 (1H, brd s), 5.19 (1H, s), 5.43 (1H, s), 6.58-6.60 (3H, m), 6.87 (1H, m), 7.11-7.38 (10H, m), 7.56 (2H, m), 7.71 (2H, d, J=6 Hz), 7.81 (1H, m), 8.00 (1H, d, J=6 Hz), 8.40 (1H, d, J=3 Hz), 8.77 (1H, s). HPLC retention time: 1.73 min (method A). MS (ESI) (M+H)$^+$ 858.31.

Step 13 (D): (S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-3-yloxy)pyrrolidin-2-yl)propan-2-yl)-4-phenylbutanamide. To a solution of (S)-2-((S)-3-acetamido-3-((R)-sec-butyl)-2-oxopyrrolidin-1-yl)-N-((1S,2S)-1-((2R,4R)-1-benzhydryl-4-(pyridin-3-yloxy)pyrrolidin-2-yl)-3-(3,5-difluorophenyl)-1-hydroxypropan-2-yl)-4-phenylbutanamide (Step 13 (C), 34 mg) in MeOH (2 mL) was added a catalytic amount of Pd/C (10 wt %). The reaction mixture was stirred under 1 atm. of H$_2$ for 5 h. The mixture was then filtered and concentrated in vacuo. Flash chromatography (silica gel, 0-7.5% methanol/chloroform) gave 19.9 mg (73% yield) of the title compound of Example 13 as an opaque oil: $^1$H NMR (CD$_3$OD, 500 MHz) δ 0.82 (3H, d, J=5 Hz), 1.01 (3H, t, J=5 Hz), 1.10-1.14 (1H, m), 1.69-1.73 (3H, m), 1.95-2.00 (4H, m), 2.04-2.08 (2H, m), 2.15-2.23 (3H, m), 2.33 (1H, m), 2.40 (1H, m), 2.55-2.60 (1H, m), 2.71-2.76 (2H, m), 3.12 (1H, dd, J=5, 10 Hz), 3.20 (1H, m), 3.37 (2H, m), 3.50 (1H, m), 3.90 (1H, m), 4.01 (1H, m), 4.10 (1H, dd, J=5, 10 Hz), 5.04 (1H, s), 6.70 (1H, m), 6.88 (2H, m), 7.16-7.20 (3H, m), 7.25-7.28 (2H, m), 7.38 (1H, dd, J=5, 10 Hz), 7.42 (1H, m), 8.15 (1H, m), 8.23 (1H, m). HPLC retention time: 1.50 min (method A). MS (ESI) (M+H)$^+$ 692.25. HRMS calcd for C$_{38}$H$_{48}$N$_5$O$_5$F$_2$ 692.3624 (MH$^+$), found 692.3656.

EXAMPLE 14

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-hydroxypyrrolidin-2-yl)propan-2-yl)-4-phenylbutanamide

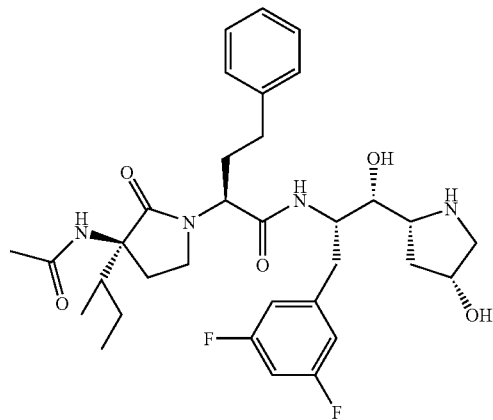

Step 14 (A): (3R,5R)-5-((1S,2S)-2-amino-3-(3,5-difluorophenyl)-1-hydroxypropyl)-1-benzhydrylpyrrolidin-3-ol. To a solution of (4S,5S)-4-(3,5-difluorobenzyl)-5-((2R,4R)-1-benzhydryl-4-hydroxypyrrolidin-2-yl)oxazolidin-2-one (Preparation J, 129 mg, 0.278 mmol) in EtOH (10 mL) was added a solution of LiOH (133 mg, 5.56 mmol) in $H_2O$ (2.5 mL). This reaction mixture was stirred at reflux for 3.5 h. After cooling down to rt, the mixture was concentrated to remove EtOH and the mixture was extracted with ethyl acetate and the organic phase was washed with sat. aqueous NaCl, dried ($MgSO_4$), and concentrated in vacuo. Flash chromatography (silica gel, 0-10% MeOH/chloroform) gave the title compound: $^1$H NMR ($CDCl_3$, 500 MHz) δ 2.00-2.05 (1H, m), 2.13-2.21 (1H, m), 2.40-2.61 (2H, m), 2.79-2.91 (2H, m), 3.21 (2H, d, J=15 Hz), 3.51 (1H, d, J=15 Hz), 4.26 (1H, m), 4.79 (1H, s), 6.62-6.70 (3H, m), 7.14-7.26 (4H, m), 7.30-7.35 (3H, m), 7.37-7.43 (3H, m). HPLC retention time: 1.19 min (method A). MS (ESI) (M+H)$^+$ 439.22.

Step 14 (B): (S)-2-((S)-3-acetamido-3-((R)-sec-butyl)-2-oxopyrrolidin-1-yl)-N-((1S,2S)-1-((2R,4R)-1-benzhydryl-4-hydroxypyrrolidin-2-yl)-3-(3,5-difluorophenyl)-1-hydroxypropan-2-yl)-4-phenylbutanamide. To a solution of (S)-2-((S)-3-acetamido-3-((R)-sec-butyl)-2-oxopyrrolidin-1-yl)-4-phenylbutanoic acid (Preparation A, 22.6 mg, 0.063 mmol) in DMF (1 mL) was added HATU (28.7 mg, 0.076 mmol). A solution of (3R,5R)-5-((1S,2S)-2-amino-3-(3,5-difluorophenyl)-1-hydroxypropyl)-1-benzhydrylpyrrolidin-3-ol (Step 14 (A), 27.5 mg, 0.063 mmol) in DMF (1 mL) was then added, followed by N-methylmorpholine (24.2 µl, 0.221 mmol). The reaction mixture was stirred at rt for 3 h. pH 4 buffer was then added to quench. The mixture was extracted with ethyl acetate. The organic phase was washed with sat. aqueous NaCl, dried ($MgSO_4$), and concentrated in vacuo. The crude mixture was purified by reverse phase Prep HPLC to give the title compound (32 mg, 65% yield) as a slightly yellow oil: $^1$H NMR ($CDCl_3$, 500 MHz) δ 0.88 (3H, d, J=10 Hz), 1.00 (3H, m), 1.07-1.18 (1H, m), 1.55-1.61 (1H, m), 1.72-1.78 (1H, m), 1.95-2.03 (4H, m), 2.05-2.11 (2H, m), 2.30 (2H, d, J=15 Hz), 2.38-2.47 (1H, m), 2.48-2.53 (1H, m), 2.64-2.70 (1H, m), 2.88 (1H, m), 3.03-3.08 (3H, m), 3.17-3.20 (1H, m), 3.49 (1H, s), 3.53-3.61 (3H, m), 3.91 (1H, d, J=10 Hz), 3.96 (3H, s), 4.11 (1H, m), 4.47 (1H, brd s), 4.96 (1H, brd s), 6.13 (1H, brd s), 6.58-6.67 (3H, m), 7.04-7.37 (10H, m), 7.49 (2H, m), 7.67 (2H, d, J=10 Hz). HPLC retention time: 1.67 min (method A). MS (ESI) (M+H)$^+$ 781.35.

Step 14 (C): (S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-hydroxypyrrolidin-2-yl)propan-2-yl)-4-phenylbutanamide. To a solution of (S)-2-((S)-3-acetamido-3-((R)-sec-butyl)-2-oxopyrrolidin-1-yl)-N-((1S,2S)-1-((2R,4R)-1-benzhydryl-4-hydroxypyrrolidin-2-yl)-3-(3,5-difluorophenyl)-1-hydroxypropan-2-yl)-4-phenylbutanamide (Step 14 (B), 32 mg) in MeOH (1 mL) was added a catalytic amount of Pd/C (10 wt %). The reaction mixture was stirred under 1 atm. of $H_2$ for 4 h. The mixture was then filtered and concentrated in vacuo. Flash chromatography (silica gel, 0-50% methanol/chloroform) gave 12.3 mg (50% yield) of the title compound of Example 14 as an opaque oil: $^1$H NMR ($CDCl_3$, 500 MHz) δ 0.84-0.91 (4H, m), 0.98 (3H, m), 1.07-1.15 (1H, m), 1.56-1.61 (1H, m), 1.74 (1H, m), 2.02 (3H, s), 2.06-2.27 (8H, m), 2.37-2.48 (2H, m), 2.69 (1H, t, J=10 Hz), 2.93 (1H, m), 3.14-3.22 (2H, m), 3.30 (1H, m), 3.47-3.51 (2H, m), 3.69 (1H, m), 3.97 (1H, m), 4.08 (1H, brd s), 4.43 (1H, brd s), 6.15 (1H, brd s), 6.51 (1H, m), 6.80 (2H, d, J=5 Hz), 7.05 (2H, d, J=10 Hz), 7.16 (1H, m), 7.22 (2H, d, J=5 Hz), 8.03 (1H,m). HPLC retention time: 1.58 min (method A). MS (ESI) (M+H)$^+$ 615.30.

EXAMPLE 15

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-hydroxypyrrolidin-2-yl)propan-2-yl)-4-phenylbutanamide

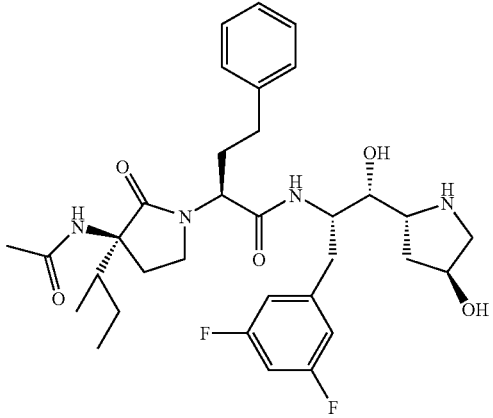

Sep 15 (A): (3S,5R)-5-((1S,2S)-2-amino-3-(3,5-difluorophenyl)-1-hydroxypropyl)-1-benzhydrylpyrrolidin-3-ol. To a solution of (4S,5S)-4-(3,5-difluorobenzyl)-5-((2R,4S)-1-benzhydryl-4-hydroxypyrrolidin-2-yl)oxazolidin-2-one (Preparation K, 60 mg, 0.129 mmol) in EtOH (5 mL) was added a solution of LiOH (62 mg, 2.58 mmol) in $H_2O$ (1.25 mL). This reaction mixture was stirred at reflux for 4 h. After cooling down to rt, the mixture was concentrated to remove EtOH and $H_2O$ was added followed by 1N HCl (8 mL) solution and pH 7 buffer. The mixture was extracted with ethyl acetate and the organic phase was washed with sat. aqueous NaCl, dried ($MgSO_4$), and concentrated in vacuo to give the title compound (47.3 mg, 84% yield) as an opaque oil: $^1$H NMR ($CDCl_3$, 300 MHz) δ 2.32-2.39 (1H, m), 2.49-2.62 (3H, m), 2.79-2.80 (1H, m), 3.18 (1H, d, J=12 Hz), 3.49-3.58 (2H, m), 4.28 (1H, t, J=6 Hz), 4.63 (1H, s), 5.55 (1H, s), 5.96 (4H, brd s), 6.62-6.68 (3H, m), 7.20-7.36 (6H, m), 7.77 (4H, d, J=6 Hz). HPLC retention time: 1.20 min (method A). MS (ESI) (M+H)$^+$ 439.16.

Step 15 (B): (S)-2-((S)-3-acetamido-3-((R)-sec-butyl)-2-oxopyrrolidin 1-yl)-N-((1S,2S)-1-((2R,4S)-1-benzhydryl-4-hydroxypyrrolidin-2-yl)-3-(3,5-difluorophenyl)-1-hydroxypropan-2-yl)-4-phenylbutanamide. To a solution of (S)-2-((S)-3-acetamido-3-((R)-sec-butyl)-2-oxopyrrolidin-1-yl)-

4-phenylbutanoic acid (Preparation A, 38.9 mg, 0.108 mmol) in DMF (2 mL) was added HATU (49.43 mg, 0.130 mmol). A solution of (3S,5R)-5-((1S,2S)-2-amino-3-(3,5-difluorophenyl)-1-hydroxypropyl)-1-benzhydrylpyrrolidin-3-ol (Step 15 (A), 47.3 mg, 0.108 mmol) in DMF (2 mL) was then added, followed by N-methylmorpholine (42 μl, 0.378 mmol). The reaction mixture was stirred at rt for 3 h. pH 4 buffer was then added to quench. The mixture was extracted with ethyl acetate. The organic phase was washed with sat. aqueous NaCl, dried (MgSO$_4$), and concentrated in vacuo. The crude mixture was purified by reverse phase Prep HPLC to give the title compound (60.5 mg, 72% yield) as a clear oil: $^1$H NMR (CDCl$_3$, 500 MHz) δ 0.87 (3H, d, J=10 Hz), 0.99 (3H, m), 1.08-1.17 (1H, m), 1.56-1.64 (1H, m), 1.72-1.77 (1H, m), 2.00-2.14 (6H, m), 2.20-2.39 (2H, m), 2.50-2.65 (2H, m), 2.68-2.81 (2H, m), 2.99-3.12 (3H, m), 3.32 (1H, d, J=15 Hz), 3.54-3.63 (3H, m), 3.90 (1H, d, J=5 Hz), 3.96-4.01 (3H, m), 4.60 (1H, s), 5.50 (1H, s), 6.13 (1H, s), 6.58-6.63 (3H, m), 7.13-7.37 (10H, m), 7.52 (2H, d, J=10 Hz), 7.69 (2H, d, J=10 Hz). HPLC retention time: 1.77 min (method A). MS (ESI) (M+H)$^+$ 781.38.

Step 15 (C): (S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-hydroxypyrrolidin-2-yl)propan-2-yl)-4-phenylbutanamide. To a solution of (S)-2-((S)-3-acetamido-3-((R)-sec-butyl)-2-oxopyrrolidin-1-yl)-N-((1S,2S)-1-((2R,4S)-1-benzhydryl-4-hydroxypyrrolidin-2-yl)-3-(3,5-difluorophenyl)-1-hydroxypropan-2-yl)-4-phenylbutanamide (Step 15 (B), 60.5 mg, 0.078 mmol) in MeOH (2 mL) was added a catalytic amount of Pd/C (10 wt %). The reaction mixture was stirred under 1 atm. of H$_2$ for 5 h. The mixture was then filtered and concentrated in vacuo. Flash chromatography (silica gel, 0-7.5% methanol/chloroform) gave 28.3 mg (60% yield) of the title compound of Example 15 as an opaque glass: $^1$H NMR (CD$_3$OD, 500 MHz) δ 0.90 (3H, d, J=5 Hz), 1.02 (3H, m), 1.10-1.20 (1H, m), 1.31 (1H, m), 1.69-1.76 (2H, m), 1.99-2.03 (4H, m), 2.04-2.17 (2H, m), 2.21 (2H, m), 2.42-2.49 (1H, m), 2.54-2.60 (1H, m), 2.66-2.76 (2H, m), 3.22 (1H, d, J=15 Hz), 3.28 (1H, m), 3.33-3.36 (1H, m), 3.44-3.49 (1H, m), 3.91-3.98 (2H, m), 4.05 (1H, m), 4.14 (1H, dd, J=5, 10 Hz), 4.56 (1H, m), 6.72 (1H, m), 6.89 (2H, d, J=10 Hz), 7.16-7.19 (3H, m), 7.26 (2H, m). HPLC retention time: 1.70 min (method A). MS (ESI) (M+H)$^+$ 615.32.

EXAMPLE 16

(S)-2-((S)-3-acetamido-3-((R)-sec-butyl)-2-oxopyrrolidin-1-yl)-N-((1S,2S)-3-(3,5-difluorophenyl)-1-hydroxy-1-((R)-morpholin-3-yl)propan-2-yl)-4-phenylbutanamide

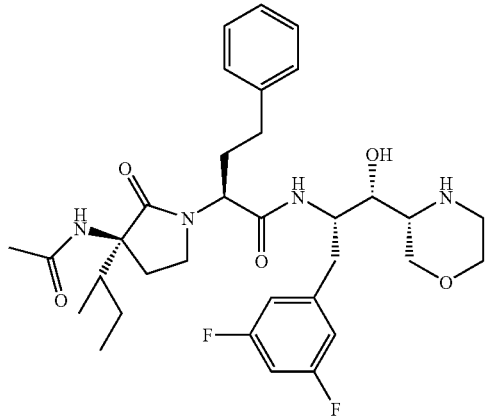

Step 16 (A): (S)-2-((S)-3-Acetamido-3-((R)-sec-butyl)-2-oxopyrrolidin-1-yl)-N-((1S,2S)-1-((R)-4-benzhydrylmorpholin-3-yl)-3-(3,5-difluorophenyl)-1-hydroxypropan-2-yl)-4-phenylbutanamide. To a solution of the compound of Preparation A (30 mg, 0.083 mmol) in CH$_2$Cl$_2$ was added HATU (38 mg, 0.1 mmol) and diisopropylethylamine (32 mg, 0.25 mmol). After stirring for 20 minutes at room temperature, the compound of Preparation L (36 mg, 0.083 mmol) was added. The reaction solution was stirred at room temperature overnight. The product was purified by flash chromatography eluting with 2:3 ethyl acetate/hexanes. $^1$H NMR (500 MHz, CDCl$_3$) δ ppm 0.72 (d, J=7.02 Hz, 3 H) 0.99 (t, J=7.17 Hz, 2 H) 1.35 (m, J=5.49 Hz, 1 H) 1.37 (d, J=6.71 Hz, 3 H) 1.66 (m, 2 H) 1.96 (s, 3 H) 2.17 (m, 3 H) 2.38 (d, J=9.16 Hz, 1 H) 2.65 (m, 3 H 3.21 (q, J=7.53 Hz, 1 H) 3.32 (m, 3 H) 3.40 (d, J=11.60 Hz, 1 H) 3.57 (m, 1 H) 3.71 (m, 1 H) 3.84 (d, J=11.29 Hz, 1 H) 3.94 (m, 1 H) 4.01 (dd, J=11.75, 2.59 Hz, 1 H) 4.24 (dd, J=9.00, 6.26 Hz, 1 H) 4.48 (dd, J=9.00, 1.98 Hz, 1 H) 4.99 (dd, J=11.60, 2.14 Hz, 1 H) 5.51 (s, 1 H) 6.76 (m, 1 H) 6.91 (d, J=6.71 Hz, 2 H) 7.18 (m, 7 H) 7.32 (t, J=7.63 Hz, 3 H) 7.36 (dd, J=8.39, 5.95 Hz, 2 H) 7.48 (m, 1 H) 7.55 (d, J=7.32 Hz, 2 H). MS (ESI) (M+H)$^+$=781.39.

Step 16 (B): To 20 mg of 10% Pd/C was added a solution of the entire sample of the compound of step 16 (A) in 5 ml of MeOH under nitrogen. A 0.3 ml portion of acetic acid was added. The mixture was shaken in a Parr apparatus with 50 psi of hydrogen for 3.5 hours. The suspension was filtered over Celite, and the product was purified by HPLC under standard conditions to give 30 mg (58.8% yield for the two steps) of the title compound of Example 16. $^1$H NMR (500 MHz, CDCl$_3$) δ ppm 0.90 (d, J=6.71 Hz, 3 H) 1.02 (t, J=7.17 Hz, 3 H) 1.13 (m, 1 H) 1.72 (m, 2 H) 2.00 (s, 3 H) 2.12 (m, 1 H) 2.21 (q, J=7.12 Hz, 2 H) 2.38 (m, 1 H) 2.57 (m, 1 H) 2.74 (m, 2 H) 3.23 (dd, J=14.34, 2.75 Hz, 1 H) 3.31 (m, 5 H) 3.42 (m, 2 H) 3.70 (m, 1 H) 3.77 (m, 1 H) 3.91 (m, 2 H) 3.99 (m, 2 H) 4.21 (dd, J=12.51, 3.05 Hz, 1 H) 6.73 (tt, J=9.16, 2.14 Hz, 1 H) 6.87 (d, J=7.94 Hz, 2 H) 7.19 (d, J=5.80 Hz, 3 H) 7.27 (m, 2 H) 8.12 (s, 1 H) 8.25 (d, J=8.85 Hz, 1 H).

MS (ESD (M+H)$^+$=615.34.

GENERAL PROCEDURE FOR EXAMPLES 17-21

Step 17-21 (A): To a solution of (2R,4R)-tert-butyl 2-((1S,2S)-2-((S)-2-((S)-3-acetamido-3-((R)-sec-butyl)-2-oxopyrrolidin-1-yl)-4-phenylbutanamido)-1-(tert-butyldimethylsilyloxy)-3-(3,5-difluorophenyl)propyl)-4-hydroxypyrrolidine-1-carboxylate (Preparation N, 50.0 mg, 60 mmol) in THF (250 uL) was added a 1 M solution of sodium bis(trimethylsilyl)amide in THF (120 uL, 120 mmol). To this mixture, the appropriate substituted benzyl bromide (120 mmol) or pyridylmethyl was added and allowed to stir at rt overnight. Buffer (pH 7) was added, and the mixture extracted with EtOAc, washed with brine, dried over MgSO$_4$, filtered, and concentrated in vacuo. Purification was effected by preparatory TLC.

Step 17-21 (B): The product from Step 17-21(A) was dissolved in 4 M HCl/dioxane (1 mL). Five drops of water were added, and the mixture stirred at rt for 1 h. Four mL 1 M NaOH was added, followed by pH 7 buffer. The mixture was extracted 3 times with EtOAc. The combined organic extracts were washed with brine, dried over MgSO$_4$, filtered and concentrated in vacuo. Purification was effected by preparatory TLC (10% MeOH/CHCL$_3$), to give the title compound.

EXAMPLE 17

(S)-N-((1R,2S)-1-((2R,4R)-4-(3,5-dimethoxybenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide

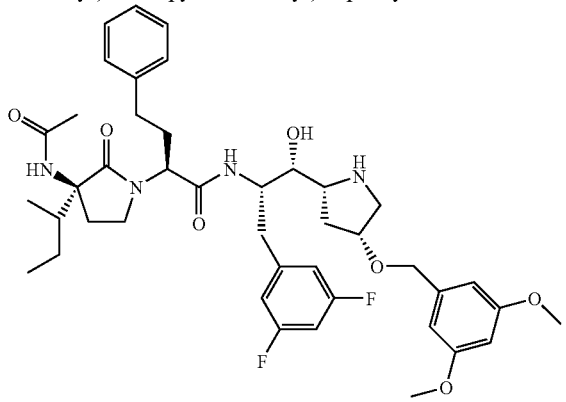

The general procedure above was followed using 3,5-dimethoxybenzyl bromide to afford the following:

Step 17 (A): (2R,4R)-tert-butyl 4-(3,5-dimethoxybenzyloxy)-2-((1S,2S)-2-((S)-2-((S)-3-acetamido-3-((R)-sec-butyl)-2-oxopyrrolidin-1-yl)-4-phenylbutanamido)-1-(tert-butyldimethylsilyloxy)-3-(3,5-difluorophenyl)propyl)pyrrolidine-1-carboxylate. HPLC retention time: 1.82 min (method D). MS (ESI) (M+H)$^+$ 979.70.

Step 17 (B): (S)-N-((1R,2S)-1-((2R,4R)-4-(3,5-dimethoxybenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide.

$^1$H NMR (CD$_3$OD, 500 MHz) δ 0.79 (3H, J=6.7 Hz, t), 1.00 (3H, J=7.0 Hz, t), 1.04-1.15 (1H, m), 1.28-1.34 (1H, m), 1.65-1.74 (2H, m), 1.85-1.92 (1H, m), 1.97 (3H, s), 2.00-2.32 (5H, m), 2.50-2.59 (1H, m), 2.67-2.80 (3H, m), 3.10-3.24 (3H, m), 3.28-3.32 (1H, m), 3.50 (1H, J=4.6, 9.8 Hz, dt), 3.77 (6H, s), 4.05-4.19 (3H, m), 4.42 (1H, J=12.2 Hz, d), 4.46 (1H, J=12.5 Hz, d), 6.40 (1H, J=2.3 Hz, t), 6.53 (2H, J=2.1 Hz, d), 6.70 (1H, J=2.1, 9.2 Hz, tt), 6.87-6.93 (2H, m), 7.14-7.21 (3H, m), 7.23-7.28 (2H, m). $^{13}$C NMR (CD$_3$OD, 500 MHz) δ 11.32, 12.41, 21.58, 23.13, 25.42, 30.79, 32.51, 32.88, 36.04, 40.88, 44.18, 52.43, 53.75, 54.76, 58.05, 60.42, 65.65, 70.76, 73.05, 79.92, 99.51, 101.37, 105.61, 112.26, 112.46, 126.05, 128.43, 141.10, 141.45, 143.64, 143.72, 161.40, 162.26, 164.22, 170.75, 172.34, 175.32. HPLC retention time: 1.98 min (method D). MS (ESI) (M+H)$^+$ 765.49.

EXAMPLE 18

(S)-N-((1R,2S)-1-((2R,4R)-4-(3-cyanobenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide

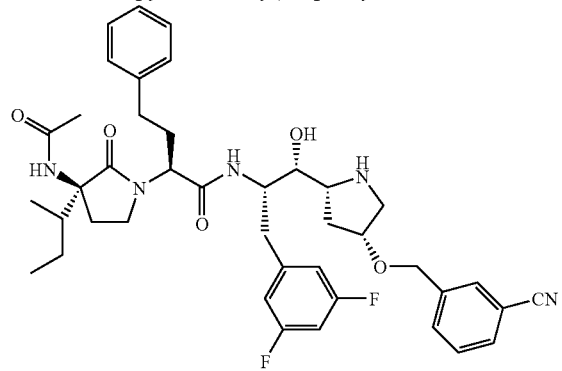

The general procedure above was followed using α-bromo-m-tolunitrile to afford the following:

Step 18 (A): (2R,4R)-tert-butyl 4-(3-cyanobenzyloxy)-2-((1S,2S)-2-((S)-2-((S)-3-acetamido-3-((R)-sec-butyl)-2-oxopyrrolidin-1-yl)-4-phenylbutanamido)-1-(tert-butyldimethylsilyloxy)-3-(3,5-difluorophenyl)propyl)pyrrolidine-1-carboxylate. MS (ESI) (M+H)$^+$ 944.69.

Step 18 (B): (S)-N-((1R,2S)-1-((2R,4R)-4-(3-cyanobenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide.

$^1$H NMR (CD$_3$OD, 500 MHz) δ 0.77 (3H, J=6.7 Hz, t), 1.00 (3H, J=7.2 Hz, t), 1.04-1.14 (1H, m), 1.29-1.34 (1H, m), 1.64-1.74 (2H, m), 1.86-1.93 (1H, m), 1.97 (3H, s), 1.99-2.32 (5H, m), 2.50-2.59 (1H, m), 2.67-2.79 (3H, m), 3.13 (1H, J=4.6, 7.9 Hz, dt), 3.16-3.24 (2H, m), 3.52 (1H, J=4.3, 9.8 Hz, dt), 3.78 (1H, J=4.6, 7.3 Hz, dd), 4.07-4.21 (3H, m), 4.53 (1H, J=12.5 Hz, d), 4.56 (1H, J=12.5 Hz, d), 6.70 (1H, J=2.3, 9.2 Hz, tt), 6.87-6.93 (2H, m), 7.14-7.20 (3H, m), 7.23-7.28 (2H, m), 7.50 (1H, J=7.8 Hz, t), 7.62 (1H, J=7.6 Hz, app d), 7.66 (1H, J=7.9 Hz, app d), 7.74 (1H, app s). $^{13}$C NMR (CD$_3$OD, 500 MHz) δ 11.33, 12.40, 21.58, 23.13, 25.41, 30.85, 32.51, 33.05, 35.90, 40.89, 44.11, 52.58, 53.68, 57.98, 60.43, 65.64, 69.41, 73.28, 80.67, 101.38, 101.58, 112.26, 112.34, 118.74, 126.06, 128.44, 128.55, 129.42, 131.01, 132.13, 140.95, 141.48, 143.67, 162.26, 162.36, 164.22, 164.32, 170.77, 172.34, 175.32. HPLC retention time: 1.90 min (method D). MS (ESI) (M+H)$^+$ 730.54.

EXAMPLE 19

(S)-N-((1R,2S)-1-((2R,4R)-4-(3-(trifluoromethyl)benzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide

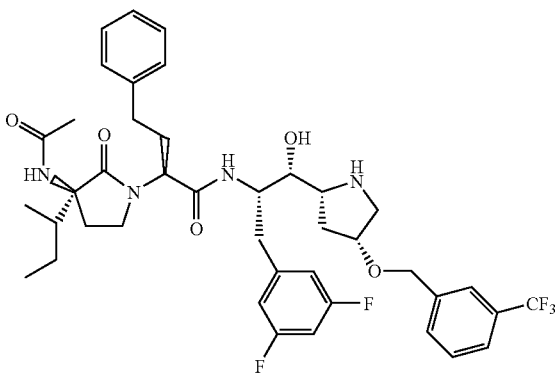

The general procedure above was followed using α'-bromo-α,α,α-trifluoro-m-xylene to afford the following:

Step 19 (A): (2R,4R)-tert-butyl 4-(3-(trifluoromethyl)benzyloxy)-2-((1S,2S)-2-((S)-2-((S)-3-acetamido-3-((R)-sec-butyl)-2-oxopyrrolidin-1-yl)-4-phenylbutanamido)-1-(tert-butyldimethylsilyloxy)-3-(3,5-difluorophenyl)propyl)pyrrolidine-1-carboxylate. HPLC retention time: 1.94 min (method D). MS (ESI) (M+H)$^+$ 987.67.

Step 19 (B): (S)-N-((1R,2S)-1-((2R,4R)-4-(3-(trifluoromethyl)benzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide. $^1$H NMR (CD$_3$OD, 500 MHz) δ 0.79 (3H, J=7.0 Hz, t), 1.00 (3H, J=7.2 Hz, t), 1.04-1.15 (1H, m), 1.64-1.75 (2H, m), 1.88-1.96 (1H, m), 1.98 (3H, s), 1.99-2.33 (6H, m), 2.50-2.59 (1H, m), 2.67-2.76 (2H, m), 2.81 (1H, J=5.0, 12.4 Hz, dd), 3.13-3.24 (3H, m), 3.51 (1H, J=4.3, 9.8 Hz, dt), 3.81 (1H, J=4.3, 7.6 Hz, dd), 4.05-4.21 (3H, m), 4.56 (1H, J=12.2 Hz, d), 4.60 (1H, J=12.2 Hz, d), 6.71 (1H, J=2.3, 9.2 Hz, tt), 6.90 (2H, J=6.4 Hz, d), 7.14-7.20 (3H, m), 7.23-7.29 (2H, m), 7.52 (1H, J=7.6 Hz, app t), 7.57 (1H, J=7.9 Hz, app d), 7.62 (1H, J=7.6 Hz, app d), 7.67 (1H, s). $^{13}$C NMR (CD$_3$OD, 500 MHz) δ 11.32, 12.42, 21.58, 23.13, 25.42, 30.82, 32.52, 32.83, 35.99, 40.88, 44.23, 52.45, 53.75, 58.10, 60.51, 65.65, 69.90, 72.96, 80.36, 101.38, 112.26, 112.46, 124.18, 126.07, 128.54, 129.11, 131.26, 140.35, 141.45, 170.80, 172.35, 175.33. HPLC retention time: 2.04 min (method D). MS (ESI) (M+H)$^+$ 773.77.

25.40, 30.83, 32.51, 33.01, 35.97, 40.88, 44.08, 52.52, 53.69, 57.97, 60.40, 65.64, 70.01, 73.22, 80.12, 101.38, 112.46, 114.87, 115.05, 126.07, 128.44, 128.54, 129.76, 129.82, 134.81, 141.46, 170.74, 172.34, 175.32, 179.86. HPLC retention time: 1.98 min (method D). MS (ESI) (M+H)$^+$ 723.64.

EXAMPLE 20

(S)-N-((1R,2S)-1-((2R,4R)-4-(4-fluorobenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide

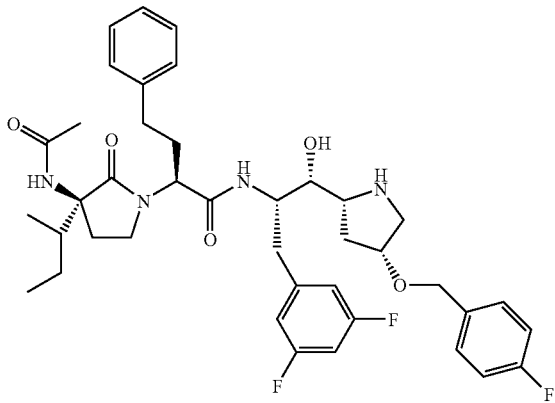

The general procedure above was followed using 4-fluorobenzyl bromide to afford the following:

Step 20 (A): (2R,4R)-tert-butyl 4-(4-fluorobenzyloxy)-2-((1S,2S)-2-((S)-2-((S)-3-acetamido-3-((R)-sec-butyl)-2-oxopyrrolidin-1-yl)-4-phenylbutanamido)-1-(tert-butyldimethylsilyloxy)-3-(3,5-difluorophenyl)propyl)pyrrolidine-1-carboxylate. HPLC retention time: 1.77 min (method D). MS (ESI) (M+H)$^+$ 937.67.

Step 20 (B): (S)-N-((1R,2S)-1-((2R,4R)-4-(4-fluorobenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide.

$^1$H NMR (CD$_3$OD, 500 MHz) δ 0.78 (3H, J=7.0 Hz, t), 1.00 (3H, J=7.2 Hz, t), 1.03-1.15 (1H, m), 1.65-1.74 (2H, m), 1.83-1.90 (1H, m), 1.97 (3H, s), 1.99-2.32 (6H, m), 2.50-2.59 (1H, m), 2.67-2.78 (3H, m), 3.08-3.23 (3H, m), 3.51 (1H, J=4.3, 9.8 Hz, dt), 3.77 (1H, J=4.3, 7.6 Hz, dd), 4.06-4.20 (3H, m), 4.45 (1H, J=11.6 Hz, d), 4.49 (1H, J=11.6 Hz, d), 6.71 (1H, J=2.1, 9.2 Hz, tt), 6.87-6.92 (2H, m), 7.01-7.07 (2H, m), 7.14-7.20 (3H, m), 7.23-7.28 (2H, m), 7.34-7.39 (2H, m). $^{13}$C NMR (CD$_3$OD, 500 MHz) δ 11.32, 12.40, 21.57, 23.13,

EXAMPLE 21

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-2-ylmethoxy)pyrrolidin-2-yl)propan-2-yl)-4-phenylbutanamide

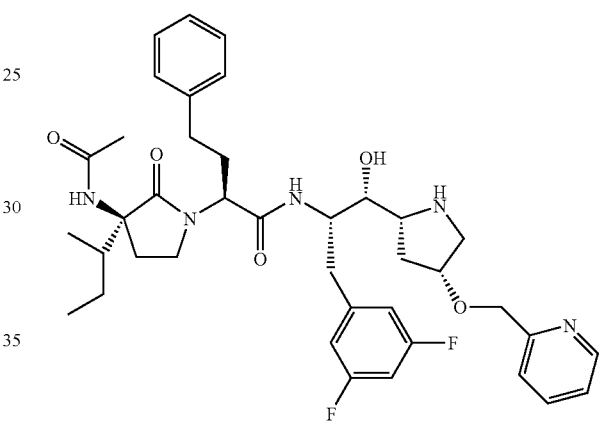

The general procedure above was followed using 2-bromomethylpyridine hydrobromide and 180 uL of 1 M sodium bis(trimethylsilyl)amide in THF to afford the following:

Step 21 (A): (2R,4R)-tert-butyl 2-((1S,2S)-2-((S)-2-((S)-3-acetamido-3-((R)-sec-butyl)-2-oxopyrrolidin-1-yl)-4-phenylbutanamido)-1-(tert-butyldimethylsilyloxy)-3-(3,5-difluorophenyl)propyl)-4-(pyridin-2-ylmethoxy)pyrrolidine-1-carboxylate.

Step 21 (B): (S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-2-ylmethoxy)pyrrolidin-2-yl)propan-2-yl)-4-phenylbutanamide. $^1$H NMR (CD$_3$OD, 500 MHz) 0.78 (3H, J=6.7 Hz, t), 1.00 (3H, J=7.2 Hz, t), 1.04-1.15 (1H, m), 1.64-1.74 (2H, m), 1.89-2.32 (7H, m), 1.97 (3H, s), 2.50-2.59 (1H, m), 2.67-2.81 (3H, m), 3.11-3.25 (3H, m), 3.52 (1H, J=4.4, 9.8 Hz, dt), 3.79 (1H, J=4.6, 7.6 Hz, dd), 4.06-4.14 (1H, m), 4.15-4.23 (2H, m), 4.58 (1H, J=12.8 Hz, d), 4.61 (1H, J=12.8 Hz, d), 6.71 (1H, J=2.2, 9.2 Hz, tt), 6.87-6.93 (2H, m), 7.14-7.34 (6H, m), 7.55 (1H, J=7.9 Hz, d), 7.81 (1H, J=1.7, 7.7 Hz, dt). $^{13}$C NMR (CD$_3$OD, 500 MHz) δ 11.32, 12.39, 21.58, 23.12, 25.39, 30.86, 32.51, 33.01, 35.86, 40.89, 44.06, 52.53, 53.68, 57.93, 60.47, 65.64, 71.05, 73.24, 80.89, 101.37, 101.58, 112.25, 112.45, 122.46, 123.10, 126.06, 128.55, 137.83, 141.49, 143.67, 148.50, 158.50, 162.26, 164.33, 170.74, 172.33, 175.32. HPLC retention time: 1.70 min (method D). MS (ESI) (M+H)$^+$ 706.45.

EXAMPLE 22

(S)-2-((S)-3-acetamido-3-((R)-sec-butyl)-2-oxopyrrolidin-1-yl)-N-((1R,2S)-1-hydroxy-3-phenyl-1-((2R,4R)-4-(propylsulfonyl)pyrrolidin-2-yl)propan-2-yl)-4-phenylbutanamide

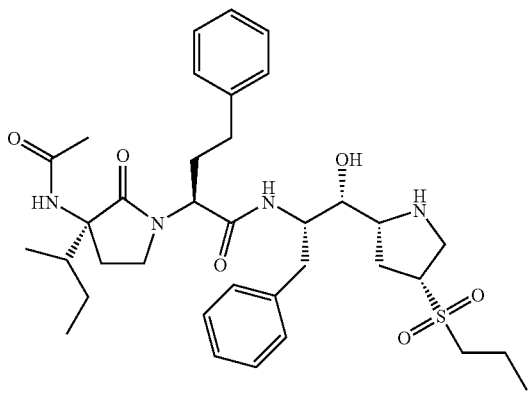

Step 22 (A): (2R,4R)-tert-butyl 2-((1S,2S)-2-(benzyloxycarbonyl)-1-(tert-butyldimethylsilyloxy)-3-phenylpropyl)-4-hydroxypyrrolidine-1-carboxylate. A solution of the compound of Preparation O (230 mg, 0.37 mmol) dissolved in a mixture of 3 mL of ethanol and 0.5 mL of water was treated with Wilkinson's catalyst (28 mg, 8% by weight). The resulting solution was heated to 95° C. for 16 h, then allowed to cool to rt. A solution of $KMnO_4$ (117 mg, 0.74 mmol) dissolved in 0.4 mL of water was then added, followed by methanol until the solution became homogeneous, and the resulting reaction solution was stirred rt for 16 h. The reaction solution was then partitioned between ethyl acetate and water and the organic layer was separated, dried, and concentrated to a crude product which was purified using column chromatography to provide 110 mg of the desired alcohol (51%). $^1$H NMR (500 MHz, $CDCl_3$) δ 0.12 (m, 6 H) 0.95 (s, 9 H) 1.47 (s, 9 H) 2.16 (s, 2 H) 2.38 (t, J=11.90 Hz, 1 H) 3.27 (d, J=10.68 Hz, 2 H) 3.50 (d, J=6.71 Hz, 1 H) 3.61 (s, 1 H) 3.77 (s, 1 H) 3.94 (d, J=11.60 Hz, 1 H) 4.20 (s, 2 H) 4.37 (dd, J=7.32, 2.14 Hz, 1 H) 4.82 (s, 1 H) 4.94 (d, J=8.85 Hz, 1 H) 7.21 (m, 10 H)

MS (ESI) (M+H–Boc)$^+$485.23.

Step 22 (B): (2R,4S)-tert-butyl 2-((1S,2S)-2-(benzyloxycarbonyl)-1-(tert-butyldimethylsilyloxy)-3-phenylpropyl)-4-(methylsulfonyloxy)pyrrolidine-1-carboxylate. A solution 126 mg of triphenylphosphine (0.48 mmol) in THF (3 mL) was treated with 84 mg (0.48 mmol) of a 40% solution of DEAD in toluene. After stirring for 5 min, 43 mg of methanesulfonic acid was added. After another 5 min, a solution of the compound of Step 22 (A) (90 mg, 0.16 mmol) dissolved in an additional 3 mL of THF was added, followed by DIPEA (124 mg, 0.96 mmol). The reaction solution was stirred at rt for 30 min, then heated to 60° C. for 4.5 hr. The cooled reaction solution was partitioned between ethyl acetate and water, the organic layer was concentrated, and the crude product was purified by chromatography eluting with a gradient of 5 to 20% ethyl acetate in hexanes to provide 100 mg (94%) of the desired mesylate. $^1$H NMR (500 MHz, $CDCl_3$) δ 0.02 (s, 3 H) 0.11 (s, 3 H) 0.92 (s, 9 H) 1.48 (s, 9 H) 2.30 (m, 2 H) 2.46 (d, J=6.10 Hz, 1 H) 2.92 (m, 2 H) 3.28 (d, J=13.12 Hz, 2 H) 3.41 (d, J=12.21 Hz, 1 H) 3.89 (d, J=12.82 Hz, 1 H) 4.18 (m, 1 H) 4.30 (m, 3 H) 4.66 (d, J=9.16 Hz, 1 H) 4.82 (d, J=12.21 Hz, 1 H) 4.94 (d, J=9.16 Hz, 1 H) 5.16 (s, 1 H) 7.19 (m, 10 H). MS (ESI) (M+H–Boc)$^+$=563.24.

Step 22 (C): (2R,4R)-tert-butyl 2-((1S,2S)-2-(benzyloxycarbonyl)-1-(tert-butyldimethylsilyloxy)-3-phenylpropyl)-4-(propylthio)pyrrolidine-1-carboxylate. A solution of 4 mmol of propanethiol and 4 mmol (160 mg) of a 60% dispersion of sodium hydride in mineral oil were dissolved in 4 mL of DMF, and the solution was allowed to stip until the production of hydrogen gas ceased. A solution of the compound of step 22 (B) (200 mg, 0.30 mmol) dissolved in 3 mL of DMF was then treated with 1.5 mL of the above solution of thiolate anion and the reaction solution was stirred at rt for 16 h. The reaction solution was partitioned between ethyl acetate and water, the organic layer was concentrated, and the crude product was purified by chromatography eluting with a gradient of 5 to 20% ethyl acetate in hexanes to provide 130 mg (67%) of the desired thiol and 27 mg (16%) of the corresponding elimination product. $^1$H NMR (500 MHz, $CDCl_3$) δ 0.06 (d, J=29.91 Hz, 6 H) 0.94 (s, 9 H) 0.98 (t, J=7.17 Hz, 3 H) 1.47 (s, 9 H) 1.60 (td, J=14.57, 7.17 Hz, 2 H) 1.69 (s, 1 H) 2.13 (s, 2 H) 2.28 (m, 1 H) 2.38 (s, 1 H) 2.52 (s, 2 H) 2.95 (m, 2 H) 3.22 (dd, J=43.49, 12.97 Hz, 1 H) 3.91 (m, 1 H) 4.10 (m, 1 H) 4.24 (d, J=7.32 Hz, 1 H) 4.77 (m, 1 H) 4.95 (m, 1 H) 7.19 (m, 10 H). MS (ESI) (M+H)$^+$=643.35

Step 22 (D): (2R,4R)-tert-butyl 2-((1S,2S)-2-(benzyloxycarbonyl)-1-(tert-butyldimethylsilyloxy)-3-phenylpropyl)-4-(propylsulfonyl)pyrrolidine-1-carboxylate. A solution of 130 mg (0.2 mmol) of the compound of step 22 (C) dissolved in 2 mL of methanol was treated with a solution of 240 mg (0.4 mmol) of oxone dissolved in 0.4 mL of water. After stirring at rt for 30 min, the reaction solution was partitioned between ethyl acetate and water, the organic layer was concentrated, and the crude product was purified by chromatography eluting with a gradient of 20 to 80% ethyl acetate in hexanes to provide 86 mg (64%) of the desired sulfone and 37 mg (28%) of the sulfoxide intermediate as a lower-eluting compound. $^1$H NMR (500 MHz, $CDCl_3$) δ 0.06 (s, 3 H) 0.11 (s, 3 H) 0.96 (s, 9 H) 1.07 (t, J=7.32 Hz, 3 H) 1.47 (s, 9 H) 1.87 (dd, J=13.43, 6.71 Hz, 3 H) 2.03 (s, 1 H) 2.26 (t, J=12.21 Hz, 1 H) 2.38 (s, 1 H) 2.68 (s, 1 H) 2.90 (s, 2 H) 3.46 (m, 2 H) 3.75 (s, 1 H) 4.09 (m, 2 H) 4.26 (d, J=7.02 Hz, 1 H) 4.77 (m, 1 H) 4.95 (m, 1 H) 7.18 (m, 10 H) MS (ESI) (M+H–Boc)$^+$=575.25

Step 22 (E): (2R,4R)-tert-butyl 2-((1S,2S)-2-amino-1-(tert-butyldimethylsilyloxy)-3-phenylpropyl)-4-(propylsulfonyl)pyrrolidine-1-carboxylate. A 30 mg portion of 10% palladium on carbon was solvated with 5 mL of MeOH and then 86 mg (0.13 mmol) of the compound of step 22 (D) was added. The reaction mixture was placed under 50 psi of hydrogen gas in a Parr apparatus and shaken for 3 h. The catalyst was removed by filtration through a glass fiber filter to provide the amine (68 mg, 99%). $^1$H NMR (500 MHz, $CDCl_3$) δ 0.06 (m, 6 H) 0.93 (s, 9 H) 1.08 (t, J=7.02 Hz, 3 H) 1.47 (s, 9 H) 1.90 (d, J=7.32 Hz, 2 H) 2.27 (m, 1 H) 2.35 (dd, J=12.82, 6.71 Hz, 1 H) 2.74 (s, 1 H) 2.90 (m, 3 H) 2.98 (ddd, J=10.68, 5.49, 2.44 Hz, 1 H) 3.13 (d, J=12.21 Hz, 1 H) 3.46 (d, J=8.24 Hz, 2 H) 4.00 (s, 1 H) 4.19 (d, J=2.14 Hz, 1 H) 4.30 (s, 1 H) 4.38 (s, 1 H) 7.22 (m, 5 H). MS (ESI) (M+H)$^+$=541.32

Step 22 (F): (2R,4R)-tert-butyl 2-((1S,2S)-2-((S)-2-((S)-3-acetamido-3-((R)-sec-butyl)-2-oxopyrrolidin-1-yl)-4-phenylbutanamido)-1-(tert-butyldimethylsilyloxy)-3-phenylpropyl)-4-(propylsulfonyl)pyrrolidine-1-carboxylate. A solution of the compound of Preparation A (22 mg, 0.06 mmol) dissolved in 2 mL of dichloromethane was treated with DEEA (40 mg, 0.3 mmol) and HATU (30 mg, 0.078 mmol). After stirring at rt for 5 min, the amine from step 22 (E) (32 mg, 0.06 mmol) was added and the reaction solution was allowed to stir for 16 h at rt. The reaction solution was then partitioned between ethyl acetate and water, the organic layer was concentrated, and the crude product was purified by chromatography eluting with a gradient of 40% to 80% ethyl acetate in hexanes to provide 45 mg (85%) of the desired amide. $^1$H NMR (500 MHz, Solvent) δ ppm 0.08 (s, 6 H) 0.18 (s, 2 H) 0.73 (d, J=6.71 Hz, 3 H) 0.99 (s, 9 H) 1.10 (m, 6 H) 1.37 (t, J=6.41 Hz, 6 H) 1.49 (s, 9 H) 1.52 (d, J=3.97 Hz, 4 H) 1.68 (m, 1 H) 1.86 (m, 2 H) 2.09 (m, 1 H) 2.58 (m, 1 H) 2.73 (m, 1 H) 3.05 (dd, J=9.16, 6.41 Hz, 2 H) 3.23 (m, 2 H) 3.54 (s, 1 H) 3.76 (m, 2 H) 4.02 (m, 2 H) 4.09 (m, 1 H) 4.26 (s, 1 H) 4.41 (d, J=8.55 Hz, 1 H) 7.22 (m, 10 H) 8.18 (s, 1 H). MS (ESI) (M+H)$^+$=883.41

Step 22 (G): (S)-2-((S)-3-acetamido-3-((R)-sec-butyl)-2-oxopyrrolidin-1-yl)-N-((1R,2S)-1-hydroxy-3-phenyl-1-((2R,4R)-4-(propylsulfonyl)pyrrolidin-2-yl)propan-2-yl)-4-phenylbutanamide. A 45 mg (0.05 mmol) portion of the compound of step 22 (F) was dissolved in 1 mL of 4 M HCl in dioxane, and 100 μL of water was added. After stirring at rt for 3 h, the solvents were removed and the crude product was purified by prep HLPC under standard conditions to provide 30 mg of the title compound as the TFA salt (90%). $^1$H NMR (500 MHz, CDCl$_3$) δ ppm 0.91 (d, J=6.71 Hz, 3 H) 1.02 (t, J=7.17 Hz, 3 H) 1.12 (t, J=7.48 Hz, 3 H) 1.15 (m, 1 H) 1.72 (m, 2 H) 1.87 (td, J=15.26, 7.32 Hz, 2 H) 1.99 (s, 3 H) 2.12 (m, 3 H) 2.37 (m, 1 H) 2.52 (m, 3 H) 2.68 (m, 1 H) 2.83 (dd, J=13.58, 11.14 Hz, 1 H) 3.14 (m, 2 H) 3.26 (m, 3 H) 3.29 (d, J=5.19 Hz, 2 H) 3.72 (m, 2 H) 3.81 (m, 3 H) 4.13 (m, 1 H) 4.21 (dd, J=9.31, 2.29 Hz, 1 H) 7.23 (m, 10 H) 8.08 (s, 1 H) 8.15 (d, J=8.55 Hz, 1 H). MS (ESI) (M+H)$^+$=669.35.

BIOLOGICAL METHODS

There are a number of methods by which inhibitors of the BACE enzyme can be identified experimentally. The enzyme can be obtained from membrane samples from natural tissues or cultured cells or can be expressed recombinantly in a host cell by well known methods of molecular biology. The whole enzyme or a portion thereof can be expressed, for example, in bacterial, insect or mammalian cells to obtain a catalytically active enzyme species. The enzymatic activity and/or ligand binding capability of the enzyme can be assessed within these membrane samples, or the enzyme can be purified to varying extents. As an illustrative example, the nucleic acid sequence encoding the pro and catalytic domains of human BACE can be appended on the 5' end with an untranslated and signal sequence from the gene for acetylcholinesterase, and on the 3' end with a sequence encoding a poly-histidine tag. This cDNA can then be expressed in *Drosophila melanogaster* S2 cells in which the signal and pro sequences of the transcribed/translated protein are removed by cellular proteases and the catalytic domain, appended by a C-terminal poly-histidine tag, is secreted out into the cellular medium. The enzyme can then be purified from the culture medium by nickel affinity chromatography by methods well known to those trained in the art [Mallender, W. et al., (2001) "Characterization of recombinant, soluble beta-secretase from an insect cell expression system." *Mol. Pharmacol.* 59: 619-626]. Similar strategies for expressing and purifying various forms of BACE in bacterial, mammalian and other cell types would be known to one skilled in the art. A preferred method for determining the potency of a test compound in binding to the BACE enzyme is by moitoring the the displacement of a suitable radioligand.

Radioligand displacement assays with a radiolabeled BACE inhibitor (WO 2004 013098, compound 3, where the methoxy group is substituted for C($^3$H)$_3$) were carried out using standard methods (Keen, M. (1999) in *Receptor Binding Techniques* (Walker, J. M. ed) p. 106 Humana Press, Totowa, N.J.). The HEK293-9B.A1 cell line, which overexpresses the BACE1 enzyme, was derived from HEK293 cells (Simmons, N. L. (1990) A cultured human renal epithelioid cell line responsive to vasoactive intestinal peptide. *Exp. Physiol.* 75:309-19.) by RAGE™ (Harrington, J. J. et al. (2001) Creation of genome-wide protein expression libraries using random activation of gene expression. *Nat. Biotechnol.* 19:440-5; U.S. Pat. Nos. 6,410,266 and 6,361,972). T225 flask cultures of HEK293-9B.A1 were grown to 80% confluency in DMEM supplemented with 2 mM L-glutamine, 10 μg/ml penecillin, 10 μg/ml streptomycin, 3 μg/ml puromycin, 100 nM methotrexate, and 10% fetal bovine serum (Invitrogen, Carlsbad, Calif.), harvested, and resuspended at 2×10$^8$ cells per 10 ml of lysis buffer consisting of 50 mM HEPES pH 7.0 containing a protease inhibitor cocktail of AEBSF 104 μM, aprotinin 80 nM, leupeptin 2 μM, bestatin 4 μM, pepstatin A 1.5 μM, and E-64 1.4 μM (0.1% of protease inhibitor cocktail P8340, Sigma-Aldrich, St. Louis, Mo.) at 4° C. The resuspended cells were homogenized using a Polytron (Brinkman, Westbury, N.Y.) at setting 6 for 10 sec., then centrifuged at 48,000×g for 10 min. The resulting pellet was washed by repeating the resuspension, homogenization and centrifugation steps. The final pellet was resuspended in buffer at 4° C. to yield a total protein concentration of 5 mg/ml, then aliquots were frozen in liquid nitrogen for further storage at −70° C. Immediately before carrying out a binding assay, an aliquot of cell homogenate was thawed and diluted to a concentration of 100 μg/ml in assay buffer consisting of 50 mM HEPES pH 5.0 and 0.1% CHAPSO. Assays were initiated in polypropylene 96-well plates (Costar, Cambridge, Mass.) by the addition of 200 μl of cell homogenate to 50 μl of assay buffer containing 1 nM radioligand (WO 2004 013098, compound 3, where the methoxy group is substituted for C($^3$H)$_3$: 80 Ci/mMol) and various concentrations of unlabelled compounds, and incubated for 1.5 hr. at 25° C. Separation of bound from free radioligand was by filtration on GFF glass fiber filters (Innotech Biosystems International, Lansing, Mich.) using an Innotech cell harvester. Filters were washed three times with 0.3 ml of phosphate buffered saline pH 7.0 at 4° C. and assessed for radioactivity using a Wallac 1450 Microbeta liquid scintillation counter (PerkinElmer, Boston, Mass.). Ki values of competing compounds were derived through Cheng-Prussoff correction of IC50 values calculated using XLfit (IDBS, Guildford, UK).

Abbreviations:

AEBSF: 4-(2-Aminoethyl)benzenesulfonyl fluoride hydrochloride

CHAPSO: 3-[(3-Cholamidopropyl)dimethylammonio]-2-hydroxy-1-propanesulfonate

D-MEM: Dulbecco's modified eagle medium

HEPES: 4-(2-Hydroxyethyl)piperazine-1-ethanesulfonic acid

RAGE™: Random Activation of Gene Expression™

The activity of specific compounds described herein and tested in the above assay is provided in Table 1.

TABLE 1

| Compound of Example | Activity Rating[a] |
|---|---|
| 2 | +++ |
| 7 | ++ |
| 8 | +++ |
| 15 | +++ |
| 22 | +++ |

[a]Activity based on IC$_{50}$ values: +++ = <0.1 μM ++ = 0.1-1.0 μM

In Vitro Assay to Identify β-Secretase Inhibitor Based on the Inhibition of Aβ Formation from Membrane Preparations.

An isolated membrane fraction which contains functionally active β-secretase and K-APP substrates can generate β-secretase cleavage products including Aβ (Roberts, S. B.; Hendrick, J. P.; Vinitsky, A.; Lewis, M.; Smith, D. W.; Pak, R. PCT Publication WO 01/0175435; Fechteler, K.; Kostka, M.; Fuchs, M. Patent Application No. DE 99-19941039; Shearman, M.; Beher, D. et al., *Biochemistry*, 2000, 39, 8698-8704; Zhang, L. Song, L. et al., *Biochemistry* 2001, 40, 5049-5055). An isolated membrane fraction can be prepared from human derived cell lines such as HeLa and H4 which have been transfected with wild type or mutant forms of β-APP or a human alkaline phosphatase β-APP fusion construct, and stably express high levels of β-secretase substrates. The endogenous β-secretase present in the isolated membranes prepared at 0-4° C. cleaves the β-APP substrates when the membranes are shifted from 0-4 to 37° C. Detection of the cleavage products including Aβ can be monitored by standard techniques such as immunoprecipitation (Citron, M.; Diehl, T. S. et al., *Proc. Natl. Acad. Sci. USA*, 1996, 93,13170-13175), western blot (Klafki, H.-W.; Ambramowski, D. et al., *J. Biol. Chem.* 1996, 271, 28655-28659), enzyme linked immunosorbent assay (ELISA) as demonstrated by Seubert, P.; Vigo-Pelfrey, C. et al., *Nature*, 1992, 359, 325-327, or by a preferred method using time-resolved fluorescence of the homogeneous sample containing membranes and Aβ (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000, 39, 8698-8704). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the β-secretase cleavage. The second antibody binds to any other epitope present on Aβ. For example, antibodies that bind the N-terminal region (e.g., 26D6-B2-B3® SIBIA Neurosciences, La Jolla, Calif.) or bind the C-terminal end (e.g., 9S3.2® antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of β-secretase. The isolated membrane assay can be used to identify candidate agents that inhibit the activity of β-secretase cleavage and Aβ production.

A typical membrane-based assay requires 45 µg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plant or marine samples. All synthetic agents are initially screened at doses ranging from 10-100 µM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantitation of Aβ is described elsewhere (Roberts, S. B.; Hendrick, J. P.; Vinitsky, A.; Lewis, M.; Smith, D. W.; Pak, R. PCT Publication WO 01/0175435; Shearman, M.; Beher, D. et al, *Biochemistry*, 2000. 39, 8698-8704). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. Compounds of the present application are considered active when tested in the above assay if the $IC_{50}$ value for the test compound is less than 50 µM. A preferred $IC_{50}$ value is less than 1 µM. A more preferred $IC_{50}$ value is less than 0.1 µM. If a compound is found to be active then a dose response experiment is performed to determine the lowest dose of compound necessary to elicit the inhibition of the production of Aβ.

In Vivo Assays for the Determination of Aβ Reduction by a β-Secretase Inhibitor.

In vivo assays are available to demonstrate the inhibition of β-secretase activity. In these assays, animals, such as mice, that express normal levels of APP, β- and γ-secretase or are engineered to express higher levels of APP and hence Aβ can be used to demonstrate the utility of β-secretase inhibitors, as demonstrated with γ-secretase inhibitors [Dovey, H. et al., (2001), J. Neurochem. 76: 173-181]. In these assays, β-secretase inhibitors are administered to animals and Aβ levels in multiple compartments, such as plasma, cerebral spinal fluid, and brain extracts, are monitored for Aβ levels using methods previously outlined. For instance, Tg2576 mice, which over-express human APP, are administered β-secretase inhibitors by oral gavage at doses that will cause measurable Aβ lowering, typically less than 100 mg/kg. Three hours after dosing plasma, brain, and CSF are collected, frozen in liquid nitrogen, and stored at −80° C. until analysis. For Aβ detection, plasma is diluted 15-fold in PBS with 0.1% Chaps while CSF is diluted 15-fold in 1% Chaps with protease inhibitors (5 µg/ml leupeptin, 30 µg/ml aprotinin, 1 mM phenylmethylsulfonylfluoride, 1 µM pepstatin). Brains are homogenized in 1% Chaps with protease inhibitors using 24 ml solution/g brain tissue. Homogenates were then centrifuged at 100,000×g for 1 hr at 4° C. The resulting supernatants were then diluted 10-fold in 1% Chaps with protease inhibitors. Aβ levels in the plasma, CSF, and brain lysate can then be measured using time-resolved fluorescence of the homogenous sample or one of the other methods previously described.

A β-secretase inhibitor is considered active in one of the above in vivo assays if it reduces Aβ by at least 50% at a dosage of 100 mg/kg.

DOSAGE AND FORMULATION

The compounds of the present application can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this application can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present application will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present application may be administered in a single daily dose, or the total daily dosage may be administered in divided doses of two, three, or four times daily.

The compounds for the present application can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present application, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present disclosure can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present disclosure may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present dislcosure may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:
1. A compound of Formula (I); or a stereoisomer thereof

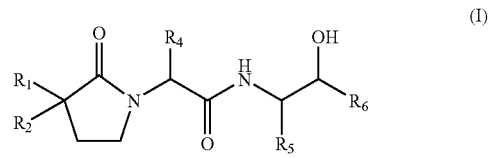

wherein
$R_1$ is hydrogen, $C_{1-6}$alkyl or $NHR_3$;
$R_2$ is $C_{1-6}$alkyl, $C_{3-6}$alkenyl, $C_{3-6}$cycloalkyl or $C_{3-6}$cycloalkyl($C_{1-4}$alkyl) in which each group is optionally substituted with a group selected from halogen, $CF_3$, $CF_2H$, OH, $OCF_3$ and $C_{1-4}$alkoxy;
$R_3$ is $-C(=O)R_{10}$, $-C(=O)OR_{10}$, $-C(=O)NHR_{10}$, $-S(O)_nR_{10}$ or $C_{1-6}$alkyl optionally substituted with a group selected from $C_{3-6}$cycloalkyl, halogen, $CF_3$, $OCF_3$, OH, $C_{1-4}$alkoxy and CN;

$R_4$ is $C_{1-6}$alkyl, $C_{3-6}$cycloalkyl, $C_{3-6}$cycloalkyl($C_{1-4}$alkyl), phenyl or phenyl($C_{1-4}$alkyl) in which each group is optionally substituted with the group selected from halogen, $C_{1-4}$alkyl, OH, $C_{1-4}$alkoxy, $CF_3$, $CF_2H$, $OCF_3$ and CN;

$R_5$ is $C_{1-6}$alkyl, phenyl or phenyl($C_{1-4}$alkyl) in which each group is optionally substituted with one or two groups selected from halogen, $C_{1-4}$alkyl, OH, $CF_3$, $OCF_3$ and CN;

$R_6$ is

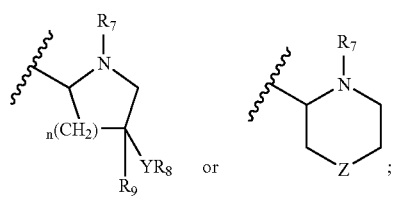

$R_7$ is hydrogen or $C_{1-4}$alkyl;
n is 1 or 2;
Y is O, $NR_7$ or $S(O)_n$;
Z is $CH_2$, O or S;
$R_8$ and $R_9$ each are independently hydrogen, $C_{1-4}$alkyl, $C_{3-6}$alkenyl, $C_{3-6}$alkynyl, phenyl or pyridyl in which said phenyl and pyridyl are optionally substituted with $C_{1-4}$alkyl, fluoro$C_{1-4}$alkyl, $C_{1-4}$alkoxy, halogen or CN; or
$YR_8$ and $R_9$ are joined together with the carbon to which they are attached to form a 5- or 6-membered ring wherein Y is oxygen, and $R_8$ and $R_9$ are $-CH_2(CH_2)_n-O-$; and
$R_{10}$ is $C_{1-4}$alkyl optionally substituted with the group selected from halogen, OH, $CF_3$, $NH_2$ and $C_{1-4}$alkoxy;
or a nontoxic pharmaceutically acceptable salt thereof.

2. The compound according to claim 1 of Formula (I); or a stereoisomer thereof,

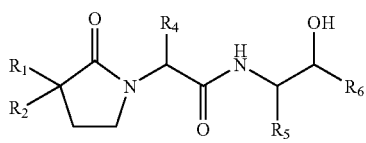

wherein
$R_1$ is hydrogen or $NHR_3$;
$R_2$ is $C_{1-6}$alkyl, $C_{3-6}$alkenyl, or $C_{3-6}$cycloalkyl($C_{1-4}$alkyl) in which each group is optionally substituted with a group selected from halogen, $CF_3$, $CF_2H$, OH, and $C_{1-4}$alkoxy;
$R_3$ is $-C(=O)R_{10}$, $-S(O)_nR_{10}$ or $C_{1-6}$alkyl optionally substituted with a group selected from $C_{3-6}$cycloalkyl, halogen, $CF_3$, $OCF_3$, OH, $C_{1-4}$alkoxy and CN;
$R_4$ is $C_{1-6}$alkyl, $C_{3-6}$cycloalkyl($C_{1-4}$alkyl) or phenyl($C_{1-4}$alkyl) in which each group is optionally substituted with the group selected from halogen, $C_{1-4}$alkyl, OH, $C_{1-4}$alkoxy, $CF_3$, $OCF_3$ and CN;
$R_5$ is $C_{1-6}$alkyl, or phenyl($C_{1-4}$alkyl) in which each group is optionally substituted with one or two groups selected from halogen, $C_{1-4}$alkyl and OH;

$R_6$ is

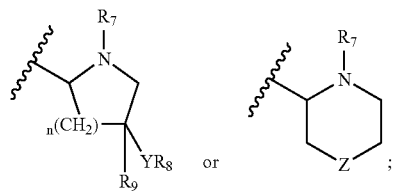

$R_7$ is hydrogen;
n is 1;
Y is O, NH or $SO_2$;
Z is $CH_2$ or O;
$R_8$ and $R_9$ each are independently hydrogen, $C_{1-4}$alkyl, $C_{3-6}$alkenyl, phenyl or pyridyl in which said phenyl and pyridyl are optionally substituted with $C_{1-4}$alkyl, fluoro$C_{1-4}$alkyl, $C_{1-4}$alkoxy, halogen or CN; or $YR_8$ and $R_9$ are joined together with the carbon to which they are attached to form a 5- or 6-membered ring wherein Y is oxygen, and $R_8$ and $R_9$ are $-CH_2(CH_2)_n-O-$; and
$R_{10}$ is $C_{1-4}$alkyl optionally substituted with the group selected from halogen, OH, $CF_3$, $NH_2$ and $C_{1-4}$alkoxy;
or a nontoxic pharmaceutically acceptable salt thereof.

3. The compound according to claim 2 of Formula (Ia); or a stereoisomer thereof,

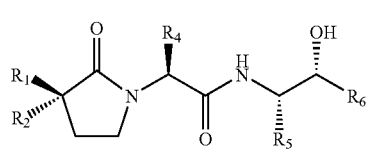

wherein
$R_1$ is hydrogen or $NHR_3$;
$R_2$ is $C_{1-6}$alkyl or $C_{3-6}$cycloalkyl($C_{1-4}$alkyl) in which each group is optionally substituted with a group selected from halogen, $CF_3$, OH, and $C_{1-4}$alkoxy;
$R_3$ is $-C(=O)R_{10}$;
$R_4$ is $C_{1-6}$alkyl or phenyl($C_{1-4}$alkyl) in which each group is optionally substituted with the group selected from halogen, $C_{1-4}$alkyl, $C_{1-4}$alkoxy, and $CF_3$;
$R_5$ is $C_{1-6}$alkyl, or phenyl($C_{1-4}$alkyl) in which each group is optionally substituted with one or two halogen;
$R_6$ is

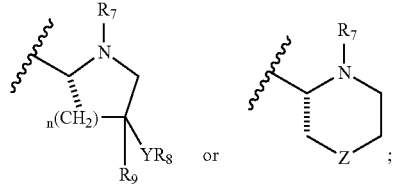

$R_7$ is hydrogen;
n is 1;
Y is O, NH or $SO_2$;
Z is $CH_2$ or O;
$R_8$ and $R_9$ each are independently hydrogen, $C_{1-4}$alkyl, $C_{3-6}$alkenyl, phenyl or pyridyl in which said phenyl and pyridyl are optionally substituted with $C_{1-4}$alkyl, fluoro$C_{1-4}$alkyl, $C_{1-4}$alkoxy, halogen or CN; and $R_{10}$ is $C_{1-4}$alkyl optionally substituted with the group selected from OH, $CF_3$, and $C_{1-4}$alkoxy;

or a nontoxic pharmaceutically acceptable salt thereof.

4. The compound according to claim 3 of Formula (Ib);

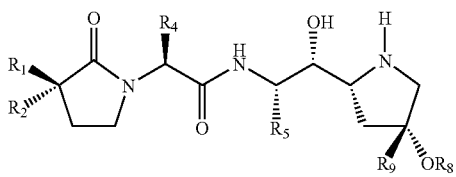

(Ib)

wherein $R_1$ is hydrogen or $NHR_3$;

$R_2$ is $C_{1-6}$alkyl or $C_{3-6}$cycloalkyl($C_{1-4}$alkyl) in which each group is optionally substituted with a group selected from $CF_3$, OH, and $C_{1-4}$alkoxy;

$R_3$ is —C(=O)$R_{10}$;

$R_4$ is $C_{1-6}$alkyl or phenyl($C_{1-4}$alkyl) in which each group is optionally substituted with the group selected from halogen, $C_{1-4}$alkyl, $C_{1-4}$alkoxy, and $CF_3$;

$R_5$ is benzyl or 3,5-difluorobenzyl;

$R_8$ and $R_9$ each are independently hydrogen, $C_{1-4}$alkyl, $C_{3-6}$alkenyl, phenyl or pyridyl in which said phenyl and pyridyl are optionally substituted with $C_{1-4}$alkyl, fluoro$C_{1-4}$alkyl, $C_{1-4}$alkoxy, halogen or CN; and $R_{10}$ is $C_{1-4}$alkyl optionally substituted with the group selected from OH, $CF_3$, and $C_{1-4}$alkoxy;

or a nontoxic pharmaceutically acceptable salt thereof.

5. The compound according to claim 3 of Formula (Ic);

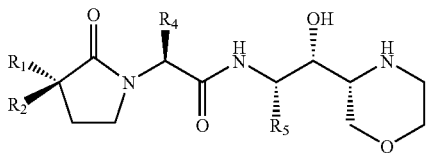

(Ic)

wherein $R_1$ is $C_{1-6}$alkyl or $C_{3-6}$cycloalkyl($C_{1-4}$alkyl) in which each group is optionally substituted with a group selected from $CF_3$, OH, and $C_{1-4}$alkoxy;

$R_2$ is hydrogen or $NHR_3$;

$R_3$ is —C(=O)$R_{10}$;

$R_4$ is $C_{1-6}$alkyl or phenyl($C_{1-4}$alkyl) in which each group is optionally substituted with the group selected from halogen, $C_{1-4}$alkyl, $C_{1-4}$alkoxy, and $CF_3$;

$R_5$ is benzyl or 3,5-difluorobenzyl;

$R_{10}$ is $C_{1-4}$alkyl optionally substituted with the group selected from OH, $CF_3$, and $C_{1-4}$alkoxy;

or a nontoxic pharmaceutically acceptable salt thereof.

6. The compound of claim 1 selected from the group consisting of:

(S)-2-((R)-3-acetamido-3-isobutyl-2-oxopyrrolidin-1-yl)-N-((1R,2S)-3-(3,5-difluorophenyl)-1-hydroxy-1-((2R,4R)-4-propoxypyrrolidin-2-yl)propan-2-yl)-4-phenylbutanamide;

(S)-2-((R)-3-acetamido-3-secbutyl-2-oxopyrrolidin-1-yl)-N-((1R,2S)-3-(3,5-difluorophenyl)-1-hydroxy-1-((2R,4R)-4-propoxypyrrolidin-2-yl)propan-2-yl)-4-phenylbutanamide;

(S)-((1R,2S)-3-(3,5-difluorophenyl)-1-hydroxy-1-((2R,4R)-4-propoxypyrrolidin-2-yl)propan-2-yl) 2-((S)-3-butyl-2-oxopyrrolidin-1-yl)-4-phenylbutanoate;

(S)-((1R,2S)-3-(3,5-difluorophenyl)-1-hydroxy-1-((2R,4R)-4-propoxypyrrolidin-2-yl)propan-2-yl) 2-((S)-3-butyl-2-oxopyrrolidin-1-yl)propanoate;

(S)-((1R,2S)-3-(3,5-difluorophenyl)-1-hydroxy-1-((2R,4R)-4-propoxypyrrolidin-2-yl)propan-2-yl) 2-((R)-3-isopropyl-2-oxopyrrolidin-1-yl)-4-phenylbutanoate;

(S)-((1R,2S)-3-(3,5-difluorophenyl)-1-hydroxy-1-((2R,4R)-4-propoxypyrrolidin-2-yl)propan-2-yl) 2-((S)-3-isobutyl-2-oxopyrrolidin-1-yl)-4-phenylbutanoate;

(S)-((1R,2S)-3-(3,5-difluorophenyl)-1-hydroxy-1-((2R,4R)-4-propoxypyrrolidin-2-yl)propan-2-yl) 2-((S)-3-isobutyl-2-oxopyrrolidin-1-yl)propanoate;

(S)-2-((S)-3-acetamido-3-((R)-sec-butyl)-2-oxopyrrolidin-1-yl)-N-((1R,2S)-3-(3,5-difluorophenyl)-1-hydroxy-1-((R)-piperidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-phenoxypyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-(pyridin-2-yloxy)pyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-phenoxypyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-2-yloxy)pyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-3-yloxy)pyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-hydroxypyrrolidin-2-yl)propan-2-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4S)-4-hydroxypyrrolidin-2-yl)propan-2-yl)-4-phenylbutanamide;

(S)-2-((S)-3-acetamido-3-((R)-sec-butyl)-2-oxopyrrolidin-1-yl)-N-((1S,2S)-3-(3,5-difluorophenyl)-1-hydroxy-1-((R)-morpholin-3-yl)propan-2-yl)-4-phenylbutanamide;

(S)-N-((1R,2S)-1-((2R,4R)-4-(3,5-dimethoxybenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide;

(S)-N-((1R,2S)-1-((2R,4R)-4-(3-cyanobenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide;

(S)-N-((1R,2S)-1-((2R,4R)-4-(3-(trifluoromethyl)benzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide;

(S)-N-((1R,2S)-1-((2R,4R)-4-(4-fluorobenzyloxy)pyrrolidin-2-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide;

(S)-2-((S)-3-acetamido-3-((R)-sec-butyl)-2-oxopyrrolidin-1-yl)-N-((1R,2S)-3-(3,5-difluorophenyl)-1-hydroxy-1-((2R,4R)-4-(pyridin-2-ylmethoxy)pyrrolidin-2-yl)propan-2-yl)-4-phenylbutanamide; and (S)-2-((S)-3-acetamido-3-((R)-sec-butyl)-2-oxopyrrolidin-1-yl)-N-((1R,2S)-1-hydroxy-3-phenyl-1-((2R,4R)-4-(propylsulfonyl)pyrrolidin-2-yl)propan-2-yl)-4-phenylbutanamide.

7. A pharmaceutical composition a therapeutically effective amount of a compound of claim 1 in association with a pharmaceutically acceptable adjuvant, carrier or diluent.

8. A method for the treatment of Alzheimer's Disease, cerebral amyloid angiopathy and Down's Syndrome which comprises administering a therapeutically effective amount of a compound of claim 1.

* * * * *